United States Patent
Miller et al.

(10) Patent No.: US 10,184,120 B2
(45) Date of Patent: Jan. 22, 2019

(54) MODIFIED KZ144 ENDOLYSIN SEQUENCE

(71) Applicant: Lysando AG, Triesenberg (LI)

(72) Inventors: Stefan Miller, Regensburg (DE);
Reinhard Sterner, Regensburg (DE);
Heike Stüer, Pentling (DE)

(73) Assignee: LYSANDO AG, Triesenberg (LI)

( * ) Notice: Subject to any disclaimer, the term of this patent is extended or adjusted under 35 U.S.C. 154(b) by 329 days.

(21) Appl. No.: 15/036,569

(22) PCT Filed: Nov. 14, 2014

(86) PCT No.: PCT/EP2014/074671
§ 371 (c)(1),
(2) Date: May 13, 2016

(87) PCT Pub. No.: WO2015/071436
PCT Pub. Date: May 21, 2015

(65) Prior Publication Data
US 2016/0281074 A1 Sep. 29, 2016

(30) Foreign Application Priority Data
Nov. 14, 2013 (WO) ............... PCT/EP2013/073869

(51) Int. Cl.
*C12N 9/36* (2006.01)
*A61K 38/47* (2006.01)
*C12N 9/50* (2006.01)

(52) U.S. Cl.
CPC ............ *C12N 9/2462* (2013.01); *A61K 38/47* (2013.01); *C12N 9/503* (2013.01); *C12Y 302/01017* (2013.01)

(58) Field of Classification Search
None
See application file for complete search history.

(56) References Cited

U.S. PATENT DOCUMENTS 9,534,223 B2 * 1/2017 Miller .................. C12N 9/2462

FOREIGN PATENT DOCUMENTS

| EP | 0285123 | 10/1988 |
|----|---------|---------|
| JP | 64-20089 | 1/1989 |
| WO | WO 2010/023207 | 3/2010 |
| WO | WO 2010/149792 | 12/2010 |
| WO | WO 2010/149795 | 12/2010 |
| WO | WO 2012/085259 | 6/2012 |

OTHER PUBLICATIONS

Briers et al., "Muralytic activity and modular structure of the endolysins of *Pseudomonas aeruginosa* bacteriophages phiKZ and EL," *Molecular Microbiology*, 65(5):1334-1344, 2007.
Briers et al., "The high-affinity peptidoglycan binding domain of *Psuedomonas* phage endolysin KZ144," *Biochemical and Biophysical Research Communications*, 383(2):187-191, 2009.
Ding et al., "The Sushi peptides: structural characterization and mode of action against Gram-negative bacteria," *Cell Mol Life Sci.*, 65(7-8):1202-1219, 2008.
Fokine et al., "Structure of the Bacteriophage phi KZ Lytic Transglycosylase gp144," *The Journal of Biological Chemistry*, 283(11):7242-7250, 2008.
Lopez et al., "Enzymes for anti-infective therapy: phage lysins," *Drug Discovery Today: Therapeutic Strategies*, 1(4):469-474, 2004.
PCT International Search Report and Written Opinion issued in International Application No. PCT/EP2014/07467, dated Mar. 11, 2015.
Tan et al., "Definition of endotoxin binding sites in horseshoe crab factor C recombinant sushi proteins and neutralization of endotoxin by sushi peptides," *FASEB J.*, 14(12):1801-1813, 2000.

* cited by examiner

*Primary Examiner* — Suzanne M Noakes
*Assistant Examiner* — Jae W Lee
(74) *Attorney, Agent, or Firm* — Parker Highlander PLLC

(57) ABSTRACT

The present invention relates to polypeptides comprising an amino acid sequence exhibiting at least about 90% sequence identity with the sequence of SEQ ID NO: 1. Said polypeptides preferably degrade the peptidoglycan of Gram-negative bacteria, in particular of *Pseudomonas* and/or *Campylobacter* bacteria. In addition, the present invention relates to nucleic acids encoding such polypeptides, vectors comprising such nucleic acids, and corresponding host cells. Finally, the present invention relates to compositions comprising such polypeptides, nucleic acids, vectors, and/or host cells according to the present invention.

20 Claims, 4 Drawing Sheets
Specification includes a Sequence Listing.

SEQ ID NO:1

XKVLRKGDRGDEVXQLQTLLNLXGYDVGKPDGIFGNNTFNQVVKFQKDNXLDSDGIVGK
NTWAELFSKYSPPIPYKTIPMPXANKSRAAATPVMNAVENATGVRSQLLLTFASIESAFDY
EXKAKTSSATGWFQFLTGTWKTMIENYGXKYGVXTDPTGXLRKDPRXSALMGAELIKEX
XNILRPXLKREPTDTDLYLAHFFGPGXARRFLXTGQNELAATHFXKEAQAXPXIFYNKDGS
PKTIQEVYNLMDGKVAAHRK

SEQ ID NO:2

KVLRKGDRGDEVCQLQTLLNLCGYDVGKPDGIFGNNTFNQVVKFQKDNCLDSDGIVGKN
TWAELFSKYSPPIPYKTIPMPTANKSRAAATPVMNAVENATGVRSQLLLTFASIESAFDYEI
KAKTSSATGWFQFLTGTWKTMIENYGMKYGVLTDPTGALRKDPRISALMGAELIKENMNI
LRPVLKREPTDTDLYLAHFFGPGAARRFLTTGQNELAATHFPKEAQANPSIFYNKDGSPK
TIQEVYNLMDGKVAAHRK

SEQ ID NO:3 (M=Selenomethionine)

KVLRKGDRGDEVCQLQTLLNLCGYDVGKPDGIFGNNTFNQVVKFQKDNCLDSDGIVGKN
TWAELFSKYSPPIPYKTIPMPTANKSRAAATPVMNAVENATGVRSQLLLTFASIESAFDYEI
KAKTSSATGWFQFLTGTWKTMIENYGMKYGVLTDPTGALRKDPRISALMGAELIKENMNI
LRPVLKREPTDTDLYLAHFFGPGAARRFLTTGQNELAATHFPKEAQANPSIFYNKDGSPK
TIQEVYNLMDGKVAAHRK

SEQ ID NO:4

KVLRKGDRGDEVCQLQTLLNLCGYDVGKPDGIFGNNTFNQVVKFQKDNCLDSDGIVGKN
TWAELFSKYSPPIPYKTIPMPTANKSRAAATPVMNAVENATGVRSQLLLTFASIASAFDYEI
KAKTSSATGWFQFLTGTWKTMIENYGMKYGVLTDPTGALRKDPRISALMGAELIKENMNI
LRPVLKREPTDTDLYLAHFFGPGAARRFLTTGQNELAATHFPKEAQANPSIFYNKDGSPK
TIQEVYNLMDGKVAAHRK

Fig.1a

SEQ ID NO:5

MKVLRKGDRGDEVCQLQTLLNLCGYDVGKPDGIFGNNTFNQVVKFQKDNCLDSDGIVGK
NTWAELFSKYSPPIPYKTIPMPTANKSRAAATPVMNAVENATGVRSQLLLTFASIESAFDY
EIKAKTSSATGWFQFLTGTWKTMIENYGMKYGVLTDPTGALRKDPRISALMGAELIKENM
NILRPVLKREPTDTDLYLAHFFGPGAARRFLTTGQNELAATHFPKEAQANPSIFYNKDGSP
KTIQEVYNLMDGKVAAHRK

Fig.1b

SEQ ID NO:136

MRGLRRLGRKIAHGVKKYGPTVLRIIRIAGGSKVLRKGDRGDEVsQLQTLLNLCGYDVGK
PDGIFGNNTFNQVVKFQKDNsLDSDGIVGKNTWAELFSKYSPPIPYKTIPMPTANKSRAAA
TPVMNAVENATGVRSQLLLTFASIESAFDYEIKAKTSSATGWFQFLTGTWKTMIENYGMK
YGVLTDPTGALRKDPRISALMGAELIKENMNILRPVLKREPTDTDLYLAHFFGPGAARRFL
TTGQNELAATHFPKEAQANPSIFYNKDGSPKTIQEVYNLMDGKVAAHRKLEHHHHHH

SEQ ID NO:137

MRGLRRLGRKIAHGVKKYGPTVLRIIRIAGGSKVLRKGDRGDEVCQLQTLLNLCGYDVGK
PDGIFGNNTFNQVVKFQKDNCLDSDGIVGKNTWAELFSKYSPPIPYKTIPMPiANKSRAAA
TPVMNAVENATGVRSQLLLTFASIESAFDYEIKAKTSSATGWFQFLTGTWKTMIENYGMK
YGVLTDPTGALRKDPRISALMGAELIKENMNILRPVLKREPTDTDLYLAHFFGPGvARRFL
TTGQNELAATHFPKEAQANPtIFYNKDGSPKTIQEVYNLMDGKVAAHRKLEHHHHHH

SEQ ID NO:138

MRGLRRLGRKIAHGVKKYGPTVLRIIRIAGGSKVLRKGDRGDEVCQLQTLLNLCGYDVGK
PDGIFGNNTFNQVVKFQKDNCLDSDGIVGKNTWAELFSKYSPPIPYKTIPMPiANKSRAAA
TPVMNAVENATGVRSQLLLTFASIESAFDYEmKAKTSSATGWFQFLTGTWKTMIENYGM
KYGVLTDPTGtLRKDPRISALMGAELIKENMNILRPVLKREPTDTDLYLAHFFGPGvARRFL
TTGQNELAATHFPKEAQANPtIFYNKDGSPKTIQEVYNLMDGKVAAHRKLEHHHHHH

SEQ ID NO:139

MRGLRRLGRKIAHGVKKYGPTVLRIIRIAGGSKVLRKGDRGDEVsQLQTLLNLCGYDVGK
PDGIFGNNTFNQVVKFQKDNsLDSDGIVGKNTWAELFSKYSPPIPYKTIPMPTANKSRAAA
TPVMNAVENATGVRSQLLLTFASIESAFDYEmKAKTSSATGWFQFLTGTWKTMIENYGM
KYGVLTDPTGtLRKDPRISALMGAELIKENMNILRPVLKREPTDTDLYLAHFFGPGAARRFL
TTGQNELAATHFPKEAQANPSIFYNKDGSPKTIQEVYNLMDGKVAAHRKLEHHHHHH

Fig.2a

SEQ ID NO:140

MRGLRRLGRKIAHGVKKYGPTVLRIIRIAGGSKVLRKGDRGDEVsQLQTLLNLsGYDVGKP
DGIFGNNTFNQVVKFQKDNsLDSDGIVGKNTWAELFSKYSPPIPYKTIPMPTANKSRAAAT
PVMNAVENATGVRSQLLLTFASIESAFDYEIKAKTSSATGWFQFLTGTWKTMIENYGMKY
GVLTDPTGALRKDPRISALMGAELIKENMNILRPVLKREPTDTDLYLAHFFGPGAARRFLT
TGQNELAATHFPKEAQANPSIFYNKDGSPKTIQEVYNLMDGKVAAHRKLEHHHHHH

SEQ ID NO:141

MRGLRRLGRKIAHGVKKYGPTVLRIIRIAGGSKVLRKGDRGDEVsQLQTLLNLCGYDVGK
PDGIFGNNTFNQVVKFQKDNsLDSDGIVGKNTWAELFSKYSPPIPYKTIPMPiANKSRAAA
TPVMNAVENATGVRSQLLLTFASIESAFDYEmKAKTSSATGWFQFLTGTWKTMIENYGM
KYGVLTDPTGtLRKDPRISALMGAELIKENMNILRPVLKREPTDTDLYLAHFFGPGvARRFL
TTGQNELAATHFPKEAQANPtIFYNKDGSPKTIQEVYNLMDGKVAAHRKLEHHHHHH

SEQ ID NO:142

MRGLRRLGRKIAHGVKKYGPTVLRIIRIAGGSKVLRKGDRGDEVsQLQTLLNLCGYDVGK
PDGIFGNNTFNQVVKFQKDNsLDSDGIVGKNTWAELFSKYSPPIPYKTIPMPiANKSRAAA
TPVMNAVENATGVRSQLLLTFASIESAFDYEmKAKTSSATGWFQFLTGTWKTMIENYGM
KYGVLTDPTGtLRKDPRISALMGAELIKENMNILRPVLKREPTDTDLYLAHFFGPGnARRFL
TTGQNELAATHFPKEAQANPtIFYNKDGSPKTIQEVYNLMDGKVAAHRKLEHHHHHH

SEQ ID NO:151

MRGLRRLGRKIAHGVKKYGPTVLRIIRIAGGSKVLRKGDRGDEVCQLQTLLNLCGYDVGK
PDGIFGNNTFNQVVKFQKDNCLDSDGIVGKNTWAELFSKYSPPIPYKTIPMPTANKSRAA
ATPVMNAVENATGVRSQLLLTFASIESAFDYEIKAKTSSATGWFQFLTGTWKTMIENYGM
KYGVLTDPTGALRKDPRISALMGAELIKENMNILRPVLKREPTDTDLYLAHFFGPGAARRF
LTTGQNELAATHFPKEAQANPSIFYNKDGSPKTIQEVYNLMDGKVAAHRKLEHHHHHH

Fig.2b

US 10,184,120 B2

MODIFIED KZ144 ENDOLYSIN SEQUENCE

This application is a national phase application under 35 U.S.C. § 371 of International Application No. PCT/EP2014/074671, filed Nov. 14, 2014, which claims benefit of priority to International Application No. PCT/EP2013/073869, filed Nov. 14, 2013, the entire contents of each of which are hereby incorporated by reference.

The present invention relates to polypeptides comprising an amino acid sequence exhibiting at least about 90% sequence identity with the sequence of SEQ ID NO: 1. Said polypeptides preferably degrade the peptidoglycan of Gram-negative bacteria, in particular of *Pseudomonas* and/or *Campylobacter* bacteria. In addition, the present invention relates to nucleic acids encoding such polypeptides, vectors comprising such nucleic acids, and corresponding host cells. Finally, the present invention relates to compositions comprising such polypeptides, nucleic acids, vectors, and/or host cells according to the present invention.

The giant, lytic Myoviridae bacteriophage φKZ (280334 bp) infects *Pseudomonas aeruginosa*, an important opportunistic nosocomial pathogen resistant to many commonly used antibiotics, and is therefore the cause of considerable concern in hospital environments. In 2007, Briers et al. (Molecular Microbiology (2007) 65(5), 1334-1344) sequenced the genome of said bacteriophage and identified the endolysin KZ144, a highly lytic peptidoglycan hydrolase. In WO 2010/149792, a fusion protein comprising the sequence of said endolysin as enzymatic element has been proposed for use in degrading the cell wall of Gram-negative bacteria.

While said endolysin and fusion proteins are effective in general, it turned out, that for some technical applications the endolysin polypeptide exhibits suboptimal characteristics, in particular in terms of stability and processing. Thus, there was a need in the art for a further endolysin enzyme, which exhibits preferably improved characteristics in this respect. The problem of the present invention was thus to provide such polypeptide.

The problem is solved by the subject-matter as set forth in the appended claims.

In the following a brief description of the appended figures will be given. The figures are intended to illustrate the present invention in more detail. However, they are not intended to limit the subject matter of the invention to any extent.

FIG. 1: illustrates:
SEQ ID NO: 1,
SEQ ID NO: 2 KZ144 endolysin without N-terminal methionine,
SEQ ID NO: 3 KZ144 endolysin without N-terminal methionine and with selenomethionine residues instead of methionine residues,
SEQ ID NO: 4 KZ144 endolysin with E115A mutation without N-terminal methionine, and
SEQ ID NO: 5 KZ144 endolysin.
FIG. 2: illustrates:
SEQ ID NO: 136 Fusion protein of SMAP-29 (underlined with solid line; SEQ ID NO: 76), modified KZ144 without N-terminal methionine and with C14S and C50S (underlined with semi-dotted/semi-solid line; SEQ ID NO: 28) and His-tag (underlined with dotted line; SEQ ID NO: 135).
SEQ ID NO: 137 Fusion protein of SMAP-29 (underlined with solid line; SEQ ID NO: 76), modified KZ144 without N-terminal methionine and with T82I, A206V and S232T (underlined with semi-dotted/semi-solid line; SEQ ID NO: 29) and His-tag (underlined with dotted line; SEQ ID NO: 135).
SEQ ID NO: 138 Fusion protein of SMAP-29 (underlined with solid line; SEQ ID NO: 76), modified KZ144 without N-terminal methionine and with T82I, A206V, S232T, I122M; and A160T (underlined with semi-dotted/semi-solid line; SEQ ID NO: 30) and His-tag (underlined with dotted line; SEQ ID NO: 135).
SEQ ID NO: 139 Fusion protein of SMAP-29 (underlined with solid line; SEQ ID NO: 76), modified KZ144 without N-terminal methionine and with C14S, C50S, I122M; and A160T (underlined with semi-dotted/semi-solid line; SEQ ID NO: 31) and His-tag (underlined with dotted line; SEQ ID NO: 135).
SEQ ID NO: 140 Fusion protein of SMAP-29 (underlined with solid line; SEQ ID NO: 76), modified KZ144 without N-terminal methionine and with C14S, C23S and C50S (underlined with semi-dotted/semi-solid line; SEQ ID NO: 32) and His-tag (underlined with dotted line; SEQ ID NO: 135).
SEQ ID NO: 141 Fusion protein of SMAP-29 (underlined with solid line; SEQ ID NO: 76), modified KZ144 without N-terminal methionine and with T82I, A206V, S232T, I122M; A160T, C14S and C50S (underlined with semi-dotted/semi-solid line; SEQ ID NO: 33) and His-tag (underlined with dotted line; SEQ ID NO: 135).
SEQ ID NO: 142 Fusion protein of SMAP-29 (underlined with solid line; SEQ ID NO: 76), modified KZ144 without N-terminal methionine and with T82I, A206N, S232T, I122M; A160T C14S and C50S (underlined with semi-dotted/semi-solid line; SEQ ID NO: 49) and His-tag (underlined with dotted line; SEQ ID NO: 135).
SEQ ID NO: 151 Fusion protein of SMAP-29 (underlined with solid line; SEQ ID NO: 76), KZ144 without N-terminal methionine (underlined with semi-dotted/semi-solid line; SEQ ID NO: 2) and His-tag (underlined with dotted line; SEQ ID NO: 135).

In a first aspect the present invention relates to a polypeptide comprising an amino acid sequence exhibiting at least about 90% sequence identity with the sequence of SEQ ID NO: 1, wherein SEQ ID NO: 1 is characterized by
X1 may be absent or any amino acid, in particular M,
X14 may be any amino acid, preferably S, R or N, more preferably S or R
X23 may be any amino acid, preferably S, R or N, more preferably S
X50 may be any amino acid, preferably S, R or N, more preferably S or N
X82 may be any amino acid, preferably T or I
X122 may be any amino acid, preferably I or M
X149 may be any amino acid, preferably M or P
X154 may be any amino acid, preferably L or T
X160 may be any amino acid, preferably A or T
X167 may be any amino acid, preferably I or L
X179 may be any amino acid, preferably N or F
X180 may be any amino acid, preferably M or E
X186 may be any amino acid, preferably V or Y
X206 may be any amino acid, preferably A, N or V
X212 may be any amino acid, preferably T or N
X224 may be any amino acid, preferably P or Q
X230 may be any amino acid, preferably N or Y
X232 may be any amino acid, preferably S or T;
and wherein the polypeptide does neither comprise the amino acid sequence of SEQ ID NO: 2, nor of SEQ ID NO: 3, nor of SEQ ID NO: 4.

The term "polypeptide" as used herein refers in particular to a polymer of amino acid residues linked by peptide bonds in a specific sequence. The amino acid residues of a polypeptide may be modified by e.g. covalent attachments of various groups such as carbohydrates and phosphate. Other substances may be more loosely associated with the polypeptide, such as heme or lipid, giving rise to conjugated polypeptides which are also comprised by the term "polypeptide" as used herein. The term as used herein is intended to encompass also proteins. Thus, the term "polypeptide" also encompasses for example complexes of two or more amino acid polymer chains. The term "polypeptide" does encompass embodiments of polypeptides which exhibit optionally modifications typically used in the art, e.g. biotinylation, acetylation, pegylation, chemical changes of the amino-, SH- or carboxyl-groups (e.g. protecting groups) etc. As will become apparent from the description below, the polypeptide according to the present invention may also be a fusion protein, i.e. linkage of at least two amino acid sequences which do not occur in this combination in nature. The term "polypeptide" as used herein is not limited to a specific length of the amino acid polymer chain, but typically the polypeptide will exhibit a length of more than about 50 amino acids, more than about 100 amino acids or even more than about 150 amino acids. Usually, but not necessarily, a typical polypeptide of the present invention will not exceed about 750 amino acids in length.

As used herein, the term "% sequence identity", has to be understood as follows: Two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted. Methods for comparing the identity and homology of two or more sequences are well known in the art. The percentage to which two sequences are identical can for example be determined by using a mathematical algorithm. A preferred, but not limiting, example of a mathematical algorithm which can be used is the algorithm of Karlin et a/. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul et al. (1997), Nucleic Acids Res, 25:3389-3402), accessible through the home page of the NCBI at world wide web site ncbi.nlm.nih.gov) and FASTA (Pearson (1990), Methods Enzymol. 83, 63-98; Pearson and Lipman (1988), Proc. Natl. Acad. Sci. U.S.A 85, 2444-2448). Sequences which are identical to other sequences to a certain extent can be identified by these programmes. Furthermore, programs available in the Wisconsin Sequence Analysis Package, version 9.1 (Devereux et al, 1984, Nucleic Acids Res., 387-395), for example the programs BESTFIT and GAP, may be used to determine the % identity between two polypeptide sequences. BESTFIT uses the "local homology" algorithm of (Smith and Waterman (1981), J. Mol. Biol. 147, 195-197.) and finds the best single region of similarity between two sequences. If herein reference is made to an amino acid sequence sharing a particular extent of sequence identity to a reference sequence, then said difference in sequence is preferably due to conservative amino acid substitutions. Preferably, such sequence retains the activity of the reference sequence, e.g. albeit maybe at a slower rate. In addition, if reference is made herein to a sequence sharing "at least" at certain percentage of sequence identity, then 100% sequence identity are preferably not encompassed.

"Conservative amino acid substitutions", as used herein, may occur within a group of amino acids which have sufficiently similar physicochemical properties, so that a substitution between members of the group will preserve the biological activity of the molecule (see e.g. Grantham, R. (1974), Science 185, 862-864). Particularly, conservative amino acid substitutions are preferably substitutions in which the amino acids originate from the same class of amino acids (e.g. basic amino acids, acidic amino acids, polar amino acids, amino acids with aliphatic side chains, amino acids with positively or negatively charged side chains, amino acids with aromatic groups in the side chains, amino acids the side chains of which can enter into hydrogen bridges, e.g. side chains which have a hydroxyl function, etc.). Conservative substitutions are in the present case for example substituting a basic amino acid residue (Lys, Arg, His) for another basic amino acid residue (Lys, Arg, His), substituting an aliphatic amino acid residue (Gly, Ala, Val, Leu, Iie) for another aliphatic amino acid residue, substituting an aromatic amino acid residue (Phe, Tyr, Trp) for another aromatic amino acid residue, substituting threonine by serine or leucine by isoleucine. Further conservative amino acid exchanges will be known to the person skilled in the art.

The term "deletion" as used herein refers preferably to the absence of 1, 2, 3, 4, 5 (or even more than 5) continuous amino acid residues in the derivative sequence in comparison to the respective reference sequence, either intrasequentially or at the N- or C-terminus.

The term "insertion" as used herein refers preferably to the additional intrasequential presence of 1, 2, 3, 4, 5 (or even more than 5) continuous amino acid residues in the derivative sequence in comparison to the respective reference sequence.

The term "addition" as used herein refers preferably to the additional presence of 1, 2, 3, 4, 5 (or even more than 5) continuous amino acid residues at the N- and/or C-terminus of the derivative sequence in comparison to the respective reference sequence.

The term "substitution" as used herein refers to the presence of an amino acid residue at a certain position of the derivative sequence which is different from the amino acid residue which is present or absent at the corresponding position in the reference sequence. As mentioned above, preferably such substitutions are conservative substitutions.

The term "cell wall" as used herein refers to all components that form the outer cell enclosure of Gram-negative bacteria and thus guarantee their integrity. In particular, the term "cell wall" as used herein refers to peptidoglycan, the outer membrane of the Gram-negative bacteria with the lipopolysaccharide, the bacterial cell membrane, but also to additional layers deposited on the peptidoglycan as e.g. capsules, outer protein layers or slimes.

The term "amino acid sequence stretch" as used herein refers to a particular stretch of amino acid sequence in the amino acid sequence of the polypeptide of the invention. Said sequence refers to a sequence of a cationic peptide, a polycationic peptide, an amphiphatic peptide, a hydrophobic peptide, a sushi peptide and/or an antimicrobial peptide. The term does not refer to conventional tags like His-tags, such as His5-tags, His6-tags, His7-tags, His8-tags, His9-tags, His10-tags, His11-tags, His12-tags, His16-tags and His20-tags, Strep-tags, Avi-tags, Myc-tags, Gst-tags, JS-tags, cystein-tags, FLAG-tags or other tags known in the art, thioredoxin or maltose binding proteins (MBP). Preferably an amino acid sequence stretch as used herein as a length of about 6 to about 39 amino acid residues.

As used herein, the term "cationic peptide" refers preferably to a peptide having positively charged amino acid residues. Preferably a cationic peptide has a pKa-value of 9.0 or greater. Typically, at least four of the amino acid residues of the cationic peptide can be positively charged, for example, lysine or arginine. "Positively charged" refers to the side chains of the amino acid residues which have a net positive charge at about physiological conditions. The term "cationic peptide" as used herein refers also to polycationic peptides, but also includes cationic peptides which comprise for example less than 20%, preferably less than 10% positively charged amino acid residues.

The term "polycationic peptide" as used herein refers preferably to a peptide composed of mostly positively charged amino acid residues, in particular lysine and/or arginine residues. A peptide is composed of mostly positively charged amino acid residues if at least about 20, 30, 40, 50, 60, 70, 75, 80, 85, 90, 95 or about 100% of the amino acid residues are positively charged amino acid residues, in particular lysine and/or arginine residues. The amino acid residues being not positively charged amino acid residues can be neutrally charged amino acid residues and/or negatively charged amino acid residues and/or hydrophobic amino acid residues. Preferably the amino acid residues being not positively charged amino acid residues are neutrally charged amino acid residues, in particular serine and/or glycine.

The term, "antimicrobial peptide" (AMP) as used herein refers preferably to any naturally occurring peptide that has microbicidal and/or microbistatic activity on for example bacteria, viruses, fungi, yeasts, mycoplasma and protozoa. Thus, the term "antimicrobial peptide" as used herein refers in particular to any peptide having anti-bacterial, anti-fungal, anti-mycotic, anti-parasitic, anti-protozoal, anti-viral, anti-infectious, anti-infective and/or germicidal, algicidal, amoebicidal, microbicidal, bactericidal, fungicidal, parasiticidal, protozoacidal, protozoicidal properties. Preferred are anti-bacterial peptides. The antimicrobial peptide may be a member of the RNase A super family, a defensin, cathelicidin, granulysin, histatin, psoriasin, dermicidine or hepcidin. The antimicrobial peptide may be naturally occurring in insects, fish, plants, arachnids, vertebrates or mammals. Preferably the antimicrobial peptide may be naturally occurring in insects, fish, plants, arachnids, vertebrates or mammals. Preferably the antimicrobial peptide may be naturally occurring in radish, silk moth, wolf spider, frog, preferably in *Xenopus laevis, Rana* frogs, more preferably in *Rana catesbeiana*, toad, preferably Asian toad *Bufo bufo gargarizans*, fly, preferably in *Drosophila*, more preferably in *Drosophila melanogaster*, in *Aedes aegypti*, in honey bee, bumblebee, preferably in *Bombus pascuorum*, flesh fly, preferably in *Sarcophaga peregrine*, scorpion, horseshoe crab, catfish, preferably in *Parasilurus asotus*, cow, pig, sheep, porcine, bovine, monkey and human. As used herein, an "antimicrobial peptide" (AMP) may in particular be a peptide which is not a cationic peptide, polycationic peptide, amphiphatic peptide, sushi peptide, defensins, and hydrophobic peptide, but nevertheless exhibits antimicrobial activity.

The term "sushi peptide" as used herein refers to complement control proteins (CCP) having short consensus repeats. The sushi module of sushi peptides functions as a protein-protein interaction domain in many different proteins. Peptides containing a Sushi domain have been shown to have antimicrobial activities. Preferably, sushi peptides are naturally occurring peptides.

The term "amphiphatic peptide" as used herein refers to synthetic peptides having both hydrophilic and hydrophobic functional groups. Preferably, the term "amphiphatic peptide" as used herein refers to a peptide having a defined arrangement of hydrophilic and hydrophobic groups e.g. amphiphatic peptides may be e.g. alpha helical, having predominantly non polar side chains along one side of the helix and polar residues along the rest of its surface.

The term "hydrophobic group" as used herein refers preferably to chemical groups such as amino acid side chains which are substantially water insoluble, but soluble in an oil phase, with the solubility in the oil phase being higher than that in water or in an aqueous phase. In water, amino acid residues having a hydrophobic side chain interact with one another to generate a non-aqueous environment. Examples of amino acid residues with hydrophobic side chains are valine, isoleucine, leucine, methionine, phenylalanine, tryptophan, cysteine, alanine, tyrosine, and proline residues The term "hydrophobic peptide" as used herein refers to a hydrophobic peptide, which is preferably composed of mostly amino acid residues with hydrophobic groups. Such peptide is preferably composed of mostly hydrophobic amino acid residues, i.e. at least about 20, 30, 40, 50, 60, 70, 75, 80, 85, 90, 95 or at least about 100% of the amino acid residues are hydrophobic amino acid residues. The amino acid residues being not hydrophobic are preferably neutral and preferably not hydrophilic.

As used herein, the term "tag" refers to an amino acid sequence, which is typically in the art fused to or included in another amino acid sequence for a) improving expression of the overall amino acid sequence or polypeptide, b) facilitating purification of the overall amino acid sequence or polypeptide, c) facilitating immobilisation of the overall amino acid sequence or polypeptide, and/or d) facilitating detection of the overall amino acid sequence or polypeptide. Examples for tags are His tags, such as His5-tags, His6-tags, His7-tags, His8-tags, His9-tags, His10-tags, His11-tags, His12-tags, His16-tags and His20-tags, Strep-tags, Avi-tags, Myc-tags, GST-tags, JS-tags, cystein-tags, FLAG-tags, HA-tags, thioredoxin or maltose binding proteins (MBP), CAT, GFP, YFP, etc. The person skilled in the art will know a vast number of tags suitable for different technical applications. The tag may for example make such tagged polypeptide suitable for e.g. antibody binding in different ELISA assay formats or other technical applications.

The term "comprising" as used herein shall not be construed as being limited to the meaning "consisting of" (i.e. excluding the presence of additional other matter). Rather, "comprising" implies that optionally additional matter may be present. The term "comprising" encompasses as particularly envisioned embodiments falling within its scope "consisting of" (i.e. excluding the presence of additional other matter) and "comprising but not consisting of" (i.e. requiring the presence of additional other matter), with the former being more preferred.

The polypeptide according to the present invention may exhibit in the amino acid sequence exhibiting at least about 90% sequence identity with the sequence of SEQ ID NO: 1 at least one (e.g. 1, 2, 3, 4, 5, 6, 7, 8, 9, 10, 11, 12, 13, 14, 15, 16 or even all 17) of the following: X14 is not C; X23 is not C; X50 is not C; X82 is I; X122 is M; X149 is P; X154 is T, X160 is T; X167 is L; X179 is F; X180 is E; X186 is Y; X206 is N or V, X212 is N; X224 is Q; X230 is Y and/or X232 is T. It is understood that the number indicating the position of the respective amino acid residue indicates the relative position in the sequence corresponding to SEQ ID NO: 1, and not to the overall amino acid sequence of the polypeptide according to the present invention, which may be longer.

The inventive polypeptide exhibits said at least 90% sequence identity. The inventive polypeptide may thus for example exhibit a higher level of sequence identity, e.g. may exhibit at least about 95%, at least about 96%, at least about 97%, at least about 98%, at least about 98.5%, at least about 99% (e.g. less than 3 amino acids deviation), at least about 99.3% (e.g. less than 2 amino acids deviation), at least about 99.5%, at least about 99.6% or even 100% sequence identity with the sequence of SEQ ID NO: 1.

An inventive polypeptide comprising a sequence sharing a given level of sequence identity with the sequence of SEQ ID NO: 1 (or more specific sequences thereof, see below) can for example deviate from the reference sequence by addition, substitution, insertion or deletion of one or more amino acid residues and all possible combinations thereof. Only for the sake of clarity it is pointed out that such combinations refer to distinct positions in the sequence. A "deletion" followed by "addition", or "addition" followed by "deletion", of one or more amino acids, at the same relative position, is not an combination of an "addition" and "deletion" (or vice versa) but falls under the term "substitution". Preferably, the deviations in sequence from the sequence of SEQ ID NO: 1 (or more specific sequences thereof, see below) will be of conservative nature, e.g. conservative substitutions. Even more preferably the deviation in sequence is limited to those positions in SEQ ID NO: 1 (or more specific sequences thereof, see below) which have been identified to be non-critical for the enzymatic activity, i.e. X1, X14, X23, X50, X82, X122, X149; X160, X167, X179, X180, X186; X206; X212; X224; X230 and/or X232.

Preferably, the polypeptide according to the present invention exhibits in the amino acid sequence exhibiting at least about 90% sequence identity with the sequence of SEQ ID NO: 1 a glutamic acid residue at position 115. As shown in the publication Briers et al. (Molecular Microbiology (2007) 65(5), 1334-1344), the mutation E115A led to a loss in activity of about 70% of the enzyme. Thus, while an inventive polypeptide comprising said mutation will thus not be a loss of function polypeptide and may still serve various technical purposes, it is certainly preferred if such mutation is not present in the sequence stretch corresponding to SEQ ID NO: 1 within the inventive polypeptide.

In a particular preferred embodiment according to the present invention the polypeptide of the present invention comprises the sequence of SEQ ID NO: 1.

The inventors of the present invention have found out that three cysteine residues in the amino acid sequence of SEQ ID NO: 5 (KZ144 endolysin sequence) are not essential for the enzymatic activity. Thus, in the sequence corresponding to SEQ ID NO: 1 (consensus sequence of the present invention) of the inventive polypeptide (or sharing at least 90% sequence identity therewith), in some embodiments X14 is not C, X23 is not C, or X50 is not C. Combinations are possible, e.g. X14 and X23 are not C, X14 and X50 are not C, or X23 and X50 are not C. Likewise, it is also possible that neither X14 nor X23 nor X50 are C. In principle said amino acid residues can be deleted or substituted by any other amino acid. Examples for such other amino acids are S, R and N. Thus, X14 may for example be S, N, or R; more preferably S or R; most preferably R; X23 may for example be S, N, or R, more preferably S; and X50 may for example be S, N, or R, more preferably S or N; most preferably N. X14, X23 and X50 may of course exhibit different amino acid substitutions, for example X14 may be R while X23 and X50 are S; or X14 and X23 are S, while X50 is N; X14 may be R while X23 is S and X50 is N etc. Any other combination conceivable is also contemplated by the present invention. Conservative amino acid substitutions are preferred. Particularly preferred is a substitute of a serine residue for the cysteine residue. Thus, in particularly preferred examples of the present invention X14 is S, X23 is S or X50 is S. Of course, it is also possible that X14 and X23 are S, or that X14 and X50 are S, or that X23 and X50 are S. X14, X23 and X50 may also all three be S. Absence of one or more or even of all of these cysteine residue has the advantage that the risk of aggregation of the polypeptide according to the present invention, e.g. by undesired disulfide bridge formation, is reduced, and is thus an preferred embodiment of the present invention.

Aside of the dispensability of the above referenced cysteine residues, the inventors of the present invention have also elucidated that various other residues in the sequence of SEQ ID NO: 5 are also not essential and, moreover, may be replaced by other residues, thereby increasing for instance the temperature stability of the inventive polypeptide. Examples for such substitutions are X82I, X122M, X149P; X154T, X160T, X167L, X179F, X180E, X186Y, X206V, X206N, X212N, X230Y and X232T. These substitutions may be present alone or in any combination. A typical combination is the combination of X122M and X160T. Other examples of combinations are, without being limited thereto, X82I, X206V plus X232T; X82I, X122M, X160T, X206V, plus X232T; X82I, X122M, X160T, X206N, plus X232T; X82I, X122M, X206V, plus X232T; X82I, X122M, X149P, X160T, X206V, plus X232T; X82I, X122M, X160T, X180E, X206V, plus X232T; X82I, X122M, X160T, X186Y, X206V, plus X232T; X82I, X122M, X160T, X206V, X230Y, plus X232T; X82I, X122M, X149P, X206V, plus X232T; X82I, X122M, X149P, X160T, X206V, plus X232T; X82I, X122M, X149P, X206V, plus X232T; X82I, X122M, X149P, X167L, X206V, plus X232T; X82I, X122M, X149P, X179F, X206V, plus X232T; X82I, X122M, X149P, X206V, X212N plus X232T; X82I, X122M, X149P, X206V, X224Q plus X232T; X82I, X122M, X149P, X154T, X206V, plus X232T etc. Of course, this second type of amino acid modifications may be combined with the above mentioned cysteine replacements in any type of combination conceivable. Examples of such combinations are, without being limited thereto, X14S, X50S, X122M and X160T; X14S, X50S, X82I, X122M, X160T, X206V, and X232T; X14S, X50S, X82I, X122M, X160T, X206N, and X232T; X14S, X50S, X82I, X122M, X206V, and X232T; X14S, X50S, X82I, X122M, X149P, X160T, X206V, and X232T; X14S, X50S, X82I, X122M, X160T, X180E, X206V, and X232T; X14S, X50S, X82I, X122M, X160T, X186Y, X206V, and X232T; X14S, X50S, X82I, X122M, X160T, X206V, X230Y, and X232T; X14R, X50S, X82I, X122M, X160T, X206V, and X232T; X14S, X50N, X82I, X122M, X160T, X206V, and X232T; X14R, X50S, X82I, X122M, X149P, X206V, and X232T; X14R, X50S, X82I, X122M, X149P, X160T, X206V, and X232T; X14R, X50N, X82I, X122M, X149P, X206V, and X232T; X14R, X50N, X82I, X122M, X149P, X167L, X206V, and X232T; X14R, X50N, X82I, X122M, X149P, X179F, X206V, and X232T; X14R, X50N, X82I, X122M, X149P, X206V, X212N, and X232T; X14R, X50N, X82I, X122M, X149P, X206V, X224Q and X232T; X14R, X50N, X82I, X122M, X149P, X154T, X206V, and X232T; etc.

In SEQ ID NO: 1 (consensus sequence of the present invention) the first amino acid residue is indicated as being either absent or any amino acid, in particular M. The results of the inventors, and of previous work (see WO 2010/149792) show, that the N-terminal methionine of KZ144 is dispensable. Thus, in some embodiments of the present invention the position of X1 in the sequence corresponding to SEQ ID NO: 1 in the inventive polypeptide is not M. If the polypeptide of the present invention exhibits for example N-terminally of the sequence corresponding to SEQ ID NO: 1 further sequence elements, it may for instance for the purpose of effective expression in a host cell be useful, if the methionine at position 1 of SEQ ID NO: 1 is eliminated or replaced by another amino acid in order to avoid a starting codon in the corresponding nucleic acid sequence, potentially leading to parallel expression of a polypeptide lacking the further sequence elements located more N-terminally. On the other hand, if there are no further N-terminal sequence elements in the inventive polypeptide, X1 is of course preferably methionine (e.g. for expression purposes). For the enzymatic activity X1 is however never required.

Sequences falling under the definition of SEQ ID NO: 1, which have been particularly tested by the inventors, are for instance SEQ ID NOs: 6-27 (and corresponding sequences without N-terminal methionine, SEQ ID NOs: 28-49).

It is understood that everything which has been set forth so far in terms of the generic sequence SEQ ID NO: 1 applies in similar manner also to more specific sequences. Thus, and only for the sake of clarity it is pointed out, that a polypeptide according to the present invention, comprising a sequence exhibiting at least 90% sequence identity with the generic sequence of SEQ ID NO: 1 as set out above, may in preferred embodiments certainly exhibit in analogous manner at least 90% sequence identity with more specific sequences of SEQ ID NO: 1 described or even particularly disclosed herein. Thus, in preferred embodiments of the present invention, the polypeptide of the present invention may for example comprise a sequence exhibiting at least 90% sequence identity with a sequence selected from any of SEQ ID NOs: 6-49, wherein the polypeptide does neither comprise the amino acid sequence of SEQ ID NO: 2, nor of SEQ ID NO: 3, nor of SEQ ID NO: 4.

The polypeptide according to the present invention may comprise aside of the enzymatic amino acid sequence, e.g. the sequence exhibiting at least about 90% sequence identity with the sequence of SEQ ID NO: 1 (or other sequences falling under these definition), further amino acid sequence stretches, e.g. as already disclosed in similar fashion in WO 2010/149792. The polypeptide according to the present invention may for example comprise additionally at least one amino acid sequence stretch selected from the group consisting of amphiphatic peptide, cationic peptide, polycationic peptide, hydrophobic peptide, or naturally occurring antimicrobial peptide, like sushi peptide and defensin. Such additional amino acid sequence stretches may improve the antibacterial properties of the inventive polypeptide. In some embodiments, the inventive polypeptide may comprise at least two distinct amino acid sequence stretches selected from the group of amphiphatic peptide, cationic peptide, polycationic peptide, hydrophobic peptide, or naturally occurring antimicrobial peptide, like sushi peptide and defensin.

These one or more additional amino acid sequence stretches may be present N-terminally or C-terminally of the sequence exhibiting at least about 90% sequence identity with the sequence of SEQ ID NO: 1. They may for example be located at the N- or C-terminus of the inventive polypeptide. Preferred examples of such additional amino acid sequence stretches (without being limited thereto), are the sequence KRK and SEQ ID NOs: 50-120, as set out in more detail below. The polypeptide according to the present invention may comprise at least one additional amino acid sequence stretch selected from this group. For further guidance, in particular with respect to the generic and specific nature of possible additional amino acid sequence stretches, see for example also WO 2010/023207, WO 2010/149792, WO 2010/149795 and WO 2012/085259.

Examples for cationic and polycationic amino acid sequence stretches are listed in the following table.

TABLE 1

| amino acid sequence stretch | length | SEQ ID NO: |
|---|---|---|
| KRKKRK | 6 | SEQ ID NO: 50 |
| KRXKR | 5 | SEQ ID NO: 51 |
| KRSKR | 5 | SEQ ID NO: 52 |
| KRGSG | 5 | SEQ ID NO: 53 |
| KRKKRKKRK | 9 | SEQ ID NO: 54 |
| RRRRRRRRR | 9 | SEQ ID NO: 55 |
| KKKKKKKK | 8 | SEQ ID NO: 56 |
| KRKKRKKRKK | 10 | SEQ ID NO: 57 |
| KRKKRKKRKKRK | 12 | SEQ ID NO: 58 |
| KRKKRKKRKKRKKR | 14 | SEQ ID NO: 59 |

TABLE 1-continued

| amino acid sequence stretch | length | SEQ ID NO: |
|---|---|---|
| KKKKKKKKKKKKKKKK | 16 | SEQ ID NO: 60 |
| KRKKRKKRKKRKKRKKRK | 18 | SEQ ID NO: 61 |
| KRKKRKKRKKRKKRKKRKK | 19 | SEQ ID NO: 62 |
| RRRRRRRRRRRRRRRRRRR | 19 | SEQ ID NO: 63 |
| KKKKKKKKKKKKKKKKKKK | 19 | SEQ ID NO: 64 |
| KRKKRKKRKRSKRKKRKKRK | 20 | SEQ ID NO: 65 |
| KRKKRKKRKRSKRKKRKKRKK | 21 | SEQ ID NO: 66 |
| KRKKRKKRKRKRKKRKKRKKRK | 21 | SEQ ID NO: 67 |
| KRKKRKKRKRGSGKRKKRKKRK | 22 | SEQ ID NO: 68 |
| KRKKRKKRKRGSGSGKRKKRKKRK | 24 | SEQ ID NO: 69 |
| KRKKRKKRKRKRKKRKRKKRKKRKK | 25 | SEQ ID NO: 70 |
| KRKKRKKRKRSKRKKRKKRKRSKRKKRKKRK | 31 | SEQ ID NO: 71 |
| KRKKRKKRKRGSGSGKRKKRKKRKGSGSGKRKKRKKRK | 38 | SEQ ID NO: 72 |
| KRKKRKKRKRKRKKRKKRKRKRKKRKKRKKRKRKKRKKRK | 39 | SEQ ID NO: 73 |
| KRKKRKKRKRSKRKKRKKRKRSKRKKRKKRKRSKRKKRKKRK | 42 | SEQ ID NO: 74 |

Examples for antimicrobial amino acid sequences which may be used in carrying out the present invention are listed in the following table.

TABLE 2

| Peptide | Sequence | SEQ ID NO |
|---|---|---|
| LL-37 | LLGDFFRKSKEKIGKEFKRIVQRIKDFLRNLVPRTES | SEQ ID NO: 75 |
| SMAP-29 | RGLRRLGRKIAHGVKKYGPTVLRIIRIAG | SEQ ID NO: 76 |
| Indolicidin | ILPWKWPWWPWRR | SEQ ID NO: 77 |
| Protegrin | RGGRLCYCRRRFCVCVGR | SEQ ID NO: 78 |
| Cecropin P1 | SWLSKTAKKLENSAKKRISEGIAIAIQGGPR | SEQ ID NO: 79 |
| Magainin | GIGKFLHSAKKFGKAFVGEIMNS | SEQ ID NO: 80 |
| Pleurocidin | GWGSFFKKAAHVGKHVGKAALTHYL | SEQ ID NO: 81 |
| Cecropin A (A.aegypti) | GGLKKLGKKLEGAGKRVFNAAEKALPVVAGAKALRK | SEQ ID NO: 82 |
| Cecropin A (D. melanogaster) | GWLKKIGKKIERVGQHTRDATIQGLGIPQQAANVAATARG | SEQ ID NO: 83 |
| Buforin II | TRSSRAGLQFPVGRVHRLLRK | SEQ ID NO: 84 |
| Sarcotoxin IA | GWLKKIGKKIERVGQHTRDATIQGLGIAQQAANVAATAR | SEQ ID NO: 85 |
| Apidaecin | ANRPVYIPPPRPPHPRL | SEQ ID NO: 86 |
| Ascaphine 5 | GIKDWIKGAAKKLIKTVASHIANQ | SEQ ID NO: 87 |
| Nigrocine 2 | GLLSKVLGVGKKVLCGVSGLVC | SEQ ID NO: 88 |
| Pseudin 1 | GLNTLKKVFQGLHEAIKLINNHVQ | SEQ ID NO: 89 |
| Ranalexin | FLGGLIVPAMICAVTKKC | SEQ ID NO: 90 |
| Melittin | GIGAVLKVLTTGLPALISWIKRKRQQ | SEQ ID NO: 91 |

TABLE 2-continued

| Peptide | Sequence | SEQ ID NO |
|---|---|---|
| Lycotoxin 1 | IWLTALKFLGKHAAKKLAKQQLSKL | SEQ ID NO: 92 |
| Parasin 1 | KGRGKQGGKVRAKAKTRSS | SEQ ID NO: 93 |
| Buforin I | AGRGKQGGKVRAKAKTRSSRAGLQFPVGRVHRLLRKGNY | SEQ ID NO: 94 |
| Dermaseptin 1 | ALWKTMLKKLGTMALHAGKAALGAAADTISQGTQ | SEQ ID NO: 95 |
| Bactenecin 1 | RLCRIVVIRVCR | SEQ ID NO: 96 |
| Thanatin | GSKKPVPIIYCNRRTGKCQRM | SEQ ID NO: 97 |
| Brevinin 1T | VNPIILGVLPKVCLITKKC | SEQ ID NO: 98 |
| Ranateurin 1 | SMLSVLKNLGKVGLGFVACKINIKQC | SEQ ID NO: 99 |
| Esculentin 1 | GIFSKLGRKKIKNLLISGLKNVGKEVGMDVVRTGIKIAGCKIKGEC | SEQ ID NO: 100 |
| Tachyplesin | RWCFRVCYRGICYRKCR | SEQ ID NO: 101 |
| Androctonin | RSVCRQIKICRRGGCYYKCTNRPY | SEQ ID NO: 102 |
| alpha-defensin | DCYCRIPACIAGERRYGTCIYQGRLWAFCC | SEQ ID NO: 103 |
| beta-defensin | NPVSCVRNKGICVPIRCPGSMKQIGTCVGRAVKCCRKK | SEQ ID NO: 104 |
| theta-defensin | GFCRCLCRRGVCRCICTR | SEQ ID NO: 105 |
| defensin (sapecin A) | ATCDLLSGTGINHSACAAHCLLRGNRGGYCNGKAVCVCRN | SEQ ID NO: 106 |
| Thionin (crambin) | TTCCPSIVARSNFNVCRIPGTPEAICATYTGCIIIPGATCPGDYAN | SEQ ID NO: 107 |
| defensin from radish | QKLCQRPSGTWSGVCGNNNACKNQCIRLEKARHGSCNYVFPAHCICYFPC | SEQ ID NO: 108 |
| Drosomycin | DCLSGRYKGPCAVWDNETCRRVCKEEGRSSGHCSPSLKCWCEGC | SEQ ID NO: 109 |
| Hepcidin | DTHFPICIFCCGCCHRSKCGMCCKT | SEQ ID NO: 110 |
| Bac 5 | RFRPPIRRPPIRPPFYPPFRPPIRPPIFPPIRPPFRPPLGRPFP | SEQ ID NO: 111 |
| PR 39 | RRRPRPPYLPRPRPPPFFPPRLPPRIPPGFPPRFPPRFP | SEQ ID NO: 112 |
| Pyrrhocoricin | VDKGSYLPRPTPPRPIYNRN | SEQ ID NO: 113 |
| Histatin 5 | DSHAKRHHGYKRKFHEKHHSHRGY | SEQ ID NO: 114 |

The at least one additional amino acid sequence stretch may be a sushi peptide which is described by Ding J L, Li P, Ho B Cell Mol Life Sci. 2008 April; 65(7-8):1202-19. The Sushi peptides: structural characterization and mode of action against Gram-negative bacteria. Especially preferred is the sushi 1 peptide according to SEQ ID NO: 115. Other preferred sushi peptides are sushi peptides S1 and S3 and multiples thereof; FASEB J. 2000 September; 14(12):1801-13.

Preferred hydrophobic peptides are Walmagh1 having the amino acid sequence according to SEQ ID NO: 116 and the hydrophobic peptide having the amino acid sequence Phe-Phe-Val-Ala-Pro (SEQ ID NO: 117).

Preferred amphiphatic peptides are α4-helix of T4 lysozyme according to SEQ ID NO: 118 and WLBU2-Variant having the amino acid sequence according to SEQ ID NO: 119 and Walmagh 2 according to SEQ ID NO: 120.

As mentioned above, a polypeptide according to the present invention may comprise at least one additional amino acid sequence stretch selected from the group consisting of: KRK and SEQ ID NOs: 50-120. Corresponding examples are for instance polypeptides comprising a sequence selected from the group consisting of SEQ ID NOs: 121-127 (and corresponding sequences without N-terminal methionine, SEQ ID NOs: 128-134.

A polypeptide according to the present invention comprises an amino acid sequence exhibiting at least about 90% sequence identity with the sequence of SEQ ID NO: 1, wherein the polypeptide does neither comprise the amino acid sequence of SEQ ID NO: 2, nor of SEQ ID NO: 3, nor of SEQ ID NO: 4. Thus, a polypeptide of the present invention may also comprise an amino acid sequence exhibiting at least 91.5% sequence identity with an amino acid sequence selected from any of SEQ ID NOs: 121-134, wherein the polypeptide does neither comprise the amino acid sequence of SEQ ID NO: 2, nor of SEQ ID NO: 3, nor of SEQ ID NO: 4.

Such inventive polypeptide may thus for example comprise a sequence exhibiting a higher level of sequence identity than 91.5% with an amino acid sequence selected from any of SEQ ID NOs: 121-134, e.g. may exhibit at least about 95%, at least about 96%, at least about 97%, at least about 98%, at least about 98.5%, at least about 98.75%, at least about 99% (e.g. less than 3 amino acids deviation), at least about 99.5% (e.g. less than 2 amino acids deviation), at least about 99.6% or even 100% sequence identity with an amino acid sequence selected from any of SEQ ID NOs: 121-134.

In addition, and irrespective whether or not one or more additional amino acid sequence stretches as set out above are present in the inventive polypeptide, the polypeptide may comprise additionally one or more tag sequences. Such tag sequence may be present N-terminally or C-terminally of the sequence exhibiting at least about 90% sequence identity with the sequence of SEQ ID NO: 1. They may for example be located at the N- or C-terminus of the inventive polypeptide. In a preferred embodiment, the one or more tag sequence is located C-terminally of the amino acid sequence exhibiting at least 90% sequence identity with the sequence of SEQ ID NO: 1.

The one or more tag sequences may for example be linked to the amino acid sequence exhibiting at least 90% sequence identity with the sequence of SEQ ID NO: 1 directly or via a short linker of 1 to 10 amino acid residues, preferably 1 to 5 amino acid residues, even more preferably 1 to 2 amino acids. Linker sequences are preferably flexible sequences, comprising one or more glycine residues. Numerous examples for tags are known in the art, some of which have already been mentioned above. In the context of the present invention a particularly preferred tag sequence is a His-tag, preferably a His tag according to SEQ ID NO: 135.

The length of the polypeptide according to present invention is in principle not limited, but preferably the length will not be excessively large. Preferably, a polypeptide according to the present invention has an overall length not exceeding about 320 amino acids, preferably not exceeding about 310 amino acids.

Specific examples of polypeptides according to the present invention can be selected from the group consisting of SEQ ID NOs: 136-142 (and corresponding sequences without N-terminal methionine, SEQ ID NOs: 143-149).

A polypeptide according to the present invention comprises an amino acid sequence exhibiting at least about 90% sequence identity with the sequence of SEQ ID NO: 1, wherein the polypeptide does neither comprise the amino acid sequence of SEQ ID NO: 2, nor of SEQ ID NO: 3, nor of SEQ ID NO: 4. Thus, a polypeptide of the present invention may also comprise an amino acid sequence exhibiting at least 91.5% sequence identity with an amino acid sequence selected from any of SEQ ID NOs: 136-149, wherein the polypeptide does neither comprise the amino acid sequence of SEQ ID NO: 2, nor of SEQ ID NO: 3, nor of SEQ ID NO: 4.

Such inventive polypeptide may thus for example comprise a sequence exhibiting a higher level of sequence identity than 91.5% with an amino acid sequence selected from any of SEQ ID NOs: 136-149, e.g. may exhibit at least about 95%, at least about 96%, at least about 97%, at least about 98%, at least about 98.5%, at least about 99%, at least about 99.25% (e.g. less than 3 amino acids deviation), at least about 99.5% (e.g. less than 2 amino acids deviation), at least about 99.6% or even 100% sequence identity with an amino acid sequence selected from any of SEQ ID NOs: 136-149. Deviations from SEQ ID NOs: 136-149 may in particular occur in the two sequences linking the components SMAP29 peptide, modified KZ144 endolysin and His-tag.

A polypeptide according to the present invention is preferably characterized by the ability to degrade the peptidoglycan of Gram-negative bacteria, in particular of *Pseudomonas* and/or *Campylobacter* bacteria. In particular, the polypeptide according to the present invention is preferably capable of degrading the peptidoglycan of *Pseudomonas aeroginosa*, in particular *Pseudomonas aeroginosa* PAO1, *Campylobacter jejuni* and/or *Campylobacter coli*.

The peptidoglycan degrading activity on gram negative bacteria can be measured by assays well known in the art, e.g. by muralytic assays in which the outer membrane of gram negative bacteria is permeabilized or removed (e.g. with chloroform) to allow the putative enzyme access to the peptidoglycan layer. If the enzyme is active, degradation of the peptidoglycan layer will lead to a drop of turbidity, which can be measured photometrically (see for example Briers et al., *J. Biochem. Biophys Methods* 70: 531-533, (2007).

In a further aspect the present invention relates to a nucleic acid encoding a polypeptide according to the present invention. A person skilled in the art, having the degeneracy of the genetic code in mind, will be aware of means to generate such nucleic acid.

In a further aspect, the present invention relates to a vector, such as an expression or cloning vector, which comprises a nucleic acid according to the present invention.

In a further aspect, the present invention relates to a host cell comprising a polypeptide according to the present invention, a nucleic acid according to the present invention, and/or a vector according to the present invention.

In a further aspect, the present invention relates to composition comprising a polypeptide according to the present invention, a nucleic acid according to the present invention, a vector according to the present invention, and/or a host cell according to the present invention. Preferably, said composition is a pharmaceutical composition comprising a pharmaceutical acceptable diluent, excipient or carrier.

As set out above, a polypeptide according to the present invention comprises an amino acid sequence exhibiting at least about 90% sequence identity with the sequence of SEQ ID NO: 1, wherein the polypeptide does neither comprise the amino acid sequence of SEQ ID NO: 2, nor of SEQ ID NO: 3, nor of SEQ ID NO: 4. However, in a further aspect, and slightly distinct from the above mentioned polypeptides of the invention, the present invention also relates additionally to a polypeptide comprising an amino acid sequence exhibiting at least about 90% sequence identity with the sequence of SEQ ID NO: 1, wherein the polypeptide does neither comprise the amino acid sequence of SEQ ID NO: 2, nor of SEQ ID NO: 152, nor of SEQ ID NO: 4. Optionally, said polypeptide of this additional aspect does also not comprise the amino acid sequence of SEQ ID NO: 3. All embodiments and combinations disclosed above, in the examples or in the claims for the polypeptide of the invention, and respective nucleic acids, vectors, host cells and compositions, are specifically contemplated for this further aspect as well.

EXAMPLES

In the following, specific examples illustrating various embodiments and aspects of the invention are presented. However, the present invention shall not to be limited in scope by the specific embodiments described herein. Indeed, various modifications of the invention in addition to those described herein will become readily apparent to those skilled in the art from the foregoing description, accompanying figures and the examples below. All such modifications fall within the scope of the appended claims.

Example 1: Identification of Mutations Stabilizing KZ144 Endolysin

For identification of advantageous sites of modification in endolysin KZ144 (SEQ ID NO: 5), the inventors used in a first step targeted destabilization of the target protein. For this purpose an N-terminally truncated KZ144 was generated (SEQ ID NO: 150) into which sequence mutations were introduced via random mutagenesis (error-prone PCR) followed by subsequent fusion and selection with a chloramphenicol assay (CAT assay).

The protein melting temperature of promising candidates was determined by circular dichroism (CD). Changes of ellipticity for the proteins were recorded at 220 nm as a function of temperature using Jasco J-815 CD spectrometer and fitted to a simple sigmoid unfolding model using JASCO analysis software. The protein melting temperatures (Tmelt) were determined as midpoint of unfolding transition. The spectra were recorded at protein concentrations of 5.0-5.8 µM with a heating rate of 1° C./min and incubation time of 3 s in 410 µl volume in a 1 mm light path Hellma quartz cuvette. Measurements were performed in 50 mM NaPh buffer, 300 mM NaCl at pH of 7.4, 7.0, 6.2 and 5.7.

Some of the most promising candidates identified are illustrated in the following table:

TABLE 3

| AA-Substitution* | Solubility | $T_M$ | $\Delta T_M$ |
|---|---|---|---|
| — | + | 53.5 | 0 |
| S232T | + | 54.1 | +0.6 |
| A206V | + | 55.8 | +2.3 |
| T82I- | + | 54.3 | +0.8 |
| I122M | + | 56.5 | +3.0 |
| A160T | | | |

*Please note, the position indicated refers to the position in the sequence of KZ144 sequence, SEQ ID NO: 5, and not to the position in SEQ ID NO: 150.

The thus identified stabilizing mutations can and were subsequently introduced into other sequences such as full length sequences, increasing stability there as well.

In a further step serine was used in some constructs for substitution of cysteine residues C14, C23 and/or C50 (position indicated with respect to SEQ ID NO: 5; conservative substitutions). Other substituents at said positions tested were N and R.

In a further round of experiments, various combinations of mutations were tested in the context of the full length endolysin KZ144 (SEQ ID NO: 5):

TABLE 4

| AA-Substitution | # of mutations | Ø $T_M$ | Δ $T_M$* |
|---|---|---|---|
| C14S C50S T82I I122M A160T A206V S232T | 7 | 57.6 | +4.4 |
| C14S C50S T82I I122M A160T A206V N230Y S232T | 8 | 57.8 | +4.6 |
| C14S C50S T82I I122M A160T M180E A206V S232T | 8 | 57.7 | +4.5 |
| C14S C50S T82I I122M M149P A160T A206V S232T | 8 | 58.9 | +5.7 |

TABLE 4-continued

| AA-Substitution | # of mutations | Ø $T_M$ | Δ $T_M$* |
|---|---|---|---|
| C14S C50S T82I I122M A160T V186Y A206V S232T | 8 | 56.7 | +3.5 |
| C14R C50S T82I I122M A160T A206V S232T | 7 | 59.9 | +6.7 |
| C14S C50S T82I I122M T160A A206V S232T | 7 | 58.3 | +5.1 |
| C14S C50N T82I I122M A160T A206V S232T | 7 | 58.5 | +5.3 |
| C14R C50S T82I I122M M149P A160T A206V S232T | 8 | 61 | +7.9 |
| C14R C50S T82I I122M A206V S232T M149P | 7 | 61.7 | +8.5 |
| C14R C50N T82I I122M M149P A206V S232T | 7 | 62.8 | +9.6 |
| C14R C50N T82I I122M M149P A206V S232T | 8 | 63.4 | +10.2 |
| C14R C50N T82I I122M M149P A206V S232T | 8 | 62.8 | +9.6 |
| C14R C50N T82I I122M M149P A206V S232T | 8 | 61.5 | +8.3 |
| C14R C50N T82I I122M M149P A206V S232T | 8 | 60.9 | +7.7 |

*Δ TM vs. SEQ ID NO: 5

Example 2: Melting Temperature of Some Polypeptides According to the Present Invention and MIC for Selected Bacterial Strains For the construction of polypeptides according to SEQ ID NO 151 (w/o mutations) and SEQ ID NOs: 136-142 the lytic enzyme (gp144) of the *Pseudomonas aeruginosa* phage KZ was used. As peptide fusion partner SMAP-29 was chosen. SMAP-29 was found in sheep leukocytes and consists of 29 amino acids (RGLRRLGRKIAHGVKKYGPTVLRIIR-IAG; molecular weight: 3.3 kDa, SEQ ID NO: 76). It is built up of two LPS-binding sites which are connected by a central hinge.

Cloning

The nucleic acid molecules encoding the respective peptide and endolysin were constructed with a NdeI (5'-CAT ATG-3') restriction site at the 5'-end of the nucleic acid molecule and a XhoI (5'-CTC GAG-3') restriction site at the 3'-end of the nucleic acid molecule. Peptide and endolysin are connected via a BamHI (5'-GGA TCC-3').

Fusion proteins were constructed by linking at least two nucleic acid sequences using standard cloning techniques as described e.g. by Sambrook et al. 2001, Molecular Cloning: A Laboratory Manual. Therefore the nucleic acid molecule encoding the peptide stretch was cleaved in a digest with the respective restriction enzymes NdeI and BamHI. Subsequently the cleaved nucleic acids encoding the peptide stretch was ligated into the pET21 b expression vector (Novagen, Darmstadt, Germany), which was also cleaved in a digest with the respective restriction enzymes NdeI and BamHI before. Afterwards, the nucleic acid molecule encoding the endolysin was cleaved in a digest with the restriction enzyme BamHI and XhoI, so that the endolysin could be ligated into the pET21b expression vector (Novagen, Darmstadt, Germany), which was also cleaved in a digest with the respective restriction enzymes BamHI and XhoI before.

The sequence of the peptide-endolysin fusions was controlled via DNA sequencing and correct clones were transformed into *E. coli* BL21(DE3)pLysS (Novagen, Darmstadt, Germany) for protein expression.

Purification

Recombinant expression of the fusion proteins was done in E. coli BL21(DE3)pLysS cells (Novagen, Darmstadt, Germany). The cells were grown until an optical density of $OD_{600\ nm}$=0.5-0.8 was reached. Then the expression of the fusion protein was induced with 0.5 mM IPTG (isopropyl-thiogalactoside) and the expression was performed at 37° C. for 4 h.

Cells were harvested by centrifugation for 20 min at 6000 g and disrupted via sonication on ice. Soluble and insoluble fraction of the E. coli crude extract were separated by centrifugation (Sorvall, SS34, 30 min, 15000 rpm). All proteins were purified by $Ni^{2+}$ affinity chromatography (Äkta FPLC, GE Healthcare) using the C-terminal $His_6$ tag, encoded by the pET21b vector. Samples were microfiltrated (0.2 μm) before every chromatographic step.

The $Ni^{2+}$ affinity chromatography is performed in 4 subsequent steps, all at room temperature:
1. Equilibration of the Histrap FF 5 ml column (GE Healthcare) with up to 10 column volumes of Washing Buffer (20 mM imidazole, 1M NaCl and 20 mM HEPES on pH 7.4) at a flow rate of 3-5 ml/min.
2. Loading of the total lysate with wanted target protein on the Histrap FF 5 ml column at a flow rate of 3-5 ml/min.
3. Washing of the column with up to 10 column volumes of Washing Buffer to remove unbound protein.
4. Elution of bounded target protein from the column with an increasing linear gradient of 15 column volumes of Elution Buffer (500 mM imidazole, 500 mM NaCl and 20 mM HEPES on pH 7.4) to 100% at a flow rate of 3-5 ml/min.

The Hydrophobic Interaction Chromatography (HIC) is performed in 5 subsequent steps, all at room temperature:
1. Equilibration of the HiScreen Phenyl HP 5 ml column (GE Healthcare) with up to 5 column volumes of Washing Buffer (850 mM ammonium sulfate, 500 mM NaCl and 20 mM HEPES on pH 7.4) at a flow rate of 1-2 ml/min
2. Preparation of the sample (5 mg per 1 ml column volume of the protein pool from $Ni^{2+}$ affinity step) starts by first setting the protein concentration to 0.5 mg/ml by adding a predefined amount of Washing Buffer from the $Ni^{2+}$ Affinity step. Followed by adjusting the ammonium sulfate concentration by stepwise adding of a predefined amount of ammonium sulfate stock solution (3.8M) to a final concentration of approx. 850 mM.
3. Loading of the prepared sample on the HiScreen Phenyl HP 5 ml column at a flowrate of 1-2 ml/min.
4. Washing of the column with 5 column volumes of Washing Buffer to remove unbound protein.
5. Elution of the target protein from the column with a step of 40% Elution Buffer (500 mM NaCl and 20 mM HEPES on pH 7.4) at a flow rate of 1-2 ml/min. The target protein is eluted in broad peak at this step.

Buffer Change by Membrane Dialysis:

The elution pool of the HIC step is dialyzed (membrane: regenerated cellulose with MWCO: 6000-8000D) into storage buffer (500 mM NaCl and 20 mM HEPES; pH7.4) at 4° C. Dialysis factor is 160-250.

Characterisation

Melting temperatures characterizing stability of the polypeptides according to SEQ ID NOs: 136-142 at elevated temperatures were determined by circular dichroism spectroscopy (CD) as mentioned above.

Activity of polypeptides according to SEQ ID NOs: 136-142 on P. aeroginasa, C. jejuni and C. coli was characterised by determination of minimal inhibitory concentration (MIC) on the respective strains.

Determination of the Minimal Inhibitory Concentration (MIC)

In analogy to the determination of the "Minimum inhibitory concentration (MIC)" for antibiotics, the MIC was determined as a microdilution test. The test on Campylobacter species is performed completely at microaerophilic conditions and 42° C.

The setup of the experiment is the following:

The respective overnight culture was diluted 1:10. Ps. aeruginosa was incubated at 37° C. up to OD600=0.6 (approx. $10^9$ cells/ml). Campylobacter sp. were incubated microaerophilic up to OD600=0.08 (approx. $2.5 \times 10^8$ cells/ml). The bacterial culture was diluted to a concentration of $2 \times 10^5$ to $8 \times 10^5$ colony-forming-units per ml in Mueller-Hinton-broth (not cation-adjusted Mueller-Hinton-broth) and split in the required amount of tubes.

The polypeptide of interest was added in different concentrations (determined as μg/ml final concentration in the Mueller-Hinton-broth). In case of Ps. aeruginosa EDTA was added to a final concentration of 2 mM. In case of Campylobacter sp no EDTA was used.

The mixture was incubated overnight at 37° C. for Ps. Aeruginosa and at 42° C. for Campylobacter species. Bacterial growth was visibly determined by turbidity (in comparison to negative control). The MIC was defined as the concentration in the tube where no bacterial growth was observed. Positive (without polypeptide of interest and/or EDTA) and negative control (Mueller-Hinton-broth without bacteria) were included in the experiment.

The results are summarized in the following table:

TABLE 5

| SEQ ID NO: | Mutations* | Concentration [by UV] | Tm [° C.] | MIC on PAO1p S82 [μg/ml] 500 μM EDTA | MIC on Camp. jejuni S371 [μg/ml] no EDTA | MIC on Camp. coli S344 [μg/ml] no EDTA |
|---|---|---|---|---|---|---|
| 151 | | 5.5 μM | 44.14 | 5 | 5 | 4 |
| 136 | C14S C50S | 5.2 μM | 49.07 | 5 | 5 | 4 |
| 137 | T82I A206V S232T | 5.4 μM | 45.4 | 5 | 4 | 3 |
| 138 | T82I A206V S232T I122M A160T | 5.5 μM | 47.57 | 7 | 7 | 4 |

TABLE 5-continued

| SEQ ID NO: | Mutations* | Concentration [by UV] | Tm [° C.] | MIC on PAO1p S82 [μg/ml] 500 μM EDTA | MIC on Camp. jejuni S371 [μg/ml] no EDTA | MIC on Camp. coli S344 [μg/ml] no EDTA |
|---|---|---|---|---|---|---|
| 139 | C14S C50S I122M A160T | 5.6 μM | 51.42 | 3-4 | 3 | 4 |
| 140 | C14S C23S C50S | 5.3 μM | 50.31 | 5 | 3-4 | 2 |
| 141 | T82I A206V S232T I122M A160T C14S C50S | 5.9 μM | 51.68 | 3-6 | 5-7 | 5 |
| 142 | T82I A206N S232T I122M A160T C14S C50S | 5.3 μM | 50.64 | 3 | 5-7 | 5 |

Melting temperatures measured by CD, buffer: 50 mM NaPh, pH 7.45 300 mM NaCl

Please note again, that the position indicated refers to the position in the sequence of KZ144 sequence, SEQ ID NO: 5, and not to the position of the SEQ ID NO: indicated in the table.

The mutations introduced did thus not only increase melting temperature of the polypeptides of SEQ ID NOs: 136-142 vs the polypeptide of SEQ ID NO: 151, but did also not affect activity of the polypeptide, not even the sevenfold mutation of SEQ ID NO: 141.

Example 3: Temperature Stability of the Polypeptide According to SEQ ID NO: 139 and SEQ ID NO: 141

In order to illustrate that the increased melting temperature does indeed affect temperature stability of the respective mutated polypeptides, the inventors exposed exemplarily the mutated polypeptides of SEQ ID NO: 139 and SEQ ID NO: 141 to temperatures clearly exceeding the melting temperature of the native, non-mutated reference polypeptide (SEQ ID NO: 151).

For this purpose both polypeptides were subjected to prolonged direct heating at temperatures of 51° C. and 52° C. Subsequently, an activity test was performed on *Pseudomonas aeruginosa* strain as a model system at adapted conditions.

The results are summarized in the following table:

TABLE 6

| SEQ ID NO: | Mutations | Concentration [by UV] | Heating | MIC on PAO1p S82 [μg/ml] 500 μM EDTA |
|---|---|---|---|---|
| 139 | C14S C50S I122M A160T | 5.3 μM | 0 1 min 51° C. 2 min 51° C. 2 min 52° C. | 3-4 12.5 15 17.6 |
| 141 | T82I A206V S232T I122M A160T C14S C50S | 5.45 μM | 0 1 min 51° C. 2 min 51° C. 2 min 52° C. | 3-6 8 10 12.5 |

Protein Buffer: 50 mM NaPh, pH 7.45 300 mM NaCl

As previously, the position indicated refers to the position within the sequence portion corresponding to the KZ144 sequence, SEQ ID NO: 5, and not to the position within the full-length sequence of the SEQ ID NO: indicated in the table.

The invention claimed is:

1. A polypeptide comprising the sequence of SEQ ID NO: 1, wherein SEQ ID NO: 1 is characterized by
X1 may be absent or any amino acid,
X14 may be any amino acid,
X23 may be any amino acid,
X50 may be any amino acid,
X82 may be any amino acid,
X122 may be any amino acid,
X149 may be any amino acid,
X154 may be any amino acid,
X160 may be any amino acid,
X167 may be any amino acid,
X179 may be any amino acid,
X180 may be any amino acid,
X186 may be any amino acid,
X206 may be any amino acid,
X212 may be any amino acid,
X224 may be any amino acid,
X230 may be any amino acid,
X232 may be any amino acid,
and wherein the polypeptide does neither comprise the amino acid sequence of SEQ ID NO: 2, nor SEQ ID NO:3 nor SEQ ID NO: 4, and wherein at least one residue selected from the group consisting of X14, X23 and X50 is not C.

2. The polypeptide according to claim 1, wherein the polypeptide exhibits at least one of the following:
X82 is I
X122 is M
X149 is P
X154 is T
X160 is T
X167 is L
X179 is F
X180 is E
X186 is Y
X206 is N or V
X212 is N
X224 is Q
X230 is Y and/or
X232 is T.

3. The polypeptide according to claim 1, wherein:
X14 is S, R or N,
X23 is S, R or N,
X50 is S, R or N,
X82 is T or I
X122 is I or M
X149 is M or P
X154 is L or T
X160 is A or T
X167 is I or L
X179 is N or F
X180 is M or E
X186 is V or Y
X206 is A, N or V
X212 is T or N
X224 is P or Q
X230 is N or Y
X232 is S or T.

4. The polypeptide according to claim 1, wherein at least two residues selected from the group consisting of X14, X23 and X50 is not C.

5. The polypeptide according to claim 1, wherein at least one residue selected from the group consisting of X14, X23 and X50 is S.

6. The polypeptide according to claim 1, wherein X14, X23 and X50 are S.

7. The polypeptide according to claim 1, wherein X1 is not M.

8. The polypeptide according to claim 1, wherein the polypeptide comprises a sequence selected from the group consisting of SEQ ID NOs: 6-49.

9. The polypeptide according to claim 1, wherein the polypeptide comprises at least one additional amino acid sequence stretch selected from the group consisting of: KRK and SEQ ID NOs: 50-120.

10. The polypeptide according to claim 1, wherein the polypeptide comprises at least one additional amino acid sequence stretch having the amino acid sequence of SMAP-29, SEQ ID NO: 76.

11. The polypeptide according to claim 1, wherein the polypeptide comprises a sequence selected from the group consisting of SEQ ID NOs: 121-134.

12. The polypeptide according to claim 1, wherein the polypeptide comprises a sequence selected from the group consisting of SEQ ID NOs: 136-149.

13. The polypeptide according to claim 1, wherein the polypeptide degrades the peptidoglycan of Gram-negative bacteria, in particular of *Pseudomonas* and/or *Campylobacter* bacteria.

14. The polypeptide according to claim 1, wherein the polypeptide comprises the sequence according to SEQ ID NO: 125.

15. The polypeptide of claim 1, wherein X1 is M.

16. A composition comprising the polypeptide according to claim 1.

17. The composition according to claim 16, wherein the composition is a pharmaceutical composition comprising a pharmaceutical acceptable diluent, excipient or carrier.

18. A nucleic acid encoding the polypeptide according to claim 1.

19. A vector comprising the nucleic acid according to claim 18.

20. A host cell comprising the polypeptide according to claim 1.

* * * * *

SEQUENCE LISTING

<160> NUMBER OF SEQ ID NOS: 152

<210> SEQ ID NO 1
<211> LENGTH: 260
<212> TYPE: PRT
<213> ORGANISM: Artificial
<220> FEATURE:
<223> OTHER INFORMATION: Consensus Sequence
<220> FEATURE:
<221> NAME/KEY: MISC_FEATURE

```
<222> LOCATION: (1)..(1)
<223> OTHER INFORMATION: Xaa can be any naturally occurring amino acid
      or absent; in particular it can be methionine
<220> FEATURE:
<221> NAME/KEY: MISC_FEATURE
<222> LOCATION: (14)..(14)
<223> OTHER INFORMATION: Xaa can be any naturally occurring amino acid,
      in particular serine, arginine or aspargine
<220> FEATURE:
<221> NAME/KEY: MISC_FEATURE
<222> LOCATION: (23)..(23)
<223> OTHER INFORMATION: Xaa can be any naturally occurring amino acid,
      in particular serine, arginine or aspargine
<220> FEATURE:
<221> NAME/KEY: MISC_FEATURE
<222> LOCATION: (50)..(50)
<223> OTHER INFORMATION: Xaa can be any naturally occurring amino acid,
      in particular serine, arginine or aspargine
<220> FEATURE:
<221> NAME/KEY: MISC_FEATURE
<222> LOCATION: (82)..(82)
<223> OTHER INFORMATION: Xaa can be any naturally occurring amino acid,
      in particular threonine or isoleucine
<220> FEATURE:
<221> NAME/KEY: MISC_FEATURE
<222> LOCATION: (122)..(122)
<223> OTHER INFORMATION: Xaa can be any naturally occurring amino acid,
      in particular isoleucine or methionine
<220> FEATURE:
<221> NAME/KEY: MISC_FEATURE
<222> LOCATION: (149)..(149)
<223> OTHER INFORMATION: Xaa can be any naturally occurring amino acid,
      in particular methionine or proline
<220> FEATURE:
<221> NAME/KEY: MISC_FEATURE
<222> LOCATION: (154)..(154)
<223> OTHER INFORMATION: Xaa can be any naturally occurring amino acid,
      in particular leucine or threonine
<220> FEATURE:
<221> NAME/KEY: MISC_FEATURE
<222> LOCATION: (160)..(160)
<223> OTHER INFORMATION: Xaa can be any naturally occurring amino acid,
      in particular alanine or threonine
<220> FEATURE:
<221> NAME/KEY: MISC_FEATURE
<222> LOCATION: (167)..(167)
<223> OTHER INFORMATION: Xaa can be any naturally occurring amino acid,
      in particular isoleucine or leucine
<220> FEATURE:
<221> NAME/KEY: MISC_FEATURE
<222> LOCATION: (179)..(179)
<223> OTHER INFORMATION: Xaa can be any naturally occurring amino acid,
      in particular asparagine or phenylalanine
<220> FEATURE:
<221> NAME/KEY: MISC_FEATURE
<222> LOCATION: (180)..(180)
<223> OTHER INFORMATION: Xaa can be any naturally occurring amino acid,
      in particular methionine or glutamic acid
<220> FEATURE:
<221> NAME/KEY: MISC_FEATURE
<222> LOCATION: (186)..(186)
<223> OTHER INFORMATION: Xaa can be any naturally occurring amino acid,
      in particular valine or tyrosine
<220> FEATURE:
<221> NAME/KEY: MISC_FEATURE
<222> LOCATION: (206)..(206)
<223> OTHER INFORMATION: Xaa can be any naturally occurring amino acid,
      in particular alanine, asparagine or valine
<220> FEATURE:
<221> NAME/KEY: MISC_FEATURE
<222> LOCATION: (212)..(212)
<223> OTHER INFORMATION: Xaa can be any naturally occurring amino acid,
      in particular threonine or asparagine
<220> FEATURE:
<221> NAME/KEY: MISC_FEATURE
<222> LOCATION: (224)..(224)
<223> OTHER INFORMATION: Xaa can be any naturally occurring amino acid,
      in particular proline or glutamine
<220> FEATURE:
```

<220> NAME/KEY: MISC_FEATURE
<222> LOCATION: (230)..(230)
<223> OTHER INFORMATION: Xaa can be any naturally occurring amino acid,
    in particular asparagine or tyrosine
<220> FEATURE:
<221> NAME/KEY: MISC_FEATURE
<222> LOCATION: (232)..(232)
<223> OTHER INFORMATION: Xaa can be any naturally occurring amino acid,
    in particular serine or threonine

<400> SEQUENCE: 1

```
Xaa Lys Val Leu Arg Lys Gly Asp Arg Gly Asp Glu Val Xaa Gln Leu
1               5                   10                  15

Gln Thr Leu Leu Asn Leu Xaa Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Xaa Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Xaa Ala Asn Lys Ser Arg Ala Ala Ala Thr Pro Val Met Asn Ala
        85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Xaa Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Xaa Lys Tyr Gly Val Xaa Thr Asp Pro Thr Gly Xaa
145                 150                 155                 160

Leu Arg Lys Asp Pro Arg Xaa Ser Ala Leu Met Gly Ala Glu Leu Ile
                165                 170                 175

Lys Glu Xaa Xaa Asn Ile Leu Arg Pro Xaa Leu Lys Arg Glu Pro Thr
            180                 185                 190

Asp Thr Asp Leu Tyr Leu Ala His Phe Phe Gly Pro Gly Xaa Ala Arg
        195                 200                 205

Arg Phe Leu Xaa Thr Gly Gln Asn Glu Leu Ala Ala Thr His Phe Xaa
    210                 215                 220

Lys Glu Ala Gln Ala Xaa Pro Xaa Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260
```

<210> SEQ ID NO 2
<211> LENGTH: 259
<212> TYPE: PRT
<213> ORGANISM: unknown
<220> FEATURE:
<223> OTHER INFORMATION: KZ144 endolysin without N-terminal methionine

<400> SEQUENCE: 2

```
Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30
```

```
Phe Gly Asn Asn Thr Phe Asn Gln Val Val Lys Phe Gln Lys Asp Asn
             35                  40                  45

Cys Leu Asp Ser Asp Gly Ile Val Gly Lys Asn Thr Trp Ala Glu Leu
 50                  55                  60

Phe Ser Lys Tyr Ser Pro Pro Ile Pro Tyr Lys Thr Ile Pro Met Pro
 65                  70                  75                  80

Thr Ala Asn Lys Ser Arg Ala Ala Thr Pro Val Met Asn Ala Val
                 85                  90                  95

Glu Asn Ala Thr Gly Val Arg Ser Gln Leu Leu Leu Thr Phe Ala Ser
                100                 105                 110

Ile Glu Ser Ala Phe Asp Tyr Glu Ile Lys Ala Lys Thr Ser Ser Ala
                115                 120                 125

Thr Gly Trp Phe Gln Phe Leu Thr Gly Thr Trp Lys Thr Met Ile Glu
                130                 135                 140

Asn Tyr Gly Met Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
                180                 185                 190

Thr Asp Leu Tyr Leu Ala His Phe Phe Gly Pro Gly Ala Ala Arg Arg
                195                 200                 205

Phe Leu Thr Thr Gly Gln Asn Glu Leu Ala Ala Thr His Phe Pro Lys
                210                 215                 220

Glu Ala Gln Ala Asn Pro Ser Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 3
<211> LENGTH: 259
<212> TYPE: PRT
<213> ORGANISM: Artificial sequence
<220> FEATURE:
<223> OTHER INFORMATION: KZ144 without N-terminal methionine, with
      selenomethionine instead of methionine residues
<220> FEATURE:
<221> NAME/KEY: misc_feature
<222> LOCATION: (79)..(79)
<223> OTHER INFORMATION: Xaa is selenomethionine
<220> FEATURE:
<221> NAME/KEY: misc_feature
<222> LOCATION: (93)..(93)
<223> OTHER INFORMATION: Xaa is selenomethionine
<220> FEATURE:
<221> NAME/KEY: misc_feature
<222> LOCATION: (142)..(142)
<223> OTHER INFORMATION: Xaa is selenomethionine
<220> FEATURE:
<221> NAME/KEY: misc_feature
<222> LOCATION: (148)..(148)
<223> OTHER INFORMATION: Xaa is selenomethionine
<220> FEATURE:
<221> NAME/KEY: misc_feature
<222> LOCATION: (170)..(170)
<223> OTHER INFORMATION: Xaa is selenomethionine
<220> FEATURE:
<221> NAME/KEY: misc_feature
<222> LOCATION: (179)..(179)
<223> OTHER INFORMATION: Xaa is selenomethionine
<220> FEATURE:
<221> NAME/KEY: misc_feature
<222> LOCATION: (250)..(250)
```

<223> OTHER INFORMATION: Xaa is selenomethionine

<400> SEQUENCE: 3

```
Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Cys Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Xaa Pro
65                  70                  75                  80

Thr Ala Asn Lys Ser Arg Ala Ala Ala Thr Pro Val Xaa Asn Ala Val
                85                  90                  95

Glu Asn Ala Thr Gly Val Arg Ser Gln Leu Leu Thr Phe Ala Ser
            100                 105                 110

Ile Glu Ser Ala Phe Asp Tyr Glu Ile Lys Ala Lys Thr Ser Ser Ala
            115                 120                 125

Thr Gly Trp Phe Gln Phe Leu Thr Gly Thr Trp Lys Thr Xaa Ile Glu
    130                 135                 140

Asn Tyr Gly Xaa Lys Tyr Gly Val Leu Thr Asp Pro Thr Gly Ala Leu
145                 150                 155                 160

Arg Lys Asp Pro Arg Ile Ser Ala Leu Xaa Gly Ala Glu Leu Ile Lys
                165                 170                 175

Glu Asn Xaa Asn Ile Leu Arg Pro Val Leu Lys Arg Glu Pro Thr Asp
            180                 185                 190

Thr Asp Leu Tyr Leu Ala His Phe Phe Gly Pro Gly Ala Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Ser Ile Phe Tyr Asn Lys Asp Gly Ser Pro
225                 230                 235                 240

Lys Thr Ile Gln Glu Val Tyr Asn Leu Xaa Asp Gly Lys Val Ala Ala
                245                 250                 255

His Arg Lys
```

<210> SEQ ID NO 4
<211> LENGTH: 259
<212> TYPE: PRT
<213> ORGANISM: artificial sequence
<220> FEATURE:
<223> OTHER INFORMATION: Mutated KZ144 with E115A and without n-terminal methionine
<220> FEATURE:
<221> NAME/KEY: misc
<222> LOCATION: (114)..(114)
<223> OTHER INFORMATION: mutation corresponding to position E115A in KZ144 endolysin

<400> SEQUENCE: 4

```
Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45
```

Cys Leu Asp Ser Asp Gly Ile Val Gly Lys Asn Thr Trp Ala Glu Leu
     50                  55                  60

Phe Ser Lys Tyr Ser Pro Pro Ile Pro Tyr Lys Thr Ile Pro Met Pro
 65                  70                  75                  80

Thr Ala Asn Lys Ser Arg Ala Ala Thr Pro Val Met Asn Ala Val
                 85                  90                  95

Glu Asn Ala Thr Gly Val Arg Ser Gln Leu Leu Thr Phe Ala Ser
             100                 105                 110

Ile Ala Ser Ala Phe Asp Tyr Glu Ile Lys Ala Lys Thr Ser Ser Ala
             115                 120                 125

Thr Gly Trp Phe Gln Phe Leu Thr Gly Thr Trp Lys Thr Met Ile Glu
    130                 135                 140

Asn Tyr Gly Met Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Ala Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Ser Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 5
<211> LENGTH: 260
<212> TYPE: PRT
<213> ORGANISM: unknown
<220> FEATURE:
<223> OTHER INFORMATION: phiKZgp144

<400> SEQUENCE: 5

Met Lys Val Leu Arg Lys Gly Asp Arg Gly Asp Glu Val Cys Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
            35                  40                  45

Asn Cys Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
 65                 70                  75                  80

Pro Thr Ala Asn Lys Ser Arg Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Ile Lys Ala Lys Thr Ser Ser
            115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Ala 145               150               155               160

Leu Arg Lys Asp Pro Arg Ile Ser Ala Leu Met Gly Ala Glu Leu Ile
                165               170               175

Lys Glu Asn Met Asn Ile Leu Arg Pro Val Leu Lys Arg Glu Pro Thr
                180               185               190

Asp Thr Asp Leu Tyr Leu Ala His Phe Phe Gly Pro Gly Ala Ala Arg
                195               200               205

Arg Phe Leu Thr Thr Gly Gln Asn Glu Leu Ala Ala Thr His Phe Pro
                210               215               220

Lys Glu Ala Gln Ala Asn Pro Ser Ile Phe Tyr Asn Lys Asp Gly Ser
225               230               235               240

Pro Lys Thr Ile Gln Glu Val Tyr Asn Leu Met Asp Gly Lys Val Ala
                245               250               255

Ala His Arg Lys
                260

<210> SEQ ID NO 6
<211> LENGTH: 260
<212> TYPE: PRT
<213> ORGANISM: artificial sequence
<220> FEATURE:
<223> OTHER INFORMATION: mutated KZ144 with C14S and C50S

<400> SEQUENCE: 6

Met Lys Val Leu Arg Lys Gly Asp Arg Gly Asp Glu Val Ser Gln Leu
1               5               10              15

Gln Thr Leu Leu Asn Leu Cys Gly Tyr Asp Val Gly Lys Pro Asp Gly
                20              25              30

Ile Phe Gly Asn Asn Thr Phe Asn Gln Val Val Lys Phe Gln Lys Asp
                35              40              45

Asn Ser Leu Asp Ser Asp Gly Ile Val Gly Lys Asn Thr Trp Ala Glu
50              55              60

Leu Phe Ser Lys Tyr Ser Pro Pro Ile Pro Tyr Lys Thr Ile Pro Met
65              70              75              80

Pro Thr Ala Asn Lys Ser Arg Ala Ala Ala Thr Pro Val Met Asn Ala
                85              90              95

Val Glu Asn Ala Thr Gly Val Arg Ser Gln Leu Leu Leu Thr Phe Ala
                100             105             110

Ser Ile Glu Ser Ala Phe Asp Tyr Glu Ile Lys Ala Lys Thr Ser Ser
                115             120             125

Ala Thr Gly Trp Phe Gln Phe Leu Thr Gly Thr Trp Lys Thr Met Ile
                130             135             140

Glu Asn Tyr Gly Met Lys Tyr Gly Val Leu Thr Asp Pro Thr Gly Ala
145             150             155             160

Leu Arg Lys Asp Pro Arg Ile Ser Ala Leu Met Gly Ala Glu Leu Ile
                165             170             175

Lys Glu Asn Met Asn Ile Leu Arg Pro Val Leu Lys Arg Glu Pro Thr
                180             185             190

Asp Thr Asp Leu Tyr Leu Ala His Phe Phe Gly Pro Gly Ala Ala Arg
                195             200             205

Arg Phe Leu Thr Thr Gly Gln Asn Glu Leu Ala Ala Thr His Phe Pro
                210             215             220

Lys Glu Ala Gln Ala Asn Pro Ser Ile Phe Tyr Asn Lys Asp Gly Ser
225             230             235             240

Pro Lys Thr Ile Gln Glu Val Tyr Asn Leu Met Asp Gly Lys Val Ala

```
                     245                 250                 255

Ala His Arg Lys
            260

<210> SEQ ID NO 7
<211> LENGTH: 260
<212> TYPE: PRT
<213> ORGANISM: artificial sequence
<220> FEATURE:
<223> OTHER INFORMATION: mutated KZ144 with T82I, A206V and S232

<400> SEQUENCE: 7

Met Lys Val Leu Arg Lys Gly Asp Arg Gly Asp Glu Val Cys Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Cys Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Ile Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 8
<211> LENGTH: 260
<212> TYPE: PRT
<213> ORGANISM: artificial sequence
<220> FEATURE:
<223> OTHER INFORMATION: mutated KZ144 with T82I, A206V, S232T, I122M
      and A160T

<400> SEQUENCE: 8

Met Lys Val Leu Arg Lys Gly Asp Arg Gly Asp Glu Val Cys Gln Leu
1               5                   10                  15
```

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Cys Leu Asp Ser Asp Gly Ile Val Gly Lys Asn Thr Trp Ala Glu
 50                  55                  60

Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 9
<211> LENGTH: 260
<212> TYPE: PRT
<213> ORGANISM: artificial sequence
<220> FEATURE:
<223> OTHER INFORMATION: mutated KZ144 with C14S, C50S, I122M and A160T

<400> SEQUENCE: 9

Met Lys Val Leu Arg Lys Gly Asp Arg Gly Asp Glu Val Ser Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Ser Leu Asp Ser Asp Gly Ile Val Gly Lys Asn Thr Trp Ala Glu
 50                  55                  60

Leu Phe Ser Lys Tyr Ser Pro Pro Ile Pro Tyr Lys Thr Ile Pro Met
 65                  70                  75                  80

Pro Thr Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

```
Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Ala Ala Arg
        195                 200                 205

Arg Phe Leu Thr Thr Gly Gln Asn Glu Leu Ala Ala Thr His Phe Pro
210                 215                 220

Lys Glu Ala Gln Ala Asn Pro Ser Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 10
<211> LENGTH: 260
<212> TYPE: PRT
<213> ORGANISM: artificial sequence
<220> FEATURE:
<223> OTHER INFORMATION: mutated KZ144 with C14S, C23S and C50S

<400> SEQUENCE: 10

Met Lys Val Leu Arg Lys Gly Asp Arg Gly Asp Glu Val Ser Gln Leu
1               5                   10                  15

Gln Thr Leu Leu Asn Leu Ser Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Ser Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Thr Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Ile Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Met Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Ala Ala Arg
        195                 200                 205
```

Arg Phe Leu Thr Thr Gly Gln Asn Glu Leu Ala Ala Thr His Phe Pro
            210                 215                 220

Lys Glu Ala Gln Ala Asn Pro Ser Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 11
<211> LENGTH: 260
<212> TYPE: PRT
<213> ORGANISM: artificial sequence
<220> FEATURE:
<223> OTHER INFORMATION: mutated KZ144 with T82I, A206V, S232T, I122M,
      A160T, C14S and C50S

<400> SEQUENCE: 11

Met Lys Val Leu Arg Lys Gly Asp Arg Gly Asp Glu Val Ser Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Ser Leu Asp Ser Asp Gly Ile Val Gly Lys Asn Thr Trp Ala Glu
50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 12
<211> LENGTH: 260
<212> TYPE: PRT

<213> ORGANISM: artificial sequence
<220> FEATURE:
<223> OTHER INFORMATION: mutated KZ144 with T82I, A206N, S232T, I122M, A160T, C14S and C50S

<400> SEQUENCE: 12

```
Met Lys Val Leu Arg Lys Gly Asp Arg Gly Asp Glu Val Ser Gln Leu
 1               5                  10                  15

Gln Thr Leu Leu Asn Leu Cys Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Ser Leu Asp Ser Asp Gly Ile Val Gly Lys Asn Thr Trp Ala Glu
        50                  55                  60

Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
                100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
                180                 185                 190

Asp Thr Asp Leu Tyr Leu Ala His Phe Phe Gly Pro Gly Asn Ala Arg
            195                 200                 205

Arg Phe Leu Thr Thr Gly Gln Asn Glu Leu Ala Ala Thr His Phe Pro
        210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260
```

<210> SEQ ID NO 13
<211> LENGTH: 260
<212> TYPE: PRT
<213> ORGANISM: artificial sequence
<220> FEATURE:
<223> OTHER INFORMATION: mutated KZ144 with N230Y, T82I, A206V, S232T, I122M, A160T, C14S and C50S

<400> SEQUENCE: 13

```
Met Lys Val Leu Arg Lys Gly Asp Arg Gly Asp Glu Val Ser Gln Leu
 1               5                  10                  15

Gln Thr Leu Leu Asn Leu Cys Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Ser Leu Asp Ser Asp Gly Ile Val Gly Lys Asn Thr Trp Ala Glu
```

```
                 50                  55                  60
Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Ala Thr Pro Val Met Asn Ala
                 85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
210                 215                 220

Lys Glu Ala Gln Ala Tyr Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 14
<211> LENGTH: 260
<212> TYPE: PRT
<213> ORGANISM: artificial sequence
<220> FEATURE:
<223> OTHER INFORMATION: mutated KZ144 with M180E, T82I, A206V, S232T,
      I122M, A160T, C14S and C50S

<400> SEQUENCE: 14

Met Lys Val Leu Arg Lys Gly Asp Arg Gly Asp Glu Val Ser Gln Leu
 1               5                  10                  15

Gln Thr Leu Leu Asn Leu Cys Gly Tyr Asp Val Gly Lys Pro Asp Gly
                 20                  25                  30

Ile Phe Gly Asn Asn Thr Phe Asn Gln Val Val Lys Phe Gln Lys Asp
             35                  40                  45

Asn Ser Leu Asp Ser Asp Gly Ile Val Gly Lys Asn Thr Trp Ala Glu
 50                  55                  60

Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Ala Thr Pro Val Met Asn Ala
                 85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140
```

```
Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Glu Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 15
<211> LENGTH: 260
<212> TYPE: PRT
<213> ORGANISM: artificial sequence
<220> FEATURE:
<223> OTHER INFORMATION: mutated KZ144 with M149P, T82I, A206V, S232T,
      I122M, A160T, C14S and C50S

<400> SEQUENCE: 15

Met Lys Val Leu Arg Lys Gly Asp Arg Gly Asp Glu Val Ser Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Ser Leu Asp Ser Asp Gly Ile Val Gly Lys Asn Thr Trp Ala Glu
50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Pro Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Thr Ile Phe Tyr Asn Lys Asp Gly Ser
225                 230                 235                 240
```

```
Pro Lys Thr Ile Gln Glu Val Tyr Asn Leu Met Asp Gly Lys Val Ala
                245                 250                 255

Ala His Arg Lys
            260

<210> SEQ ID NO 16
<211> LENGTH: 260
<212> TYPE: PRT
<213> ORGANISM: Artificial Sequence
<220> FEATURE:
<223> OTHER INFORMATION: mutated KZ144 with V186Y, T82I, A206V, S232T,
      I122M, A160T, C14S and C50S

<400> SEQUENCE: 16

Met Lys Val Leu Arg Lys Gly Asp Arg Gly Asp Glu Val Ser Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Ser Leu Asp Ser Asp Gly Ile Val Gly Lys Asn Thr Trp Ala Glu
50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Tyr Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 17
<211> LENGTH: 260
<212> TYPE: PRT
<213> ORGANISM: Artificial Sequence
<220> FEATURE:
<223> OTHER INFORMATION: mutated KZ144 with T82I, A206V, S232T, I122M,
      A160T, C14R and C50S

<400> SEQUENCE: 17
```

```
Met Lys Val Leu Arg Lys Gly Asp Arg Gly Asp Glu Val Arg Gln Leu
1               5                   10                  15

Gln Thr Leu Leu Asn Leu Cys Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Ser Leu Asp Ser Asp Gly Ile Val Gly Lys Asn Thr Trp Ala Glu
        50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
                100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
                180                 185                 190

Asp Thr Asp Leu Tyr Leu Ala His Phe Phe Gly Pro Gly Val Ala Arg
            195                 200                 205

Arg Phe Leu Thr Thr Gly Gln Asn Glu Leu Ala Ala Thr His Phe Pro
        210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 18
<211> LENGTH: 260
<212> TYPE: PRT
<213> ORGANISM: Artificial Sequence
<220> FEATURE:
<223> OTHER INFORMATION: mutated KZ144 with T82I, A206V, S232T, I122M,
    C14S and C50S

<400> SEQUENCE: 18

Met Lys Val Leu Arg Lys Gly Asp Arg Gly Asp Glu Val Cys Gln Leu
1               5                   10                  15

Gln Thr Leu Leu Asn Leu Cys Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Ser Leu Asp Ser Asp Gly Ile Val Gly Lys Asn Thr Trp Ala Glu
        50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
```

```
                    85                  90                  95
Val Glu Asn Ala Thr Gly Val Arg Ser Gln Leu Leu Leu Thr Phe Ala
                100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140

Glu Asn Tyr Gly Met Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
                180                 185                 190

Asp Thr Asp Leu Tyr Leu Ala His Phe Gly Pro Gly Val Ala Arg
                195                 200                 205

Arg Phe Leu Thr Thr Gly Gln Asn Glu Leu Ala Ala Thr His Phe Pro
        210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 19
<211> LENGTH: 260
<212> TYPE: PRT
<213> ORGANISM: Artificial Sequence
<220> FEATURE:
<223> OTHER INFORMATION: mutated KZ144 with T82I, A206V, S232T, I122M,
      A160T, C14S and C50N

<400> SEQUENCE: 19

Met Lys Val Leu Arg Lys Gly Asp Arg Gly Asp Glu Val Ser Gln Leu
1               5                   10                  15

Gln Thr Leu Leu Asn Leu Cys Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Asn Leu Asp Ser Asp Gly Ile Val Gly Lys Asn Thr Trp Ala Glu
50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
                100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140

Glu Asn Tyr Gly Met Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175
```

```
Lys Glu Asn Met Asn Ile Leu Arg Pro Val Leu Lys Arg Glu Pro Thr
                180                 185                 190

Asp Thr Asp Leu Tyr Leu Ala His Phe Phe Gly Pro Gly Val Ala Arg
            195                 200                 205

Arg Phe Leu Thr Thr Gly Gln Asn Glu Leu Ala Ala Thr His Phe Pro
        210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 20
<211> LENGTH: 260
<212> TYPE: PRT
<213> ORGANISM: Artificial Sequence
<220> FEATURE:
<223> OTHER INFORMATION: mutated KZ144 with C14R, C50S, T82I, I122M,
      M149P, A206V and S232T

<400> SEQUENCE: 20

Met Lys Val Leu Arg Lys Gly Asp Arg Gly Asp Glu Val Arg Gln Leu
1               5                   10                  15

Gln Thr Leu Leu Asn Leu Cys Gly Tyr Asp Val Gly Lys Pro Asp Gly
                20                  25                  30

Ile Phe Gly Asn Asn Thr Phe Asn Gln Val Val Lys Phe Gln Lys Asp
            35                  40                  45

Asn Ser Leu Asp Ser Asp Gly Ile Val Gly Lys Asn Thr Trp Ala Glu
50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
            130                 135                 140

Glu Asn Tyr Gly Pro Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
                180                 185                 190

Asp Thr Asp Leu Tyr Leu Ala His Phe Phe Gly Pro Gly Val Ala Arg
            195                 200                 205

Arg Phe Leu Thr Thr Gly Gln Asn Glu Leu Ala Ala Thr His Phe Pro
        210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260
```

<210> SEQ ID NO 21
<211> LENGTH: 260
<212> TYPE: PRT
<213> ORGANISM: Artificial Sequence
<220> FEATURE:
<223> OTHER INFORMATION: mutated KZ144 with C14R, C50S, T82I, I122M, M149P, A160T, A206V and S232T

<400> SEQUENCE: 21

Met Lys Val Leu Arg Lys Gly Asp Arg Gly Asp Glu Val Arg Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Ser Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Pro Lys Tyr Gly Val Leu Thr Asp Pro Thr Gly Thr
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 22
<211> LENGTH: 260
<212> TYPE: PRT
<213> ORGANISM: Artificial Sequence
<220> FEATURE:
<223> OTHER INFORMATION: mutated KZ144 with T82I, I122M, M149P, A206V, S232T, C14R and C50N

<400> SEQUENCE: 22

Met Lys Val Leu Arg Lys Gly Asp Arg Gly Asp Glu Val Arg Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
            35                  40                  45

Asn Asn Leu Asp Ser Asp Gly Ile Val Gly Lys Asn Thr Trp Ala Glu
 50                  55                  60

Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Thr Pro Val Met Asn Ala
                 85                  90                  95

Val Glu Asn Ala Thr Gly Val Arg Ser Gln Leu Leu Leu Thr Phe Ala
                100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140

Glu Asn Tyr Gly Pro Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 23
<211> LENGTH: 260
<212> TYPE: PRT
<213> ORGANISM: Artificial Sequence
<220> FEATURE:
<223> OTHER INFORMATION: mutated KZ144 with T82I, I122M, M149P, I167L,
      A206V, S232T, C14R and C50N

<400> SEQUENCE: 23

Met Lys Val Leu Arg Lys Gly Asp Arg Gly Asp Glu Val Arg Gln Leu
  1               5                  10                  15

Gln Thr Leu Leu Asn Leu Cys Gly Tyr Asp Val Gly Lys Pro Asp Gly
             20                  25                  30

Ile Phe Gly Asn Asn Thr Phe Asn Gln Val Val Lys Phe Gln Lys Asp
            35                  40                  45

Asn Asn Leu Asp Ser Asp Gly Ile Val Gly Lys Asn Thr Trp Ala Glu
 50                  55                  60

Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Thr Pro Val Met Asn Ala
                 85                  90                  95

Val Glu Asn Ala Thr Gly Val Arg Ser Gln Leu Leu Leu Thr Phe Ala
                100                 105                 110

Ser Ile Glu Ser Ala Phe Asp Tyr Glu Met Lys Ala Lys Thr Ser Ser

```
            115                 120                 125

Ala Thr Gly Trp Phe Gln Phe Leu Thr Gly Thr Trp Lys Thr Met Ile
        130                 135                 140

Glu Asn Tyr Gly Pro Lys Tyr Gly Val Leu Thr Asp Pro Thr Gly Ala
145                 150                 155                 160

Leu Arg Lys Asp Pro Arg Leu Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 24
<211> LENGTH: 260
<212> TYPE: PRT
<213> ORGANISM: Artificial Sequence
<220> FEATURE:
<223> OTHER INFORMATION: mutated KZ144 with T82I, I122M, M149P, N179F,
      A206V, S232T, C14R and C50N

<400> SEQUENCE: 24

Met Lys Val Leu Arg Lys Gly Asp Arg Gly Asp Glu Val Arg Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Asn Leu Asp Ser Asp Gly Ile Val Gly Lys Asn Thr Trp Ala Glu
    50                  55                  60

Leu Phe Ser Lys Tyr Ser Pro Pro Ile Pro Tyr Lys Thr Ile Pro Met
65                  70                  75                  80

Pro Ile Ala Asn Lys Ser Arg Ala Ala Ala Thr Pro Val Met Asn Ala
                85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Pro Lys Tyr Gly Val Leu Thr Asp Pro Thr Gly Ala
145                 150                 155                 160

Leu Arg Lys Asp Pro Arg Leu Ser Ala Leu Met Gly Ala Glu Leu Ile
                165                 170                 175

Lys Glu Phe Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205
```

```
Arg Phe Leu Thr Thr Gly Gln Asn Glu Leu Ala Ala Thr His Phe Pro
    210                 215                 220
Lys Glu Ala Gln Ala Asn Pro Thr Ile Phe Tyr Asn Lys Asp Gly Ser
225                 230                 235                 240
Pro Lys Thr Ile Gln Glu Val Tyr Asn Leu Met Asp Gly Lys Val Ala
                245                 250                 255
Ala His Arg Lys
            260

<210> SEQ ID NO 25
<211> LENGTH: 260
<212> TYPE: PRT
<213> ORGANISM: Artificial Sequence
<220> FEATURE:
<223> OTHER INFORMATION: mutated KZ144 with T82I, I122M, M149P, A206V,
      T212N, S232T, C14R and C50N

<400> SEQUENCE: 25

Met Lys Val Leu Arg Lys Gly Asp Arg Gly Asp Glu Val Arg Gln Leu
1               5                   10                  15
Gln Thr Leu Leu Asn Leu Cys Gly Tyr Asp Val Gly Lys Pro Asp Gly
            20                  25                  30
Ile Phe Gly Asn Asn Thr Phe Asn Gln Val Val Lys Phe Gln Lys Asp
        35                  40                  45
Asn Asn Leu Asp Ser Asp Gly Ile Val Gly Lys Asn Thr Trp Ala Glu
50                  55                  60
Leu Phe Ser Lys Tyr Ser Pro Pro Ile Pro Tyr Lys Thr Ile Pro Met
65                  70                  75                  80
Pro Ile Ala Asn Lys Ser Arg Ala Ala Ala Thr Pro Val Met Asn Ala
                85                  90                  95
Val Glu Asn Ala Thr Gly Val Arg Ser Gln Leu Leu Leu Thr Phe Ala
            100                 105                 110
Ser Ile Glu Ser Ala Phe Asp Tyr Glu Met Lys Ala Lys Thr Ser Ser
        115                 120                 125
Ala Thr Gly Trp Phe Gln Phe Leu Thr Gly Thr Trp Lys Thr Met Ile
130                 135                 140
Glu Asn Tyr Gly Pro Lys Tyr Gly Val Leu Thr Asp Pro Thr Gly Ala
145                 150                 155                 160
Leu Arg Lys Asp Pro Arg Ile Ser Ala Leu Met Gly Ala Glu Leu Ile
                165                 170                 175
Lys Glu Asn Met Asn Ile Leu Arg Pro Val Leu Lys Arg Glu Pro Thr
            180                 185                 190
Asp Thr Asp Leu Tyr Leu Ala His Phe Phe Gly Pro Gly Val Ala Arg
        195                 200                 205
Arg Phe Leu Asn Thr Gly Gln Asn Glu Leu Ala Ala Thr His Phe Pro
    210                 215                 220
Lys Glu Ala Gln Ala Asn Pro Thr Ile Phe Tyr Asn Lys Asp Gly Ser
225                 230                 235                 240
Pro Lys Thr Ile Gln Glu Val Tyr Asn Leu Met Asp Gly Lys Val Ala
                245                 250                 255
Ala His Arg Lys
            260

<210> SEQ ID NO 26
<211> LENGTH: 260
<212> TYPE: PRT
<213> ORGANISM: Artificial Sequence
```

```
<220> FEATURE:
<223> OTHER INFORMATION: mutated KZ144 with T82I, I122M, M149P, A206V,
      P224Q, S232T, C14R and C50N

<400> SEQUENCE: 26

Met Lys Val Leu Arg Lys Gly Asp Arg Gly Asp Glu Val Arg Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Asn Leu Asp Ser Asp Gly Ile Val Gly Lys Asn Thr Trp Ala Glu
 50                  55                  60

Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Thr Pro Val Met Asn Ala
             85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
            115                 120                 125

Ala Thr Gly Trp Phe Gln Phe Leu Thr Gly Thr Trp Lys Thr Met Ile
        130                 135                 140

Glu Asn Tyr Gly Pro Lys Tyr Gly Val Leu Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Gln
    210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 27
<211> LENGTH: 260
<212> TYPE: PRT
<213> ORGANISM: Artificial Sequence
<220> FEATURE:
<223> OTHER INFORMATION: mutated KZ144 with T82I, I122M, M149P, L154T,
      A206V, S232T, C14R and C50N

<400> SEQUENCE: 27

Met Lys Val Leu Arg Lys Gly Asp Arg Gly Asp Glu Val Arg Gln Leu
1               5                   10                  15

Gln Thr Leu Leu Asn Leu Cys Gly Tyr Asp Val Gly Lys Pro Asp Gly
            20                  25                  30

Ile Phe Gly Asn Asn Thr Phe Asn Gln Val Val Lys Phe Gln Lys Asp
        35                  40                  45

Asn Asn Leu Asp Ser Asp Gly Ile Val Gly Lys Asn Thr Trp Ala Glu
 50                  55                  60
```

```
Leu Phe Ser Lys Tyr Ser Pro Pro Ile Pro Tyr Lys Thr Ile Pro Met
 65                  70                  75                  80

Pro Ile Ala Asn Lys Ser Arg Ala Ala Ala Thr Pro Val Met Asn Ala
                 85                  90                  95

Val Glu Asn Ala Thr Gly Val Arg Ser Gln Leu Leu Leu Thr Phe Ala
            100                 105                 110

Ser Ile Glu Ser Ala Phe Asp Tyr Glu Met Lys Ala Lys Thr Ser Ser
        115                 120                 125

Ala Thr Gly Trp Phe Gln Phe Leu Thr Gly Thr Trp Lys Thr Met Ile
    130                 135                 140

Glu Asn Tyr Gly Pro Lys Tyr Gly Val Thr Thr Asp Pro Thr Gly Ala
145                 150                 155                 160

Leu Arg Lys Asp Pro Arg Ile Ser Ala Leu Met Gly Ala Glu Leu Ile
                165                 170                 175

Lys Glu Asn Met Asn Ile Leu Arg Pro Val Leu Lys Arg Glu Pro Thr
            180                 185                 190

Asp Thr Asp Leu Tyr Leu Ala His Phe Phe Gly Pro Gly Val Ala Arg
        195                 200                 205

Arg Phe Leu Thr Thr Gly Gln Asn Glu Leu Ala Ala Thr His Phe Pro
    210                 215                 220

Lys Glu Ala Gln Ala Asn Pro Thr Ile Phe Tyr Asn Lys Asp Gly Ser
225                 230                 235                 240

Pro Lys Thr Ile Gln Glu Val Tyr Asn Leu Met Asp Gly Lys Val Ala
                245                 250                 255

Ala His Arg Lys
            260

<210> SEQ ID NO 28
<211> LENGTH: 259
<212> TYPE: PRT
<213> ORGANISM: artificial sequence
<220> FEATURE:
<223> OTHER INFORMATION: mutated KZ144 with C14S and C50S, without
      N-terminal methionine

<400> SEQUENCE: 28

Lys Val Leu Arg Lys Gly Asp Arg Gly Asp Glu Val Ser Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Thr Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Ile Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Met Lys Tyr Gly Val Leu Thr Asp Pro Thr Gly Ala Leu
```

```
            145                 150                 155                 160
        Arg Lys Asp Pro Arg Ile Ser Ala Leu Met Gly Ala Glu Leu Ile Lys
                        165                 170                 175
        Glu Asn Met Asn Ile Leu Arg Pro Val Leu Lys Arg Glu Pro Thr Asp
                        180                 185                 190
        Thr Asp Leu Tyr Leu Ala His Phe Gly Pro Gly Ala Ala Arg Arg
                        195                 200                 205
        Phe Leu Thr Thr Gly Gln Asn Glu Leu Ala Ala Thr His Phe Pro Lys
                        210                 215                 220
        Glu Ala Gln Ala Asn Pro Ser Ile Phe Tyr Asn Lys Asp Gly Ser Pro
        225                 230                 235                 240
        Lys Thr Ile Gln Glu Val Tyr Asn Leu Met Asp Gly Lys Val Ala Ala
                        245                 250                 255
        His Arg Lys

<210> SEQ ID NO 29
<211> LENGTH: 259
<212> TYPE: PRT
<213> ORGANISM: artificial sequence
<220> FEATURE:
<223> OTHER INFORMATION: mutated KZ144 with T82I, A206V and S232,
      without N-terminal methionine

<400> SEQUENCE: 29

Lys Val Leu Arg Lys Gly Asp Arg Gly Asp Glu Val Cys Gln Leu Gln
        1               5                   10                  15
        Thr Leu Leu Asn Leu Cys Gly Tyr Asp Val Gly Lys Pro Asp Gly Ile
                        20                  25                  30
        Phe Gly Asn Asn Thr Phe Asn Gln Val Val Lys Phe Gln Lys Asp Asn
                        35                  40                  45
        Cys Leu Asp Ser Asp Gly Ile Val Gly Lys Asn Thr Trp Ala Glu Leu
                        50                  55                  60
        Phe Ser Lys Tyr Ser Pro Pro Ile Pro Tyr Lys Thr Ile Pro Met Pro
        65                  70                  75                  80
        Ile Ala Asn Lys Ser Arg Ala Ala Ala Thr Pro Val Met Asn Ala Val
                        85                  90                  95
        Glu Asn Ala Thr Gly Val Arg Ser Gln Leu Leu Leu Thr Phe Ala Ser
                        100                 105                 110
        Ile Glu Ser Ala Phe Asp Tyr Glu Ile Lys Ala Lys Thr Ser Ser Ala
                        115                 120                 125
        Thr Gly Trp Phe Gln Phe Leu Thr Gly Thr Trp Lys Thr Met Ile Glu
                        130                 135                 140
        Asn Tyr Gly Met Lys Tyr Gly Val Leu Thr Asp Pro Thr Gly Ala Leu
        145                 150                 155                 160
        Arg Lys Asp Pro Arg Ile Ser Ala Leu Met Gly Ala Glu Leu Ile Lys
                        165                 170                 175
        Glu Asn Met Asn Ile Leu Arg Pro Val Leu Lys Arg Glu Pro Thr Asp
                        180                 185                 190
        Thr Asp Leu Tyr Leu Ala His Phe Gly Pro Gly Val Ala Arg Arg
                        195                 200                 205
        Phe Leu Thr Thr Gly Gln Asn Glu Leu Ala Ala Thr His Phe Pro Lys
                        210                 215                 220
        Glu Ala Gln Ala Asn Pro Thr Ile Phe Tyr Asn Lys Asp Gly Ser Pro
        225                 230                 235                 240
        Lys Thr Ile Gln Glu Val Tyr Asn Leu Met Asp Gly Lys Val Ala Ala
```

-continued

```
            245                 250                 255

His Arg Lys

<210> SEQ ID NO 30
<211> LENGTH: 259
<212> TYPE: PRT
<213> ORGANISM: artificial sequence
<220> FEATURE:
<223> OTHER INFORMATION: mutated KZ144 with T82I, A206V, S232T, I122M
      and A160T, without N-terminal methionine

<400> SEQUENCE: 30

Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Cys Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 31
<211> LENGTH: 259
<212> TYPE: PRT
<213> ORGANISM: artificial sequence
<220> FEATURE:
<223> OTHER INFORMATION: mutated KZ144 with C14S, C50S, I122M and A160T,
      without N-terminal methionine

<400> SEQUENCE: 31

Lys Val Leu Arg Lys Gly Asp Arg Gly Asp Glu Val Ser Gln Leu Gln
1               5                   10                  15
```

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
 50                  55                  60

Phe Ser Lys Tyr Ser Pro Pro Ile Pro Tyr Lys Thr Ile Pro Met Pro
65                  70                  75                  80

Thr Ala Asn Lys Ser Arg Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Gly Pro Gly Ala Ala Arg Arg
        195                 200                 205

Phe Leu Thr Thr Gly Gln Asn Glu Leu Ala Ala Thr His Phe Pro Lys
210                 215                 220

Glu Ala Gln Ala Asn Pro Ser Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 32
<211> LENGTH: 259
<212> TYPE: PRT
<213> ORGANISM: artificial sequence
<220> FEATURE:
<223> OTHER INFORMATION: mutated KZ144 with C14S, C23S and C50S, without
      N-terminal methionine

<400> SEQUENCE: 32

Lys Val Leu Arg Lys Gly Asp Arg Gly Asp Glu Val Ser Gln Leu Gln
1               5                   10                  15

Thr Leu Leu Asn Leu Ser Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
 50                  55                  60

Phe Ser Lys Tyr Ser Pro Pro Ile Pro Tyr Lys Thr Ile Pro Met Pro
65                  70                  75                  80

Thr Ala Asn Lys Ser Arg Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

```
Ile Glu Ser Ala Phe Asp Tyr Glu Ile Lys Ala Lys Thr Ser Ser Ala
            115                 120                 125

Thr Gly Trp Phe Gln Phe Leu Thr Gly Thr Trp Lys Thr Met Ile Glu
130                 135                 140

Asn Tyr Gly Met Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Ala Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Ser Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 33
<211> LENGTH: 259
<212> TYPE: PRT
<213> ORGANISM: artificial sequence
<220> FEATURE:
<223> OTHER INFORMATION: mutated KZ144 with T82I, A206V, S232T, I122M,
      A160T, C14S and C50S, without N-terminal methionine

<400> SEQUENCE: 33

Lys Val Leu Arg Lys Gly Asp Arg Gly Asp Glu Val Ser Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205
```

```
Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 34
<211> LENGTH: 259
<212> TYPE: PRT
<213> ORGANISM: artificial sequence
<220> FEATURE:
<223> OTHER INFORMATION: mutated KZ144 with T82I, A206N, S232T, I122M,
      A160T, C14S and C50S, without N-terminal methionine

<400> SEQUENCE: 34

Lys Val Leu Arg Lys Gly Asp Arg Gly Asp Glu Val Ser Gln Leu Gln
1               5                   10                  15

Thr Leu Leu Asn Leu Cys Gly Tyr Asp Val Gly Lys Pro Asp Gly Ile
                20                  25                  30

Phe Gly Asn Asn Thr Phe Asn Gln Val Val Lys Phe Gln Lys Asp Asn
            35                  40                  45

Ser Leu Asp Ser Asp Gly Ile Val Gly Lys Asn Thr Trp Ala Glu Leu
50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Thr Pro Val Met Asn Ala Val
                85                  90                  95

Glu Asn Ala Thr Gly Val Arg Ser Gln Leu Leu Leu Thr Phe Ala Ser
                100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Gly Pro Gly Asn Ala Arg Arg
            195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 35
<211> LENGTH: 259
<212> TYPE: PRT
<213> ORGANISM: Artificial Sequence
<220> FEATURE:
<223> OTHER INFORMATION: mutated KZ144 with N230Y, T82I, A206V, S232T,
```

I122M, A160T, C14S and C50S, without N-terminal methionine

<400> SEQUENCE: 35

```
Lys Val Leu Arg Lys Gly Asp Arg Gly Asp Glu Val Ser Gln Leu Gln
1               5                  10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Pro Lys
    210                 215                 220

Glu Ala Gln Ala Tyr Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys
```

<210> SEQ ID NO 36
<211> LENGTH: 259
<212> TYPE: PRT
<213> ORGANISM: Artificial Sequence
<220> FEATURE:
<223> OTHER INFORMATION: mutated KZ144 with M180E, T82I, A206V, S232T, I122M, A160T, C14S and C50S, without N-terminal methionine

<400> SEQUENCE: 36

```
Lys Val Leu Arg Lys Gly Asp Arg Gly Asp Glu Val Ser Gln Leu Gln
1               5                  10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80
```

```
Ile Ala Asn Lys Ser Arg Ala Ala Ala Thr Pro Val Met Asn Ala Val
                85                  90                  95

Glu Asn Ala Thr Gly Val Arg Ser Gln Leu Leu Thr Phe Ala Ser
            100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Glu Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
            195                 200                 205

Phe Leu Thr Thr Gly Gln Asn Glu Leu Ala Ala Thr His Phe Pro Lys
210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 37
<211> LENGTH: 259
<212> TYPE: PRT
<213> ORGANISM: Artificial Sequence
<220> FEATURE:
<223> OTHER INFORMATION: mutated KZ144 with M149P, T82I, A206V, S232T,
      I122M, A160T, C14S and C50S, without N-terminal methionine

<400> SEQUENCE: 37

Lys Val Leu Arg Lys Gly Asp Arg Gly Asp Glu Val Ser Gln Leu Gln
1               5                   10                  15

Thr Leu Leu Asn Leu Cys Gly Tyr Asp Val Gly Lys Pro Asp Gly Ile
                20                  25                  30

Phe Gly Asn Asn Thr Phe Asn Gln Val Val Lys Phe Gln Lys Asp Asn
            35                  40                  45

Ser Leu Asp Ser Asp Gly Ile Val Gly Lys Asn Thr Trp Ala Glu Leu
50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Thr Phe Ala Ser
            100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
130                 135                 140

Asn Tyr Gly Pro Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175
```

```
Glu Asn Met Asn Ile Leu Arg Pro Val Leu Lys Arg Glu Pro Thr Asp
            180                 185                 190

Thr Asp Leu Tyr Leu Ala His Phe Gly Pro Gly Val Ala Arg Arg
        195                 200                 205

Phe Leu Thr Thr Gly Gln Asn Glu Leu Ala Ala Thr His Phe Pro Lys
        210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys
```

<210> SEQ ID NO 38
<211> LENGTH: 259
<212> TYPE: PRT
<213> ORGANISM: Artificial Sequence
<220> FEATURE:
<223> OTHER INFORMATION: mutated KZ144 with V186Y, T82I, A206V, S232T, I122M, A160T, C14S and C50S, without N-terminal methionine

<400> SEQUENCE: 38

```
Lys Val Leu Arg Lys Gly Asp Arg Gly Asp Glu Val Ser Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
50              55                  60

Phe Ser Lys Tyr Ser Pro Pro Ile Pro Tyr Lys Thr Ile Pro Met Pro
65              70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Tyr Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys
```

<210> SEQ ID NO 39
<211> LENGTH: 259
<212> TYPE: PRT
<213> ORGANISM: Artificial Sequence
<220> FEATURE:
<223> OTHER INFORMATION: mutated KZ144 with T82I, A206V, S232T, I122M,
      A160T, C14R and C50S, without N-terminal methionine

<400> SEQUENCE: 39

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Ser Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 40
<211> LENGTH: 259
<212> TYPE: PRT
<213> ORGANISM: Artificial Sequence
<220> FEATURE:
<223> OTHER INFORMATION: mutated KZ144 with T82I, A206V, S232T, I122M,
      C14S and C50S, without N-terminal methionine

<400> SEQUENCE: 40

Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn

```
                35                  40                  45
Ser Leu Asp Ser Asp Gly Ile Val Gly Lys Asn Thr Trp Ala Glu Leu
 50                  55                  60

Phe Ser Lys Tyr Ser Pro Pro Ile Pro Tyr Lys Thr Ile Pro Met Pro
 65                  70                  75                  80

Ile Ala Asn Lys Ser Arg Ala Ala Ala Thr Pro Val Met Asn Ala Val
                 85                  90                  95

Glu Asn Ala Thr Gly Val Arg Ser Gln Leu Leu Leu Thr Phe Ala Ser
                100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
        130                 135                 140

Asn Tyr Gly Met Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Gly Pro Gly Val Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 41
<211> LENGTH: 259
<212> TYPE: PRT
<213> ORGANISM: Artificial Sequence
<220> FEATURE:
<223> OTHER INFORMATION: mutated KZ144 with T82I, A206V, S232T, I122M,
      A160T, C14S and C50N, without N-terminal methionine

<400> SEQUENCE: 41

Lys Val Leu Arg Lys Gly Asp Arg Gly Asp Glu Val Ser Gln Leu Gln
 1               5                  10                  15

Thr Leu Leu Asn Leu Cys Gly Tyr Asp Val Gly Lys Pro Asp Gly Ile
                 20                  25                  30

Phe Gly Asn Asn Thr Phe Asn Gln Val Val Lys Phe Gln Lys Asp Asn
             35                  40                  45

Asn Leu Asp Ser Asp Gly Ile Val Gly Lys Asn Thr Trp Ala Glu Leu
 50                  55                  60

Phe Ser Lys Tyr Ser Pro Pro Ile Pro Tyr Lys Thr Ile Pro Met Pro
 65                  70                  75                  80

Ile Ala Asn Lys Ser Arg Ala Ala Ala Thr Pro Val Met Asn Ala Val
                 85                  90                  95

Glu Asn Ala Thr Gly Val Arg Ser Gln Leu Leu Leu Thr Phe Ala Ser
                100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
```

```
            130                 135                 140
Asn Tyr Gly Met Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
                195                 200                 205

Phe Leu Thr Thr Gly Gln Asn Glu Leu Ala Ala Thr His Phe Pro Lys
            210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 42
<211> LENGTH: 259
<212> TYPE: PRT
<213> ORGANISM: Artificial Sequence
<220> FEATURE:
<223> OTHER INFORMATION: mutated KZ144 with C14R, C50S, T82I, I122M,
      M149P, A206V and S232T; without N-terminal methionine

<400> SEQUENCE: 42

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
                20                  25                  30

Phe Gly Asn Asn Thr Phe Asn Gln Val Val Lys Phe Gln Lys Asp Asn
            35                  40                  45

Ser Leu Asp Ser Asp Gly Ile Val Gly Lys Asn Thr Trp Ala Glu Leu
50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
            130                 135                 140

Asn Tyr Gly Pro Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
                195                 200                 205

Phe Leu Thr Thr Gly Gln Asn Glu Leu Ala Ala Thr His Phe Pro Lys
            210                 215                 220

Glu Ala Gln Ala Asn Pro Thr Ile Phe Tyr Asn Lys Asp Gly Ser Pro
```

225                 230                 235                 240

Lys Thr Ile Gln Glu Val Tyr Asn Leu Met Asp Gly Lys Val Ala Ala
                245                 250                 255

His Arg Lys

<210> SEQ ID NO 43
<211> LENGTH: 259
<212> TYPE: PRT
<213> ORGANISM: Artificial Sequence
<220> FEATURE:
<223> OTHER INFORMATION: mutated KZ144 with C14R, C50S, T82I, I122M,
      M149P, A160T, A206V and S232T; without N-terminal methionine

<400> SEQUENCE: 43

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
                20                  25                  30

Phe Gly Asn Asn Thr Phe Asn Gln Val Val Lys Phe Gln Lys Asp Asn
            35                  40                  45

Ser Leu Asp Ser Asp Gly Ile Val Gly Lys Asn Thr Trp Ala Glu Leu
50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Pro Lys Tyr Gly Val Leu Thr Asp Pro Thr Gly Thr Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 44
<211> LENGTH: 259
<212> TYPE: PRT
<213> ORGANISM: Artificial Sequence
<220> FEATURE:
<223> OTHER INFORMATION: mutated KZ144 with T82I, I122M, M149P, A206V,
      S232T, C14R and C50N, without N-terminal methionine

<400> SEQUENCE: 44

```
Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Asn Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Thr Phe Ala Ser
                100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
        130                 135                 140

Asn Tyr Gly Pro Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 45
<211> LENGTH: 259
<212> TYPE: PRT
<213> ORGANISM: Artificial Sequence
<220> FEATURE:
<223> OTHER INFORMATION: mutated KZ144 with T82I, I122M, M149P, I167L,
      A206V, S232T, C14R and C50N, without N-terminal methionine

<400> SEQUENCE: 45

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Asn Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95
```

```
Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Pro Lys Tyr Gly Val Leu Thr Asp Pro Thr Gly Ala Leu
145                 150                 155                 160

Arg Lys Asp Pro Arg Leu Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Pro Lys
210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 46
<211> LENGTH: 259
<212> TYPE: PRT
<213> ORGANISM: Artificial Sequence
<220> FEATURE:
<223> OTHER INFORMATION: mutated KZ144 with T82I, I122M, M149P, N179F,
      A206V, S232T, C14R and C50N, without N-terminal methionine

<400> SEQUENCE: 46

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Asn Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Pro Lys Tyr Gly Val Leu Thr Asp Pro Thr Gly Ala Leu
145                 150                 155                 160

Arg Lys Asp Pro Arg Leu Ser Ala Leu Met Gly Ala Glu Leu Ile Lys
                165                 170                 175

Glu Phe Met Asn Ile Leu Arg Pro Val Leu Lys Arg Glu Pro Thr Asp
            180                 185                 190
```

Thr Asp Leu Tyr Leu Ala His Phe Phe Gly Pro Gly Val Ala Arg Arg
            195                 200                 205

Phe Leu Thr Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
            245                 250                 255

His Arg Lys

<210> SEQ ID NO 47
<211> LENGTH: 259
<212> TYPE: PRT
<213> ORGANISM: Artificial Sequence
<220> FEATURE:
<223> OTHER INFORMATION: mutated KZ144 with T82I, I122M, M149P, A206V,
      T212N, S232T, C14R and C50N, without N-terminal methionine

<400> SEQUENCE: 47

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Asn Leu Asp Ser Asp Gly Ile Val Gly Lys Asn Thr Trp Ala Glu Leu
    50                  55                  60

Phe Ser Lys Tyr Ser Pro Ile Pro Tyr Lys Thr Ile Pro Met Pro
65                  70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Pro Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Asn Thr Gly Gln Asn Glu Leu Ala Ala Thr His Phe Pro Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 48
<211> LENGTH: 259
<212> TYPE: PRT

<213> ORGANISM: Artificial Sequence
<220> FEATURE:
<223> OTHER INFORMATION: mutated KZ144 with T82I, I122M, M149P, A206V,
     P224Q, S232T, C14R and C50N, without N-terminal methionine

<400> SEQUENCE: 48

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Asn Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Met Pro
65              70                  75                  80

Ile Ala Asn Lys Ser Arg Ala Ala Ala Thr Pro Val Met Asn Ala Val
                85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
        115                 120                 125

Thr Gly Trp Phe Gln Phe Leu Thr Gly Thr Trp Lys Thr Met Ile Glu
    130                 135                 140

Asn Tyr Gly Pro Lys Tyr Gly Val Leu Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
        195                 200                 205

Phe Leu Thr Thr Gly Gln Asn Glu Leu Ala Ala Thr His Phe Gln Lys
    210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 49
<211> LENGTH: 259
<212> TYPE: PRT
<213> ORGANISM: Artificial Sequence
<220> FEATURE:
<223> OTHER INFORMATION: mutated KZ144 with T82I, I122M, M149P, L154T,
     A206V, S232T, C14R and C50N, without N-terminal methionine

<400> SEQUENCE: 49

Lys Val Leu Arg Lys Gly Asp Arg Gly Asp Glu Val Arg Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Asn Leu Asp Ser Asp Gly Ile Val Gly Lys Asn Thr Trp Ala Glu Leu
    50                  55                  60

```
Phe Ser Lys Tyr Ser Pro Pro Ile Pro Tyr Lys Thr Ile Pro Met Pro
 65                  70                  75                  80

Ile Ala Asn Lys Ser Arg Ala Ala Ala Thr Pro Val Met Asn Ala Val
             85                  90                  95

Glu Asn Ala Thr Gly Val Arg Ser Gln Leu Leu Leu Thr Phe Ala Ser
            100                 105                 110

Ile Glu Ser Ala Phe Asp Tyr Glu Met Lys Ala Lys Thr Ser Ser Ala
            115                 120                 125

Thr Gly Trp Phe Gln Phe Leu Thr Gly Thr Trp Lys Thr Met Ile Glu
            130                 135                 140

Asn Tyr Gly Pro Lys Tyr Gly Val Thr Thr Asp Pro Thr Gly Ala Leu
145                 150                 155                 160

Arg Lys Asp Pro Arg Ile Ser Ala Leu Met Gly Ala Glu Leu Ile Lys
                165                 170                 175

Glu Asn Met Asn Ile Leu Arg Pro Val Leu Lys Arg Glu Pro Thr Asp
            180                 185                 190

Thr Asp Leu Tyr Leu Ala His Phe Phe Gly Pro Gly Val Ala Arg Arg
            195                 200                 205

Phe Leu Thr Thr Gly Gln Asn Glu Leu Ala Ala Thr His Phe Pro Lys
            210                 215                 220

Glu Ala Gln Ala Asn Pro Thr Ile Phe Tyr Asn Lys Asp Gly Ser Pro
225                 230                 235                 240

Lys Thr Ile Gln Glu Val Tyr Asn Leu Met Asp Gly Lys Val Ala Ala
                245                 250                 255

His Arg Lys

<210> SEQ ID NO 50
<211> LENGTH: 6
<212> TYPE: PRT
<213> ORGANISM: artificial
<220> FEATURE:
<223> OTHER INFORMATION: synthetic sequence

<400> SEQUENCE: 50

Lys Arg Lys Lys Arg Lys
1               5

<210> SEQ ID NO 51
<211> LENGTH: 5
<212> TYPE: PRT
<213> ORGANISM: artificial
<220> FEATURE:
<223> OTHER INFORMATION: synethtic sequence
<220> FEATURE:
<221> NAME/KEY: misc_feature
<222> LOCATION: (3)..(3)
<223> OTHER INFORMATION: Xaa can be any naturally occurring amino acid

<400> SEQUENCE: 51

Lys Arg Xaa Lys Arg
1               5

<210> SEQ ID NO 52
<211> LENGTH: 5
<212> TYPE: PRT
<213> ORGANISM: artificial
<220> FEATURE:
<223> OTHER INFORMATION: synthetic sequence

<400> SEQUENCE: 52
```

```
Lys Arg Ser Lys Arg
1               5

<210> SEQ ID NO 53
<211> LENGTH: 5
<212> TYPE: PRT
<213> ORGANISM: artificial
<220> FEATURE:
<223> OTHER INFORMATION: synthetic sequence

<400> SEQUENCE: 53

Lys Arg Gly Ser Gly
1               5

<210> SEQ ID NO 54
<211> LENGTH: 9
<212> TYPE: PRT
<213> ORGANISM: artificial
<220> FEATURE:
<223> OTHER INFORMATION: synthetic sequence

<400> SEQUENCE: 54

Lys Arg Lys Lys Arg Lys Lys Arg Lys
1               5

<210> SEQ ID NO 55
<211> LENGTH: 9
<212> TYPE: PRT
<213> ORGANISM: artificial
<220> FEATURE:
<223> OTHER INFORMATION: synthetic sequence

<400> SEQUENCE: 55

Arg Arg Arg Arg Arg Arg Arg Arg Arg
1               5

<210> SEQ ID NO 56
<211> LENGTH: 8
<212> TYPE: PRT
<213> ORGANISM: artificial
<220> FEATURE:
<223> OTHER INFORMATION: synthetic sequence

<400> SEQUENCE: 56

Lys Lys Lys Lys Lys Lys Lys Lys
1               5

<210> SEQ ID NO 57
<211> LENGTH: 10
<212> TYPE: PRT
<213> ORGANISM: artificial
<220> FEATURE:
<223> OTHER INFORMATION: synthetic sequence

<400> SEQUENCE: 57

Lys Arg Lys Lys Arg Lys Lys Arg Lys Lys
1               5                   10

<210> SEQ ID NO 58
<211> LENGTH: 12
<212> TYPE: PRT
<213> ORGANISM: artificial
<220> FEATURE:
<223> OTHER INFORMATION: synthetic sequence

<400> SEQUENCE: 58

Lys Arg Lys Lys Arg Lys Lys Arg Lys Lys Arg Lys
```

-continued

```
<210> SEQ ID NO 59
<211> LENGTH: 14
<212> TYPE: PRT
<213> ORGANISM: artificial
<220> FEATURE:
<223> OTHER INFORMATION: synthetic sequence

<400> SEQUENCE: 59

Lys Arg Lys Lys Arg Lys Lys Arg Lys Lys Arg Lys Lys Arg
1               5                   10

<210> SEQ ID NO 60
<211> LENGTH: 16
<212> TYPE: PRT
<213> ORGANISM: artificial
<220> FEATURE:
<223> OTHER INFORMATION: synthetic sequence

<400> SEQUENCE: 60

Lys Lys Lys Lys Lys Lys Lys Lys Lys Lys Lys Lys Lys Lys Lys Lys
1               5                   10                  15

<210> SEQ ID NO 61
<211> LENGTH: 18
<212> TYPE: PRT
<213> ORGANISM: artificial
<220> FEATURE:
<223> OTHER INFORMATION: synthetic sequence

<400> SEQUENCE: 61

Lys Arg Lys Lys Arg Lys Lys Arg Lys Lys Arg Lys Lys Arg Lys Lys
1               5                   10                  15

Arg Lys

<210> SEQ ID NO 62
<211> LENGTH: 19
<212> TYPE: PRT
<213> ORGANISM: artificial
<220> FEATURE:
<223> OTHER INFORMATION: synthetic sequence

<400> SEQUENCE: 62

Lys Arg Lys Lys Arg Lys Lys Arg Lys Lys Arg Lys Lys Arg Lys Lys
1               5                   10                  15

Arg Lys Lys

<210> SEQ ID NO 63
<211> LENGTH: 19
<212> TYPE: PRT
<213> ORGANISM: artificial
<220> FEATURE:
<223> OTHER INFORMATION: synthetic sequence

<400> SEQUENCE: 63

Arg Arg Arg Arg Arg Arg Arg Arg Arg Arg Arg Arg Arg Arg Arg Arg
1               5                   10                  15

Arg Arg Arg

<210> SEQ ID NO 64
<211> LENGTH: 19
<212> TYPE: PRT
<213> ORGANISM: artificial
<220> FEATURE:
```

```
<223> OTHER INFORMATION: synthetic sequence

<400> SEQUENCE: 64

Lys Lys Lys Lys Lys Lys Lys Lys Lys Lys Lys Lys Lys Lys Lys
1               5                   10                  15

Lys Lys Lys

<210> SEQ ID NO 65
<211> LENGTH: 20
<212> TYPE: PRT
<213> ORGANISM: artificial
<220> FEATURE:
<223> OTHER INFORMATION: synthetic sequence

<400> SEQUENCE: 65

Lys Arg Lys Lys Arg Lys Lys Arg Lys Arg Ser Lys Arg Lys Lys Arg
1               5                   10                  15

Lys Lys Arg Lys
            20

<210> SEQ ID NO 66
<211> LENGTH: 21
<212> TYPE: PRT
<213> ORGANISM: artificial
<220> FEATURE:
<223> OTHER INFORMATION: synthetic sequence

<400> SEQUENCE: 66

Lys Arg Lys Lys Arg Lys Lys Arg Lys Arg Ser Lys Arg Lys Lys Arg
1               5                   10                  15

Lys Lys Arg Lys Lys
            20

<210> SEQ ID NO 67
<211> LENGTH: 21
<212> TYPE: PRT
<213> ORGANISM: artificial
<220> FEATURE:
<223> OTHER INFORMATION: synthetic sequence

<400> SEQUENCE: 67

Lys Arg Lys Lys Arg Lys Lys Arg Lys Lys Arg Lys Lys Arg Lys Lys
1               5                   10                  15

Arg Lys Lys Arg Lys
            20

<210> SEQ ID NO 68
<211> LENGTH: 22
<212> TYPE: PRT
<213> ORGANISM: artificial
<220> FEATURE:
<223> OTHER INFORMATION: synthetic sequence

<400> SEQUENCE: 68

Lys Arg Lys Lys Arg Lys Lys Arg Lys Arg Gly Ser Gly Lys Arg Lys
1               5                   10                  15

Lys Arg Lys Lys Arg Lys
            20

<210> SEQ ID NO 69
<211> LENGTH: 24
<212> TYPE: PRT
<213> ORGANISM: artificial
<220> FEATURE:
```

<223> OTHER INFORMATION: synthetic sequence

<400> SEQUENCE: 69

Lys Arg Lys Lys Arg Lys Lys Arg Lys Arg Gly Ser Gly Ser Gly Lys
1               5                   10                  15

Arg Lys Lys Arg Lys Lys Arg Lys
            20

<210> SEQ ID NO 70
<211> LENGTH: 25
<212> TYPE: PRT
<213> ORGANISM: artificial
<220> FEATURE:
<223> OTHER INFORMATION: synthetic sequence

<400> SEQUENCE: 70

Lys Arg Lys Lys Arg Lys Lys Arg Lys Lys Arg Lys Lys Arg Lys Lys
1               5                   10                  15

Arg Lys Lys Arg Lys Lys Arg Lys Lys
            20                  25

<210> SEQ ID NO 71
<211> LENGTH: 31
<212> TYPE: PRT
<213> ORGANISM: artificial
<220> FEATURE:
<223> OTHER INFORMATION: synthetic sequence

<400> SEQUENCE: 71

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys
            20                  25                  30

<210> SEQ ID NO 72
<211> LENGTH: 38
<212> TYPE: PRT
<213> ORGANISM: artificial
<220> FEATURE:
<223> OTHER INFORMATION: synthetic sequence

<400> SEQUENCE: 72

Lys Arg Lys Lys Arg Lys Lys Arg Lys Arg Gly Ser Gly Ser Gly Lys
1               5                   10                  15

Arg Lys Lys Arg Lys Lys Arg Lys Gly Ser Gly Ser Gly Lys Arg Lys
            20                  25                  30

Lys Arg Lys Lys Arg Lys
        35

<210> SEQ ID NO 73
<211> LENGTH: 39
<212> TYPE: PRT
<213> ORGANISM: artificial
<220> FEATURE:
<223> OTHER INFORMATION: synthetic sequence

<400> SEQUENCE: 73

Lys Arg Lys Lys Arg Lys Lys Arg Lys Lys Arg Lys Lys Arg Lys Lys
1               5                   10                  15

Arg Lys Lys Arg Lys Lys Arg Lys Lys Arg Lys Lys Arg Lys Lys Arg
            20                  25                  30

Lys Lys Arg Lys Lys Arg Lys
        35

```
<210> SEQ ID NO 74
<211> LENGTH: 42
<212> TYPE: PRT
<213> ORGANISM: artificial
<220> FEATURE:
<223> OTHER INFORMATION: synthetic sequence

<400> SEQUENCE: 74

Lys Arg Lys Lys Arg Lys Lys Arg Lys Arg Ser Lys Arg Lys Lys Arg
1               5                   10                  15

Lys Lys Arg Lys Arg Ser Lys Arg Lys Lys Arg Lys Lys Arg Lys Arg
                20                  25                  30

Ser Lys Arg Lys Lys Arg Lys Lys Arg Lys
                35                  40

<210> SEQ ID NO 75
<211> LENGTH: 37
<212> TYPE: PRT
<213> ORGANISM: Homo sapiens

<400> SEQUENCE: 75

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
                20                  25                  30

Pro Arg Thr Glu Ser
            35

<210> SEQ ID NO 76
<211> LENGTH: 29
<212> TYPE: PRT
<213> ORGANISM: unknown
<220> FEATURE:
<223> OTHER INFORMATION: SMAP-29 sheep

<400> SEQUENCE: 76

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly
                20                  25

<210> SEQ ID NO 77
<211> LENGTH: 13
<212> TYPE: PRT
<213> ORGANISM: unknown
<220> FEATURE:
<223> OTHER INFORMATION: Indolicidine bovine

<400> SEQUENCE: 77

Ile Leu Pro Trp Lys Trp Pro Trp Trp Pro Trp Arg Arg
1               5                   10

<210> SEQ ID NO 78
<211> LENGTH: 18
<212> TYPE: PRT
<213> ORGANISM: unknown
<220> FEATURE:
<223> OTHER INFORMATION: Protegrin Porcine

<400> SEQUENCE: 78

Arg Gly Gly Arg Leu Cys Tyr Cys Arg Arg Arg Phe Cys Val Cys Val
1               5                   10                  15
```

-continued

Gly Arg

<210> SEQ ID NO 79
<211> LENGTH: 31
<212> TYPE: PRT
<213> ORGANISM: unknown
<220> FEATURE:
<223> OTHER INFORMATION: Cecropin P1 Mammal (pig)

<400> SEQUENCE: 79

Ser Trp Leu Ser Lys Thr Ala Lys Lys Leu Glu Asn Ser Ala Lys Lys
1               5                   10                  15

Arg Ile Ser Glu Gly Ile Ala Ile Ala Ile Gln Gly Gly Pro Arg
            20                  25                  30

<210> SEQ ID NO 80
<211> LENGTH: 23
<212> TYPE: PRT
<213> ORGANISM: unknown
<220> FEATURE:
<223> OTHER INFORMATION: Magainin frog

<400> SEQUENCE: 80

Gly Ile Gly Lys Phe Leu His Ser Ala Lys Phe Gly Lys Ala Phe
1               5                   10                  15

Val Gly Glu Ile Met Asn Ser
            20

<210> SEQ ID NO 81
<211> LENGTH: 25
<212> TYPE: PRT
<213> ORGANISM: unknown
<220> FEATURE:
<223> OTHER INFORMATION: Pleurocidin fish

<400> SEQUENCE: 81

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 82
<211> LENGTH: 36
<212> TYPE: PRT
<213> ORGANISM: Aedes aegypti

<400> SEQUENCE: 82

Gly Gly Leu Lys Lys Leu Gly Lys Lys Leu Glu Gly Ala Gly Lys Arg
1               5                   10                  15

Val Phe Asn Ala Ala Glu Lys Ala Leu Pro Val Val Ala Gly Ala Lys
            20                  25                  30

Ala Leu Arg Lys
        35

<210> SEQ ID NO 83
<211> LENGTH: 40
<212> TYPE: PRT
<213> ORGANISM: Drosophila melanogaster

<400> SEQUENCE: 83

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Pro Gln Gln Ala Ala

Asn Val Ala Ala Thr Ala Arg Gly
            35                  40

<210> SEQ ID NO 84
<211> LENGTH: 21
<212> TYPE: PRT
<213> ORGANISM: unknown
<220> FEATURE:
<223> OTHER INFORMATION: Buforin II vertebrate

<400> SEQUENCE: 84

Thr Arg Ser Ser Arg Ala Gly Leu Gln Phe Pro Val Gly Arg Val His
1               5                   10                  15

Arg Leu Leu Arg Lys
            20

<210> SEQ ID NO 85
<211> LENGTH: 39
<212> TYPE: PRT
<213> ORGANISM: unknown
<220> FEATURE:
<223> OTHER INFORMATION: Sarcotoxin IA Fly

<400> SEQUENCE: 85

Gly Trp Leu Lys Lys Ile Gly Lys Lys Ile Glu Arg Val Gly Gln His
1               5                   10                  15

Thr Arg Asp Ala Thr Ile Gln Gly Leu Gly Ile Ala Gln Gln Ala Ala
            20                  25                  30

Asn Val Ala Ala Thr Ala Arg
            35

<210> SEQ ID NO 86
<211> LENGTH: 17
<212> TYPE: PRT
<213> ORGANISM: Apis mellifera

<400> SEQUENCE: 86

Ala Asn Arg Pro Val Tyr Ile Pro Pro Pro Arg Pro Pro His Pro Arg
1               5                   10                  15

Leu

<210> SEQ ID NO 87
<211> LENGTH: 24
<212> TYPE: PRT
<213> ORGANISM: unknown
<220> FEATURE:
<223> OTHER INFORMATION: Ascaphine 5 Frog

<400> SEQUENCE: 87

Gly Ile Lys Asp Trp Ile Lys Gly Ala Ala Lys Lys Leu Ile Lys Thr
1               5                   10                  15

Val Ala Ser His Ile Ala Asn Gln
            20

<210> SEQ ID NO 88
<211> LENGTH: 22
<212> TYPE: PRT
<213> ORGANISM: unknown
<220> FEATURE:
<223> OTHER INFORMATION: Nigrocine 2 Frog

<400> SEQUENCE: 88

```
Gly Leu Leu Ser Lys Val Leu Gly Val Gly Lys Lys Val Leu Cys Gly
1               5                   10                  15

Val Ser Gly Leu Val Cys
            20
```

<210> SEQ ID NO 89
<211> LENGTH: 24
<212> TYPE: PRT
<213> ORGANISM: unknown
<220> FEATURE:
<223> OTHER INFORMATION: Pseudin 1 Rana Frog

<400> SEQUENCE: 89

```
Gly Leu Asn Thr Leu Lys Lys Val Phe Gln Gly Leu His Glu Ala Ile
1               5                   10                  15

Lys Leu Ile Asn Asn His Val Gln
            20
```

<210> SEQ ID NO 90
<211> LENGTH: 18
<212> TYPE: PRT
<213> ORGANISM: unknown
<220> FEATURE:
<223> OTHER INFORMATION: Ranalexin Frog

<400> SEQUENCE: 90

```
Phe Leu Gly Gly Leu Ile Val Pro Ala Met Ile Cys Ala Val Thr Lys
1               5                   10                  15

Lys Cys
```

<210> SEQ ID NO 91
<211> LENGTH: 26
<212> TYPE: PRT
<213> ORGANISM: unknown
<220> FEATURE:
<223> OTHER INFORMATION: Melittin bee

<400> SEQUENCE: 91

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 92
<211> LENGTH: 25
<212> TYPE: PRT
<213> ORGANISM: unknown
<220> FEATURE:
<223> OTHER INFORMATION: Lycotoxin 1 Spider

<400> SEQUENCE: 92

```
Ile Trp Leu Thr Ala Leu Lys Phe Leu Gly Lys His Ala Ala Lys Lys
1               5                   10                  15

Leu Ala Lys Gln Gln Leu Ser Lys Leu
            20                  25
```

<210> SEQ ID NO 93
<211> LENGTH: 19
<212> TYPE: PRT
<213> ORGANISM: unknown
<220> FEATURE:
<223> OTHER INFORMATION: Parasin 1 Fish

<400> SEQUENCE: 93

-continued

```
Lys Gly Arg Gly Lys Gln Gly Gly Lys Val Arg Ala Lys Ala Lys Thr
1               5                   10                  15

Arg Ser Ser

<210> SEQ ID NO 94
<211> LENGTH: 39
<212> TYPE: PRT
<213> ORGANISM: unknown
<220> FEATURE:
<223> OTHER INFORMATION: Buforin I Toad

<400> SEQUENCE: 94

Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
            35

<210> SEQ ID NO 95
<211> LENGTH: 34
<212> TYPE: PRT
<213> ORGANISM: unknown
<220> FEATURE:
<223> OTHER INFORMATION: Dermaseptin 1 Frog

<400> SEQUENCE: 95

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 96
<211> LENGTH: 12
<212> TYPE: PRT
<213> ORGANISM: unknown
<220> FEATURE:
<223> OTHER INFORMATION: Bactenecin 1 Cow

<400> SEQUENCE: 96

Arg Leu Cys Arg Ile Val Val Ile Arg Val Cys Arg
1               5                   10

<210> SEQ ID NO 97
<211> LENGTH: 21
<212> TYPE: PRT
<213> ORGANISM: unknown
<220> FEATURE:
<223> OTHER INFORMATION: Thanatin Insect

<400> SEQUENCE: 97

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 98
<211> LENGTH: 19
<212> TYPE: PRT
<213> ORGANISM: unknown
<220> FEATURE:
<223> OTHER INFORMATION: Brevinin 1T Rana frogs
```

```
<400> SEQUENCE: 98

Val Asn Pro Ile Ile Leu Gly Val Leu Pro Lys Val Cys Leu Ile Thr
1               5                   10                  15

Lys Lys Cys

<210> SEQ ID NO 99
<211> LENGTH: 26
<212> TYPE: PRT
<213> ORGANISM: unknown
<220> FEATURE:
<223> OTHER INFORMATION: Ranateurin 1 Rana frog

<400> SEQUENCE: 99

Ser Met Leu Ser Val Leu Lys Asn Leu Gly Lys Val Gly Leu Gly Phe
1               5                   10                  15

Val Ala Cys Lys Ile Asn Ile Lys Gln Cys
            20                  25

<210> SEQ ID NO 100
<211> LENGTH: 46
<212> TYPE: PRT
<213> ORGANISM: unknown
<220> FEATURE:
<223> OTHER INFORMATION: Esculentin 1 Rana frogs

<400> SEQUENCE: 100

Gly Ile Phe Ser Lys Leu Gly Arg Lys Lys Ile Lys Asn Leu Leu Ile
1               5                   10                  15

Ser Gly Leu Lys Asn Val Gly Lys Glu Val Gly Met Asp Val Val Arg
            20                  25                  30

Thr Gly Ile Lys Ile Ala Gly Cys Lys Ile Lys Gly Glu Cys
        35                  40                  45

<210> SEQ ID NO 101
<211> LENGTH: 17
<212> TYPE: PRT
<213> ORGANISM: Limulus polyphemus

<400> SEQUENCE: 101

Arg Trp Cys Phe Arg Val Cys Tyr Arg Gly Ile Cys Tyr Arg Lys Cys
1               5                   10                  15

Arg

<210> SEQ ID NO 102
<211> LENGTH: 25
<212> TYPE: PRT
<213> ORGANISM: unknown
<220> FEATURE:
<223> OTHER INFORMATION: Androctonin Scorpion

<400> SEQUENCE: 102

Arg Ser Val Cys Arg Gln Ile Lys Ile Cys Arg Arg Arg Gly Gly Cys
1               5                   10                  15

Tyr Tyr Lys Cys Thr Asn Arg Pro Tyr
            20                  25

<210> SEQ ID NO 103
<211> LENGTH: 30
<212> TYPE: PRT
<213> ORGANISM: Homo sapiens

<400> SEQUENCE: 103
```

```
Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30
```

<210> SEQ ID NO 104
<211> LENGTH: 38
<212> TYPE: PRT
<213> ORGANISM: unknown
<220> FEATURE:
<223> OTHER INFORMATION: beta-defensin cow

<400> SEQUENCE: 104

```
Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
            20                  25                  30

Lys Cys Cys Arg Lys Lys
            35
```

<210> SEQ ID NO 105
<211> LENGTH: 18
<212> TYPE: PRT
<213> ORGANISM: unknown
<220> FEATURE:
<223> OTHER INFORMATION: theta-defensin monkey

<400> SEQUENCE: 105

```
Gly Phe Cys Arg Cys Leu Cys Arg Arg Gly Val Cys Arg Cys Ile Cys
1               5                   10                  15

Thr Arg
```

<210> SEQ ID NO 106
<211> LENGTH: 40
<212> TYPE: PRT
<213> ORGANISM: unknown
<220> FEATURE:
<223> OTHER INFORMATION: defensin (sapecin A) insect

<400> SEQUENCE: 106

```
Ala Thr Cys Asp Leu Leu Ser Gly Thr Gly Ile Asn His Ser Ala Cys
1               5                   10                  15

Ala Ala His Cys Leu Leu Arg Gly Asn Arg Gly Gly Tyr Cys Asn Gly
            20                  25                  30

Lys Ala Val Cys Val Cys Arg Asn
            35                  40
```

<210> SEQ ID NO 107
<211> LENGTH: 46
<212> TYPE: PRT
<213> ORGANISM: unknown
<220> FEATURE:
<223> OTHER INFORMATION: Thionin (crambin) plant

<400> SEQUENCE: 107

```
Thr Thr Cys Cys Pro Ser Ile Val Ala Arg Ser Asn Phe Asn Val Cys
1               5                   10                  15

Arg Ile Pro Gly Thr Pro Glu Ala Ile Cys Ala Thr Tyr Thr Gly Cys
            20                  25                  30

Ile Ile Ile Pro Gly Ala Thr Cys Pro Gly Asp Tyr Ala Asn
            35                  40                  45
```

```
<210> SEQ ID NO 108
<211> LENGTH: 50
<212> TYPE: PRT
<213> ORGANISM: unknown
<220> FEATURE:
<223> OTHER INFORMATION: defensin from radish

<400> SEQUENCE: 108

Gln Lys Leu Cys Gln Arg Pro Ser Gly Thr Trp Ser Gly Val Cys Gly
1               5                   10                  15

Asn Asn Asn Ala Cys Lys Asn Gln Cys Ile Arg Leu Glu Lys Ala Arg
            20                  25                  30

His Gly Ser Cys Asn Tyr Val Phe Pro Ala His Cys Ile Cys Tyr Phe
        35                  40                  45

Pro Cys
    50

<210> SEQ ID NO 109
<211> LENGTH: 44
<212> TYPE: PRT
<213> ORGANISM: Drosophila melanogaster

<400> SEQUENCE: 109

Asp Cys Leu Ser Gly Arg Tyr Lys Gly Pro Cys Ala Val Trp Asp Asn
1               5                   10                  15

Glu Thr Cys Arg Arg Val Cys Lys Glu Glu Gly Arg Ser Ser Gly His
            20                  25                  30

Cys Ser Pro Ser Leu Lys Cys Trp Cys Glu Gly Cys
        35                  40

<210> SEQ ID NO 110
<211> LENGTH: 25
<212> TYPE: PRT
<213> ORGANISM: Homo sapiens

<400> SEQUENCE: 110

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 111
<211> LENGTH: 44
<212> TYPE: PRT
<213> ORGANISM: unknown
<220> FEATURE:
<223> OTHER INFORMATION: Bac 5 Cow

<400> SEQUENCE: 111

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

Pro Pro Phe Arg Pro Pro Leu Gly Arg Pro Phe Pro
        35                  40

<210> SEQ ID NO 112
<211> LENGTH: 39
<212> TYPE: PRT
<213> ORGANISM: unknown
<220> FEATURE:
<223> OTHER INFORMATION: PR-39 Pig
```

-continued

```
<400> SEQUENCE: 112

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
            35

<210> SEQ ID NO 113
<211> LENGTH: 20
<212> TYPE: PRT
<213> ORGANISM: unknown
<220> FEATURE:
<223> OTHER INFORMATION: Pyrrhocoricin Insect

<400> SEQUENCE: 113

Val Asp Lys Gly Ser Tyr Leu Pro Arg Pro Thr Pro Pro Arg Pro Ile
1               5                   10                  15

Tyr Asn Arg Asn
            20

<210> SEQ ID NO 114
<211> LENGTH: 24
<212> TYPE: PRT
<213> ORGANISM: Homo sapiens

<400> SEQUENCE: 114

Asp Ser His Ala Lys Arg His His Gly Tyr Lys Arg Lys Phe His Glu
1               5                   10                  15

Lys His His Ser His Arg Gly Tyr
            20

<210> SEQ ID NO 115
<211> LENGTH: 34
<212> TYPE: PRT
<213> ORGANISM: Limulus polyphemus

<400> SEQUENCE: 115

Gly Phe Lys Leu Lys Gly Met Ala Arg Ile Ser Cys Leu Pro Asn Gly
1               5                   10                  15

Gln Trp Ser Asn Phe Pro Pro Lys Cys Ile Arg Glu Cys Ala Met Val
            20                  25                  30

Ser Ser

<210> SEQ ID NO 116
<211> LENGTH: 18
<212> TYPE: PRT
<213> ORGANISM: artificial
<220> FEATURE:
<223> OTHER INFORMATION: synthetic sequence

<400> SEQUENCE: 116

Gly Phe Phe Ile Pro Ala Val Ile Leu Pro Ser Ile Ala Phe Leu Ile
1               5                   10                  15

Val Pro

<210> SEQ ID NO 117
<211> LENGTH: 5
<212> TYPE: PRT
<213> ORGANISM: artificial
<220> FEATURE:
<223> OTHER INFORMATION: synthetic sequence
```

<400> SEQUENCE: 117

Phe Phe Val Ala Pro
1               5

<210> SEQ ID NO 118
<211> LENGTH: 13
<212> TYPE: PRT
<213> ORGANISM: unknown
<220> FEATURE:
<223> OTHER INFORMATION: alpha4-helix of T4 lysozyme

<400> SEQUENCE: 118

Pro Asn Arg Ala Lys Arg Val Ile Thr Thr Phe Arg Thr
1               5                   10

<210> SEQ ID NO 119
<211> LENGTH: 27
<212> TYPE: PRT
<213> ORGANISM: artificial
<220> FEATURE:
<223> OTHER INFORMATION: synthetic sequence

<400> SEQUENCE: 119

Lys Arg Trp Val Lys Arg Val Lys Arg Val Lys Arg Trp Val Lys Arg
1               5                   10                  15

Val Val Arg Val Val Lys Arg Trp Val Lys Arg
            20                  25

<210> SEQ ID NO 120
<211> LENGTH: 25
<212> TYPE: PRT
<213> ORGANISM: artificial
<220> FEATURE:
<223> OTHER INFORMATION: synthetic sequence

<400> SEQUENCE: 120

Gly Lys Pro Gly Trp Leu Ile Lys Lys Ala Leu Val Phe Lys Lys Leu
1               5                   10                  15

Ile Arg Arg Pro Leu Lys Arg Leu Ala
            20                  25

<210> SEQ ID NO 121
<211> LENGTH: 291
<212> TYPE: PRT
<213> ORGANISM: artificial sequence
<220> FEATURE:
<223> OTHER INFORMATION: mutated KZ144 with C14S and C50S plus SMAP-29

<400> SEQUENCE: 121

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
            35                  40                  45

Thr Leu Leu Asn Leu Cys Gly Tyr Asp Val Gly Lys Pro Asp Gly Ile
        50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

```
Phe Ser Lys Tyr Ser Pro Pro Ile Pro Tyr Lys Thr Ile Pro Met Pro
                100                 105                 110

Thr Ala Asn Lys Ser Arg Ala Ala Ala Thr Pro Val Met Asn Ala Val
            115                 120                 125

Glu Asn Ala Thr Gly Val Arg Ser Gln Leu Leu Leu Thr Phe Ala Ser
        130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys
    290

<210> SEQ ID NO 122
<211> LENGTH: 291
<212> TYPE: PRT
<213> ORGANISM: artificial sequence
<220> FEATURE:
<223> OTHER INFORMATION: mutated KZ144 with T82I, A206V and S232 plus
      SMAP-29

<400> SEQUENCE: 122

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Cys Gln Leu Gln
        35                  40                  45

Thr Leu Leu Asn Leu Cys Gly Tyr Asp Val Gly Lys Pro Asp Gly Ile
50                  55                  60

Phe Gly Asn Asn Thr Phe Asn Gln Val Val Lys Phe Gln Lys Asp Asn
65                  70                  75                  80

Cys Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
                100                 105                 110

Ile Ala Asn Lys Ser Arg Ala Ala Ala Thr Pro Val Met Asn Ala Val
            115                 120                 125

Glu Asn Ala Thr Gly Val Arg Ser Gln Leu Leu Leu Thr Phe Ala Ser
        130                 135                 140

Ile Glu Ser Ala Phe Asp Tyr Glu Ile Lys Ala Lys Thr Ser Ser Ala
145                 150                 155                 160
```

Thr Gly Trp Phe Gln Phe Leu Thr Gly Thr Trp Lys Thr Met Ile Glu
            165                 170                 175

Asn Tyr Gly Met Lys Tyr Gly Val Leu Thr Asp Pro Thr Gly Ala Leu
        180                 185                 190

Arg Lys Asp Pro Arg Ile Ser Ala Leu Met Gly Ala Glu Leu Ile Lys
    195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Val Ala Arg Arg
225                 230                 235                 240

Phe Leu Thr Thr Gly Gln Asn Glu Leu Ala Ala Thr His Phe Pro Lys
            245                 250                 255

Glu Ala Gln Ala Asn Pro Thr Ile Phe Tyr Asn Lys Asp Gly Ser Pro
        260                 265                 270

Lys Thr Ile Gln Glu Val Tyr Asn Leu Met Asp Gly Lys Val Ala Ala
    275                 280                 285

His Arg Lys
    290

<210> SEQ ID NO 123
<211> LENGTH: 291
<212> TYPE: PRT
<213> ORGANISM: artificial sequence
<220> FEATURE:
<223> OTHER INFORMATION: mutated KZ144 with T82I, A206V, S232T, I122M
      and A160T plus SMAP-29

<400> SEQUENCE: 123

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Cys Gln Leu Gln
        35                  40                  45

Thr Leu Leu Asn Leu Cys Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Cys Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Ile Ala Asn Lys Ser Arg Ala Ala Ala Thr Pro Val Met Asn Ala Val
        115                 120                 125

Glu Asn Ala Thr Gly Val Arg Ser Gln Leu Leu Thr Phe Ala Ser
130                 135                 140

Ile Glu Ser Ala Phe Asp Tyr Glu Met Lys Ala Lys Thr Ser Ser Ala
145                 150                 155                 160

Thr Gly Trp Phe Gln Phe Leu Thr Gly Thr Trp Lys Thr Met Ile Glu
            165                 170                 175

Asn Tyr Gly Met Lys Tyr Gly Val Leu Thr Asp Pro Thr Gly Thr Leu
        180                 185                 190

Arg Lys Asp Pro Arg Ile Ser Ala Leu Met Gly Ala Glu Leu Ile Lys
    195                 200                 205

Glu Asn Met Asn Ile Leu Arg Pro Val Leu Lys Arg Glu Pro Thr Asp

```
            210                 215                 220
Thr Asp Leu Tyr Leu Ala His Phe Phe Gly Pro Gly Val Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Thr Ile Phe Tyr Asn Lys Asp Gly Ser Pro
                260                 265                 270

Lys Thr Ile Gln Glu Val Tyr Asn Leu Met Asp Gly Lys Val Ala Ala
            275                 280                 285

His Arg Lys
        290

<210> SEQ ID NO 124
<211> LENGTH: 291
<212> TYPE: PRT
<213> ORGANISM: artificial sequence
<220> FEATURE:
<223> OTHER INFORMATION: mutated KZ144 with C14S, C50S, I122M and A160T
      plus SMAP-29

<400> SEQUENCE: 124

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
        35                  40                  45

Thr Leu Leu Asn Leu Cys Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Ala Thr Pro Val Met Asn Ala Val
        115                 120                 125

Glu Asn Ala Thr Gly Val Arg Ser Gln Leu Leu Leu Thr Phe Ala Ser
    130                 135                 140

Ile Glu Ser Ala Phe Asp Tyr Glu Met Lys Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Thr Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
            260                 265                 270
```

```
Lys Thr Ile Gln Glu Val Tyr Asn Leu Met Asp Gly Lys Val Ala Ala
        275                 280                 285

His Arg Lys
    290

<210> SEQ ID NO 125
<211> LENGTH: 291
<212> TYPE: PRT
<213> ORGANISM: artificial sequence
<220> FEATURE:
<223> OTHER INFORMATION: mutated KZ144 with C14S, C23S and C50S plus
      SMAP-29

<400> SEQUENCE: 125

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
        35                  40                  45

Thr Leu Leu Asn Leu Ser Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Ala Thr Pro Val Met Asn Ala Val
        115                 120                 125

Glu Asn Ala Thr Gly Val Arg Ser Gln Leu Leu Leu Thr Phe Ala Ser
    130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys
    290

<210> SEQ ID NO 126
<211> LENGTH: 291
<212> TYPE: PRT
<213> ORGANISM: artificial sequence
```

<220> FEATURE:
<223> OTHER INFORMATION: mutated KZ144 with T82I, A206V, S232T, I122M,
     A160T, C14S and C50S plus SMAP-29

<400> SEQUENCE: 126

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
                20                  25                  30

Lys Val Leu Arg Lys Gly Asp Arg Gly Asp Glu Val Ser Gln Leu Gln
            35                  40                  45

Thr Leu Leu Asn Leu Cys Gly Tyr Asp Val Gly Lys Pro Asp Gly Ile
50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
                100                 105                 110

Ile Ala Asn Lys Ser Arg Ala Ala Ala Thr Pro Val Met Asn Ala Val
            115                 120                 125

Glu Asn Ala Thr Gly Val Arg Ser Gln Leu Leu Thr Phe Ala Ser
130                 135                 140

Ile Glu Ser Ala Phe Asp Tyr Glu Met Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Thr Leu
                180                 185                 190

Arg Lys Asp Pro Arg Ile Ser Ala Leu Met Gly Ala Glu Leu Ile Lys
            195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Val Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Thr Ile Phe Tyr Asn Lys Asp Gly Ser Pro
                260                 265                 270

Lys Thr Ile Gln Glu Val Tyr Asn Leu Met Asp Gly Lys Val Ala Ala
            275                 280                 285

His Arg Lys
    290

<210> SEQ ID NO 127
<211> LENGTH: 291
<212> TYPE: PRT
<213> ORGANISM: artificial sequence
<220> FEATURE:
<223> OTHER INFORMATION: mutated KZ144 with T82I, A206N, S232T, I122M,
     A160T, C14S and C50S plus SMAP-29

<400> SEQUENCE: 127

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
                20                  25                  30

Lys Val Leu Arg Lys Gly Asp Arg Gly Asp Glu Val Ser Gln Leu Gln
              35                  40                  45

Thr Leu Leu Asn Leu Cys Gly Tyr Asp Val Gly Lys Pro Asp Gly Ile
 50                  55                  60

Phe Gly Asn Asn Thr Phe Asn Gln Val Val Lys Phe Gln Lys Asp Asn
 65                  70                  75                  80

Ser Leu Asp Ser Asp Gly Ile Val Gly Lys Asn Thr Trp Ala Glu Leu
              85                  90                  95

Phe Ser Lys Tyr Ser Pro Pro Ile Pro Tyr Lys Thr Ile Pro Met Pro
             100                 105                 110

Ile Ala Asn Lys Ser Arg Ala Ala Thr Pro Val Met Asn Ala Val
             115                 120                 125

Glu Asn Ala Thr Gly Val Arg Ser Gln Leu Leu Thr Phe Ala Ser
             130                 135                 140

Ile Glu Ser Ala Phe Asp Tyr Glu Met Lys Ala Lys Thr Ser Ser Ala
145                 150                 155                 160

Thr Gly Trp Phe Gln Phe Leu Thr Gly Thr Trp Lys Thr Met Ile Glu
                 165                 170                 175

Asn Tyr Gly Met Lys Tyr Gly Val Leu Thr Asp Pro Thr Gly Thr Leu
             180                 185                 190

Arg Lys Asp Pro Arg Ile Ser Ala Leu Met Gly Ala Glu Leu Ile Lys
             195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Asn Ala Arg Arg
225                 230                 235                 240

Phe Leu Thr Thr Gly Gln Asn Glu Leu Ala Ala Thr His Phe Pro Lys
                 245                 250                 255

Glu Ala Gln Ala Asn Pro Thr Ile Phe Tyr Asn Lys Asp Gly Ser Pro
             260                 265                 270

Lys Thr Ile Gln Glu Val Tyr Asn Leu Met Asp Gly Lys Val Ala Ala
             275                 280                 285

His Arg Lys
 290

<210> SEQ ID NO 128
<211> LENGTH: 290
<212> TYPE: PRT
<213> ORGANISM: artificial sequence
<220> FEATURE:
<223> OTHER INFORMATION: mutated KZ144 with C14S and C50S plus SMAP-29
      without Met

<400> SEQUENCE: 128

Arg Gly Leu Arg Arg Leu Gly Arg Lys Ile Ala His Gly Val Lys Lys
1               5                  10                  15

Tyr Gly Pro Thr Val Leu Arg Ile Ile Arg Ile Ala Gly Gly Ser Lys
                 20                  25                  30

Val Leu Arg Lys Gly Asp Arg Gly Asp Glu Val Ser Gln Leu Gln Thr
             35                  40                  45

Leu Leu Asn Leu Cys Gly Tyr Asp Val Gly Lys Pro Asp Gly Ile Phe
 50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe

```
                    85                  90                  95
Ser Lys Tyr Ser Pro Ile Pro Tyr Lys Thr Ile Pro Met Pro Thr
                100                 105                 110

Ala Asn Lys Ser Arg Ala Ala Ala Thr Pro Val Met Asn Ala Val Glu
            115                 120                 125

Asn Ala Thr Gly Val Arg Ser Gln Leu Leu Leu Thr Phe Ala Ser Ile
        130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Ala Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
    210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Ser Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys
    290

<210> SEQ ID NO 129
<211> LENGTH: 290
<212> TYPE: PRT
<213> ORGANISM: artificial sequence
<220> FEATURE:
<223> OTHER INFORMATION: mutated KZ144 with T82I, A206V and S232 plus
      SMAP-29 without Met

<400> SEQUENCE: 129

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Cys Gln Leu Gln Thr
        35                  40                  45

Leu Leu Asn Leu Cys Gly Tyr Asp Val Gly Lys Pro Asp Gly Ile Phe
    50                  55                  60

Gly Asn Asn Thr Phe Asn Gln Val Val Lys Phe Gln Lys Asp Asn Cys
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Ile
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Leu Thr Phe Ala Ser Ile
    130                 135                 140
```

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
            165                 170                 175

Tyr Gly Met Lys Tyr Gly Val Leu Thr Asp Pro Thr Gly Ala Leu Arg
            180                 185                 190

Lys Asp Pro Arg Ile Ser Ala Leu Met Gly Ala Glu Leu Ile Lys Glu
            195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Val Ala Arg Arg Phe
225                 230                 235                 240

Leu Thr Thr Gly Gln Asn Glu Leu Ala Ala Thr His Phe Pro Lys Glu
            245                 250                 255

Ala Gln Ala Asn Pro Thr Ile Phe Tyr Asn Lys Asp Gly Ser Pro Lys
            260                 265                 270

Thr Ile Gln Glu Val Tyr Asn Leu Met Asp Gly Lys Val Ala Ala His
            275                 280                 285

Arg Lys
    290

<210> SEQ ID NO 130
<211> LENGTH: 290
<212> TYPE: PRT
<213> ORGANISM: artificial sequence
<220> FEATURE:
<223> OTHER INFORMATION: mutated KZ144 with T82I, A206V, S232T, I122M
      and A160T plus SMAP-29 without Met

<400> SEQUENCE: 130

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Cys Gln Leu Gln Thr
        35                  40                  45

Leu Leu Asn Leu Cys Gly Tyr Asp Val Gly Lys Pro Asp Gly Ile Phe
50                  55                  60

Gly Asn Asn Thr Phe Asn Gln Val Val Lys Phe Gln Lys Asp Asn Cys
65                  70                  75                  80

Leu Asp Ser Asp Gly Ile Val Gly Lys Asn Thr Trp Ala Glu Leu Phe
            85                  90                  95

Ser Lys Tyr Ser Pro Pro Ile Pro Tyr Lys Thr Ile Pro Met Pro Ile
            100                 105                 110

Ala Asn Lys Ser Arg Ala Ala Ala Thr Pro Val Met Asn Ala Val Glu
            115                 120                 125

Asn Ala Thr Gly Val Arg Ser Gln Leu Leu Leu Thr Phe Ala Ser Ile
            130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
            165                 170                 175

Tyr Gly Met Lys Tyr Gly Val Leu Thr Asp Pro Thr Gly Thr Leu Arg
            180                 185                 190

Lys Asp Pro Arg Ile Ser Ala Leu Met Gly Ala Glu Leu Ile Lys Glu
            195                 200                 205

```
Asn Met Asn Ile Leu Arg Pro Val Leu Lys Arg Glu Pro Thr Asp Thr
    210                 215                 220

Asp Leu Tyr Leu Ala His Phe Phe Gly Pro Gly Val Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Thr Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys
    290

<210> SEQ ID NO 131
<211> LENGTH: 290
<212> TYPE: PRT
<213> ORGANISM: artificial sequence
<220> FEATURE:
<223> OTHER INFORMATION: mutated KZ144 with C14S, C50S, I122M and A160T
      plus SMAP-29 without Met

<400> SEQUENCE: 131

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
                20                  25                  30

Val Leu Arg Lys Gly Asp Arg Gly Asp Glu Val Ser Gln Leu Gln Thr
            35                  40                  45

Leu Leu Asn Leu Cys Gly Tyr Asp Val Gly Lys Pro Asp Gly Ile Phe
50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Thr
                100                 105                 110

Ala Asn Lys Ser Arg Ala Ala Ala Thr Pro Val Met Asn Ala Val Glu
            115                 120                 125

Asn Ala Thr Gly Val Arg Ser Gln Leu Leu Leu Thr Phe Ala Ser Ile
        130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Thr Leu Arg
                180                 185                 190

Lys Asp Pro Arg Ile Ser Ala Leu Met Gly Ala Glu Leu Ile Lys Glu
            195                 200                 205

Asn Met Asn Ile Leu Arg Pro Val Leu Lys Arg Glu Pro Thr Asp Thr
    210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Ser Ile Phe Tyr Asn Lys Asp Gly Ser Pro Lys
```

```
                260             265             270
Thr Ile Gln Glu Val Tyr Asn Leu Met Asp Gly Lys Val Ala Ala His
        275             280             285

Arg Lys
    290

<210> SEQ ID NO 132
<211> LENGTH: 290
<212> TYPE: PRT
<213> ORGANISM: artificial sequence
<220> FEATURE:
<223> OTHER INFORMATION: mutated KZ144 with C14S, C23S and C50S plus
      SMAP-29 w/o Met

<400> SEQUENCE: 132

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Ser Gln Leu Gln Thr
        35                  40                  45

Leu Leu Asn Leu Ser Gly Tyr Asp Val Gly Lys Pro Asp Gly Ile Phe
50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Thr
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Leu Thr Phe Ala Ser Ile
130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Ala Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Ser Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys
    290

<210> SEQ ID NO 133
<211> LENGTH: 290
```

```
<212> TYPE: PRT
<213> ORGANISM: artificial sequence
<220> FEATURE:
<223> OTHER INFORMATION: mutated KZ144 with T82I, A206V, S232T, I122M,
      A160T, C14S and C50S plus SMAP-29 without Met

<400> SEQUENCE: 133

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Ser Gln Leu Gln Thr
        35                  40                  45

Leu Leu Asn Leu Cys Gly Tyr Asp Val Gly Lys Pro Asp Gly Ile Phe
    50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Ile
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Thr Phe Ala Ser Ile
    130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Thr Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
    210                 215                 220

Asp Leu Tyr Leu Ala His Phe Phe Gly Pro Gly Val Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Thr Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys
    290

<210> SEQ ID NO 134
<211> LENGTH: 290
<212> TYPE: PRT
<213> ORGANISM: artificial sequence
<220> FEATURE:
<223> OTHER INFORMATION: mutated KZ144 with T82I, A206N, S232T, I122M,
      A160T, C14S and C50S plus SMAP-29 without Met

<400> SEQUENCE: 134

Arg Gly Leu Arg Arg Leu Gly Arg Lys Ile Ala His Gly Val Lys Lys
1               5                   10                  15
```

```
Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Ser Gln Leu Gln Thr
        35                  40                  45

Leu Leu Asn Leu Cys Gly Tyr Asp Val Gly Lys Pro Asp Gly Ile Phe
    50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Ile
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Leu Thr Phe Ala Ser Ile
130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Thr Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Asn Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Thr Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys
    290

<210> SEQ ID NO 135
<211> LENGTH: 6
<212> TYPE: PRT
<213> ORGANISM: artificial sequence
<220> FEATURE:
<223> OTHER INFORMATION: His-Tag (6x)

<400> SEQUENCE: 135

His His His His His His
1               5

<210> SEQ ID NO 136
<211> LENGTH: 299
<212> TYPE: PRT
<213> ORGANISM: artificial sequence
<220> FEATURE:
<223> OTHER INFORMATION: mutated KZ144 with C14S and C50S plus SMAP-29
      and HisTag

<400> SEQUENCE: 136

Met Arg Gly Leu Arg Arg Leu Gly Arg Lys Ile Ala His Gly Val Lys
```

```
             1               5                  10                 15
           Lys Tyr Gly Pro Thr Val Leu Arg Ile Ile Arg Ile Ala Gly Gly Ser
                            20                 25                 30

Lys Val Leu Arg Lys Gly Asp Arg Gly Asp Glu Val Ser Gln Leu Gln
                            35                 40                 45

Thr Leu Leu Asn Leu Cys Gly Tyr Asp Val Gly Lys Pro Asp Gly Ile
                            50                 55                 60

Phe Gly Asn Asn Thr Phe Asn Gln Val Val Lys Phe Gln Lys Asp Asn
           65                   70                 75                 80

Ser Leu Asp Ser Asp Gly Ile Val Gly Lys Asn Thr Trp Ala Glu Leu
                            85                 90                 95

Phe Ser Lys Tyr Ser Pro Pro Ile Pro Tyr Lys Thr Ile Pro Met Pro
                            100                105                110

Thr Ala Asn Lys Ser Arg Ala Ala Ala Thr Pro Val Met Asn Ala Val
                            115                120                125

Glu Asn Ala Thr Gly Val Arg Ser Gln Leu Leu Leu Thr Phe Ala Ser
                            130                135                140

Ile Glu Ser Ala Phe Asp Tyr Glu Ile Lys Ala Lys Thr Ser Ser Ala
           145                  150                155                160

Thr Gly Trp Phe Gln Phe Leu Thr Gly Thr Trp Lys Thr Met Ile Glu
                            165                170                175

Asn Tyr Gly Met Lys Tyr Gly Val Leu Thr Asp Pro Thr Gly Ala Leu
                            180                185                190

Arg Lys Asp Pro Arg Ile Ser Ala Leu Met Gly Ala Glu Leu Ile Lys
                            195                200                205

Glu Asn Met Asn Ile Leu Arg Pro Val Leu Lys Arg Glu Pro Thr Asp
                            210                215                220

Thr Asp Leu Tyr Leu Ala His Phe Phe Gly Pro Gly Ala Ala Arg Arg
           225                  230                235                240

Phe Leu Thr Thr Gly Gln Asn Glu Leu Ala Ala Thr His Phe Pro Lys
                            245                250                255

Glu Ala Gln Ala Asn Pro Ser Ile Phe Tyr Asn Lys Asp Gly Ser Pro
                            260                265                270

Lys Thr Ile Gln Glu Val Tyr Asn Leu Met Asp Gly Lys Val Ala Ala
                            275                280                285

His Arg Lys Leu Glu His His His His His
                            290                295

<210> SEQ ID NO 137
<211> LENGTH: 299
<212> TYPE: PRT
<213> ORGANISM: artificial sequence
<220> FEATURE:
<223> OTHER INFORMATION: mutated KZ144 with T82I, A206V and S232 plus
      SMAP-29 and HisTag

<400> SEQUENCE: 137

Met Arg Gly Leu Arg Arg Leu Gly Arg Lys Ile Ala His Gly Val Lys
           1                5                  10                 15

Lys Tyr Gly Pro Thr Val Leu Arg Ile Ile Arg Ile Ala Gly Gly Ser
                            20                 25                 30

Lys Val Leu Arg Lys Gly Asp Arg Gly Asp Glu Val Cys Gln Leu Gln
                            35                 40                 45

Thr Leu Leu Asn Leu Cys Gly Tyr Asp Val Gly Lys Pro Asp Gly Ile
                            50                 55                 60
```

Phe Gly Asn Asn Thr Phe Asn Gln Val Val Lys Phe Gln Lys Asp Asn
65                  70                  75                  80

Cys Leu Asp Ser Asp Gly Ile Val Gly Lys Asn Thr Trp Ala Glu Leu
            85                  90                  95

Phe Ser Lys Tyr Ser Pro Pro Ile Pro Tyr Lys Thr Ile Pro Met Pro
        100                 105                 110

Ile Ala Asn Lys Ser Arg Ala Ala Ala Thr Pro Val Met Asn Ala Val
    115                 120                 125

Glu Asn Ala Thr Gly Val Arg Ser Gln Leu Leu Thr Phe Ala Ser
130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Val Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Thr Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys Leu Glu His His His His His
                290                 295

<210> SEQ ID NO 138
<211> LENGTH: 299
<212> TYPE: PRT
<213> ORGANISM: artificial sequence
<220> FEATURE:
<223> OTHER INFORMATION: mutated KZ144 with T82I, A206V, S232T, I122M
      and A160Tplus SMAP-29 and HisTag

<400> SEQUENCE: 138

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Cys Gln Leu Gln
        35                  40                  45

Thr Leu Leu Asn Leu Cys Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Cys Leu Asp Ser Asp Gly Ile Val Gly Lys Asn Thr Trp Ala Glu Leu
            85                  90                  95

Phe Ser Lys Tyr Ser Pro Pro Ile Pro Tyr Lys Thr Ile Pro Met Pro
        100                 105                 110

Ile Ala Asn Lys Ser Arg Ala Ala Ala Thr Pro Val Met Asn Ala Val
    115                 120                 125

```
Glu Asn Ala Thr Gly Val Arg Ser Gln Leu Leu Leu Thr Phe Ala Ser
            130                 135                 140

Ile Glu Ser Ala Phe Asp Tyr Glu Met Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Thr Leu
                180                 185                 190

Arg Lys Asp Pro Arg Ile Ser Ala Leu Met Gly Ala Glu Leu Ile Lys
            195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Val Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Thr Ile Phe Tyr Asn Lys Asp Gly Ser Pro
            260                 265                 270

Lys Thr Ile Gln Glu Val Tyr Asn Leu Met Asp Gly Lys Val Ala Ala
            275                 280                 285

His Arg Lys Leu Glu His His His His His
    290                 295
```

<210> SEQ ID NO 139
<211> LENGTH: 299
<212> TYPE: PRT
<213> ORGANISM: artificial sequence
<220> FEATURE:
<223> OTHER INFORMATION: mutated KZ144 with C14S, C50S, I122M and
    A160Tplus SMAP-29 and HisTag

<400> SEQUENCE: 139

```
Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
        35                  40                  45

Thr Leu Leu Asn Leu Cys Gly Tyr Asp Val Gly Lys Pro Asp Gly Ile
50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Ala Thr Pro Val Met Asn Ala Val
        115                 120                 125

Glu Asn Ala Thr Gly Val Arg Ser Gln Leu Leu Leu Thr Phe Ala Ser
            130                 135                 140

Ile Glu Ser Ala Phe Asp Tyr Glu Met Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Thr Leu
```

```
                180             185             190
Arg Lys Asp Pro Arg Ile Ser Ala Leu Met Gly Ala Glu Leu Ile Lys
            195                 200             205

Glu Asn Met Asn Ile Leu Arg Pro Val Leu Lys Arg Glu Pro Thr Asp
        210             215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
            245                 250                 255

Glu Ala Gln Ala Asn Pro Ser Ile Phe Tyr Asn Lys Asp Gly Ser Pro
        260                 265                 270

Lys Thr Ile Gln Glu Val Tyr Asn Leu Met Asp Gly Lys Val Ala Ala
        275                 280                 285

His Arg Lys Leu Glu His His His His His
        290                 295

<210> SEQ ID NO 140
<211> LENGTH: 299
<212> TYPE: PRT
<213> ORGANISM: artificial sequence
<220> FEATURE:
<223> OTHER INFORMATION: mutated KZ144 with C14S, C23S and C50Splus
      SMAP-29 and HisTag

<400> SEQUENCE: 140

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
        35                  40                  45

Thr Leu Leu Asn Leu Ser Gly Tyr Asp Val Gly Lys Pro Asp Gly Ile
50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Thr Pro Val Met Asn Ala Val
        115                 120                 125

Glu Asn Ala Thr Gly Val Arg Ser Gln Leu Leu Thr Phe Ala Ser
        130                 135             140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
            165                 170                 175

Asn Tyr Gly Met Lys Tyr Gly Val Leu Thr Asp Pro Thr Gly Ala Leu
            180                 185                 190

Arg Lys Asp Pro Arg Ile Ser Ala Leu Met Gly Ala Glu Leu Ile Lys
            195                 200             205

Glu Asn Met Asn Ile Leu Arg Pro Val Leu Lys Arg Glu Pro Thr Asp
        210             215                 220

Thr Asp Leu Tyr Leu Ala His Phe Phe Gly Pro Gly Ala Ala Arg Arg
225                 230                 235                 240
```

```
Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys Leu Glu His His His His His
        290                 295

<210> SEQ ID NO 141
<211> LENGTH: 299
<212> TYPE: PRT
<213> ORGANISM: artificial sequence
<220> FEATURE:
<223> OTHER INFORMATION: mutated KZ144 with T82I, A206V, S232T, I122M,
      A160T, C14S and C50Splus SMAP-29 and HisTag

<400> SEQUENCE: 141

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
        35                  40                  45

Thr Leu Leu Asn Leu Cys Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Ile Ala Asn Lys Ser Arg Ala Ala Ala Thr Pro Val Met Asn Ala Val
        115                 120                 125

Glu Asn Ala Thr Gly Val Arg Ser Gln Leu Leu Leu Thr Phe Ala Ser
    130                 135                 140

Ile Glu Ser Ala Phe Asp Tyr Glu Met Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Thr Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Val Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Thr Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys Leu Glu His His His His His
        290                 295
```

<210> SEQ ID NO 142
<211> LENGTH: 299
<212> TYPE: PRT
<213> ORGANISM: artificial sequence
<220> FEATURE:
<223> OTHER INFORMATION: mutated KZ144 with T82I, A206N, S232T, I122M,
    A160T, C14S and C50Splus SMAP-29 and HisTag

<400> SEQUENCE: 142

```
Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
            20                  25                  30

Lys Val Leu Arg Lys Gly Asp Arg Gly Asp Glu Val Ser Gln Leu Gln
        35                  40                  45

Thr Leu Leu Asn Leu Cys Gly Tyr Asp Val Gly Lys Pro Asp Gly Ile
    50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Ile Ala Asn Lys Ser Arg Ala Ala Ala Thr Pro Val Met Asn Ala Val
        115                 120                 125

Glu Asn Ala Thr Gly Val Arg Ser Gln Leu Leu Leu Thr Phe Ala Ser
    130                 135                 140

Ile Glu Ser Ala Phe Asp Tyr Glu Met Lys Ala Lys Thr Ser Ser Ala
145                 150                 155                 160

Thr Gly Trp Phe Gln Phe Leu Thr Gly Thr Trp Lys Thr Met Ile Glu
                165                 170                 175

Asn Tyr Gly Met Lys Tyr Gly Val Leu Thr Asp Pro Thr Gly Thr Leu
            180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
    210                 215                 220

Thr Asp Leu Tyr Leu Ala His Phe Phe Gly Pro Gly Asn Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Thr Ile Phe Tyr Asn Lys Asp Gly Ser Pro
            260                 265                 270

Lys Thr Ile Gln Glu Val Tyr Asn Leu Met Asp Gly Lys Val Ala Ala
        275                 280                 285

His Arg Lys Leu Glu His His His His His
    290                 295
```

<210> SEQ ID NO 143
<211> LENGTH: 298
<212> TYPE: PRT
<213> ORGANISM: artificial sequence
<220> FEATURE:
<223> OTHER INFORMATION: mutated KZ144 with C14S and C50S plus SMAP-29
    and HisTag, w/o Met

<400> SEQUENCE: 143

```
Arg Gly Leu Arg Arg Leu Gly Arg Lys Ile Ala His Gly Val Lys Lys
  1               5                  10                  15

Tyr Gly Pro Thr Val Leu Arg Ile Ile Arg Ile Ala Gly Gly Ser Lys
                 20                  25                  30

Val Leu Arg Lys Gly Asp Arg Gly Asp Glu Val Ser Gln Leu Gln Thr
             35                  40                  45

Leu Leu Asn Leu Cys Gly Tyr Asp Val Gly Lys Pro Asp Gly Ile Phe
 50                  55                  60

Gly Asn Asn Thr Phe Asn Gln Val Val Lys Phe Gln Lys Asp Asn Ser
 65                  70                  75                  80

Leu Asp Ser Asp Gly Ile Val Gly Lys Asn Thr Trp Ala Glu Leu Phe
                 85                  90                  95

Ser Lys Tyr Ser Pro Pro Ile Pro Tyr Lys Thr Ile Pro Met Pro Thr
                100                 105                 110

Ala Asn Lys Ser Arg Ala Ala Ala Thr Pro Val Met Asn Ala Val Glu
            115                 120                 125

Asn Ala Thr Gly Val Arg Ser Gln Leu Leu Leu Thr Phe Ala Ser Ile
130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Ala Leu Arg
                180                 185                 190

Lys Asp Pro Arg Ile Ser Ala Leu Met Gly Ala Glu Leu Ile Lys Glu
            195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Ser Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys Leu Glu His His His His His His
        290                 295

<210> SEQ ID NO 144
<211> LENGTH: 298
<212> TYPE: PRT
<213> ORGANISM: artificial sequence
<220> FEATURE:
<223> OTHER INFORMATION: mutated KZ144 with T82I, A206V and S232 plus
      SMAP-29 and HisTag, w/o Met

<400> SEQUENCE: 144

Arg Gly Leu Arg Arg Leu Gly Arg Lys Ile Ala His Gly Val Lys Lys
  1               5                  10                  15

Tyr Gly Pro Thr Val Leu Arg Ile Ile Arg Ile Ala Gly Gly Ser Lys
                 20                  25                  30

Val Leu Arg Lys Gly Asp Arg Gly Asp Glu Val Cys Gln Leu Gln Thr
             35                  40                  45

Leu Leu Asn Leu Cys Gly Tyr Asp Val Gly Lys Pro Asp Gly Ile Phe
```

```
                50                  55                  60
Gly Asn Asn Thr Phe Asn Gln Val Val Lys Phe Gln Lys Asp Asn Cys
 65                  70                  75                  80

Leu Asp Ser Asp Gly Ile Val Gly Lys Asn Thr Trp Ala Glu Leu Phe
                 85                  90                  95

Ser Lys Tyr Ser Pro Pro Ile Pro Tyr Lys Thr Ile Pro Met Pro Ile
                100                 105                 110

Ala Asn Lys Ser Arg Ala Ala Ala Thr Pro Val Met Asn Ala Val Glu
                115                 120                 125

Asn Ala Thr Gly Val Arg Ser Gln Leu Leu Leu Thr Phe Ala Ser Ile
        130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Ala Leu Arg
                180                 185                 190

Lys Asp Pro Arg Ile Ser Ala Leu Met Gly Ala Glu Leu Ile Lys Glu
                195                 200                 205

Asn Met Asn Ile Leu Arg Pro Val Leu Lys Arg Glu Pro Thr Asp Thr
        210                 215                 220

Asp Leu Tyr Leu Ala His Phe Phe Gly Pro Gly Val Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Thr Ile Phe Tyr Asn Lys Asp Gly Ser Pro Lys
                260                 265                 270

Thr Ile Gln Glu Val Tyr Asn Leu Met Asp Gly Lys Val Ala Ala His
        275                 280                 285

Arg Lys Leu Glu His His His His His His
    290                 295

<210> SEQ ID NO 145
<211> LENGTH: 298
<212> TYPE: PRT
<213> ORGANISM: artificial sequence
<220> FEATURE:
<223> OTHER INFORMATION: mutated KZ144 with T82I, A206V, S232T, I122M
      and A160Tplus SMAP-29 and HisTag, w/o Met

<400> SEQUENCE: 145

Arg Gly Leu Arg Arg Leu Gly Arg Lys Ile Ala His Gly Val Lys Lys
 1               5                  10                  15

Tyr Gly Pro Thr Val Leu Arg Ile Ile Arg Ile Ala Gly Gly Ser Lys
                20                  25                  30

Val Leu Arg Lys Gly Asp Arg Gly Asp Glu Val Cys Gln Leu Gln Thr
             35                  40                  45

Leu Leu Asn Leu Cys Gly Tyr Asp Val Gly Lys Pro Asp Gly Ile Phe
        50                  55                  60

Gly Asn Asn Thr Phe Asn Gln Val Val Lys Phe Gln Lys Asp Asn Cys
 65                  70                  75                  80

Leu Asp Ser Asp Gly Ile Val Gly Lys Asn Thr Trp Ala Glu Leu Phe
                 85                  90                  95

Ser Lys Tyr Ser Pro Pro Ile Pro Tyr Lys Thr Ile Pro Met Pro Ile
                100                 105                 110
```

Ala Asn Lys Ser Arg Ala Ala Ala Thr Pro Val Met Asn Ala Val Glu
            115                 120                 125

Asn Ala Thr Gly Val Arg Ser Gln Leu Leu Thr Phe Ala Ser Ile
        130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Thr Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Val Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Thr Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys Leu Glu His His His His His His
        290                 295

<210> SEQ ID NO 146
<211> LENGTH: 298
<212> TYPE: PRT
<213> ORGANISM: artificial sequence
<220> FEATURE:
<223> OTHER INFORMATION: mutated KZ144 with C14S, C50S, I122M and
      A160Tplus SMAP-29 and HisTag, w/o Met

<400> SEQUENCE: 146

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Ser Gln Leu Gln Thr
        35                  40                  45

Leu Leu Asn Leu Cys Gly Tyr Asp Val Gly Lys Pro Asp Gly Ile Phe
50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Thr
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Thr Phe Ala Ser Ile
    130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

```
Tyr Gly Met Lys Tyr Gly Val Leu Thr Asp Pro Thr Gly Thr Leu Arg
            180                 185                 190

Lys Asp Pro Arg Ile Ser Ala Leu Met Gly Ala Glu Leu Ile Lys Glu
            195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Ala Ala Arg Arg Phe
225                 230                 235                 240

Leu Thr Thr Gly Gln Asn Glu Leu Ala Ala Thr His Phe Pro Lys Glu
            245                 250                 255

Ala Gln Ala Asn Pro Ser Ile Phe Tyr Asn Lys Asp Gly Ser Pro Lys
            260                 265                 270

Thr Ile Gln Glu Val Tyr Asn Leu Met Asp Gly Lys Val Ala Ala His
            275                 280                 285

Arg Lys Leu Glu His His His His His His
            290                 295

<210> SEQ ID NO 147
<211> LENGTH: 298
<212> TYPE: PRT
<213> ORGANISM: artificial sequence
<220> FEATURE:
<223> OTHER INFORMATION: mutated KZ144 with C14S, C23S and C50Splus
      SMAP-29 and HisTag, w/o Met

<400> SEQUENCE: 147

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Ser Gln Leu Gln Thr
            35                  40                  45

Leu Leu Asn Leu Ser Gly Tyr Asp Val Gly Lys Pro Asp Gly Ile Phe
50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
            85                  90                  95

Ser Lys Tyr Ser Pro Pro Ile Pro Tyr Lys Thr Ile Pro Met Pro Thr
            100                 105                 110

Ala Asn Lys Ser Arg Ala Ala Ala Thr Pro Val Met Asn Ala Val Glu
            115                 120                 125

Asn Ala Thr Gly Val Arg Ser Gln Leu Leu Leu Thr Phe Ala Ser Ile
130                 135                 140

Glu Ser Ala Phe Asp Tyr Glu Ile Lys Ala Lys Thr Ser Ser Ala Thr
145                 150                 155                 160

Gly Trp Phe Gln Phe Leu Thr Gly Thr Trp Lys Thr Met Ile Glu Asn
            165                 170                 175

Tyr Gly Met Lys Tyr Gly Val Leu Thr Asp Pro Thr Gly Ala Leu Arg
            180                 185                 190

Lys Asp Pro Arg Ile Ser Ala Leu Met Gly Ala Glu Leu Ile Lys Glu
            195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Ala Ala Arg Arg Phe
```

```
            225                 230                 235                 240

Leu Thr Thr Gly Gln Asn Glu Leu Ala Ala Thr His Phe Pro Lys Glu
                245                 250                 255

Ala Gln Ala Asn Pro Ser Ile Phe Tyr Asn Lys Asp Gly Ser Pro Lys
                260                 265                 270

Thr Ile Gln Glu Val Tyr Asn Leu Met Asp Gly Lys Val Ala Ala His
                275                 280                 285

Arg Lys Leu Glu His His His His His His
                290                 295

<210> SEQ ID NO 148
<211> LENGTH: 298
<212> TYPE: PRT
<213> ORGANISM: artificial sequence
<220> FEATURE:
<223> OTHER INFORMATION: mutated KZ144 with T82I, A206V, S232T, I122M,
      A160T, C14S and C50Splus SMAP-29 and HisTag, w/o Met

<400> SEQUENCE: 148

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
                20                  25                  30

Val Leu Arg Lys Gly Asp Arg Gly Asp Glu Val Ser Gln Leu Gln Thr
                35                  40                  45

Leu Leu Asn Leu Cys Gly Tyr Asp Val Gly Lys Pro Asp Gly Ile Phe
            50                  55                  60

Gly Asn Asn Thr Phe Asn Gln Val Val Lys Phe Gln Lys Asp Asn Ser
65              70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Ile
                100                 105                 110

Ala Asn Lys Ser Arg Ala Ala Ala Thr Pro Val Met Asn Ala Val Glu
                115                 120                 125

Asn Ala Thr Gly Val Arg Ser Gln Leu Leu Thr Phe Ala Ser Ile
                130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Thr Leu Arg
                180                 185                 190

Lys Asp Pro Arg Ile Ser Ala Leu Met Gly Ala Glu Leu Ile Lys Glu
                195                 200                 205

Asn Met Asn Ile Leu Arg Pro Val Leu Lys Arg Glu Pro Thr Asp Thr
                210                 215                 220

Asp Leu Tyr Leu Ala His Phe Phe Gly Pro Gly Val Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Thr Ile Phe Tyr Asn Lys Asp Gly Ser Pro Lys
                260                 265                 270

Thr Ile Gln Glu Val Tyr Asn Leu Met Asp Gly Lys Val Ala Ala His
                275                 280                 285
```

Arg Lys Leu Glu His His His His His
    290                 295

<210> SEQ ID NO 149
<211> LENGTH: 298
<212> TYPE: PRT
<213> ORGANISM: artificial sequence
<220> FEATURE:
<223> OTHER INFORMATION: mutated KZ144 with T82I, A206N, S232T, I122M,
      A160T, C14S and C50S plus SMAP-29 and HisTag, w/o Met

<400> SEQUENCE: 149

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala Gly Gly Ser Lys
            20                  25                  30

Val Leu Arg Lys Gly Asp Arg Gly Asp Glu Val Ser Gln Leu Gln Thr
        35                  40                  45

Leu Leu Asn Leu Cys Gly Tyr Asp Val Gly Lys Pro Asp Gly Ile Phe
    50                  55                  60

Gly Asn Asn Thr Phe Asn Gln Val Val Lys Phe Gln Lys Asp Asn Ser
65                  70                  75                  80

Leu Asp Ser Asp Gly Ile Val Gly Lys Asn Thr Trp Ala Glu Leu Phe
                85                  90                  95

Ser Lys Tyr Ser Pro Pro Ile Pro Tyr Lys Thr Ile Pro Met Pro Ile
            100                 105                 110

Ala Asn Lys Ser Arg Ala Ala Ala Thr Pro Val Met Asn Ala Val Glu
        115                 120                 125

Asn Ala Thr Gly Val Arg Ser Gln Leu Leu Leu Thr Phe Ala Ser Ile
130                 135                 140

Glu Ser Ala Phe Asp Tyr Glu Met Lys Ala Lys Thr Ser Ser Ala Thr
145                 150                 155                 160

Gly Trp Phe Gln Phe Leu Thr Gly Thr Trp Lys Thr Met Ile Glu Asn
                165                 170                 175

Tyr Gly Met Lys Tyr Gly Val Leu Thr Asp Pro Thr Gly Thr Leu Arg
            180                 185                 190

Lys Asp Pro Arg Ile Ser Ala Leu Met Gly Ala Glu Leu Ile Lys Glu
        195                 200                 205

Asn Met Asn Ile Leu Arg Pro Val Leu Lys Arg Glu Pro Thr Asp Thr
210                 215                 220

Asp Leu Tyr Leu Ala His Phe Phe Gly Pro Gly Asn Ala Arg Arg Phe
225                 230                 235                 240

Leu Thr Thr Gly Gln Asn Glu Leu Ala Ala Thr His Phe Pro Lys Glu
                245                 250                 255

Ala Gln Ala Asn Pro Thr Ile Phe Tyr Asn Lys Asp Gly Ser Pro Lys
            260                 265                 270

Thr Ile Gln Glu Val Tyr Asn Leu Met Asp Gly Lys Val Ala Ala His
        275                 280                 285

Arg Lys Leu Glu His His His His His
    290                 295

<210> SEQ ID NO 150
<211> LENGTH: 190
<212> TYPE: PRT
<213> ORGANISM: Artificial Sequence
<220> FEATURE:
<223> OTHER INFORMATION: KZ144 fragment 71-260 with Y75A

<400> SEQUENCE: 150

```
Pro Pro Ile Pro Ala Lys Thr Ile Pro Met Pro Thr Ala Asn Lys Ser
1               5                   10                  15

Arg Ala Ala Ala Thr Pro Val Met Asn Ala Val Glu Asn Ala Thr Gly
                20                  25                  30

Val Arg Ser Gln Leu Leu Leu Thr Phe Ala Ser Ile Glu Ser Ala Phe
            35                  40                  45

Asp Tyr Glu Ile Lys Ala Lys Thr Ser Ser Ala Thr Gly Trp Phe Gln
        50                  55                  60

Phe Leu Thr Gly Thr Trp Lys Thr Met Ile Glu Asn Tyr Gly Met Lys
65                  70                  75                  80

Tyr Gly Val Leu Thr Asp Pro Thr Gly Ala Leu Arg Lys Asp Pro Arg
                85                  90                  95

Ile Ser Ala Leu Met Gly Ala Glu Leu Ile Lys Glu Asn Met Asn Ile
            100                 105                 110

Leu Arg Pro Val Leu Lys Arg Glu Pro Thr Asp Thr Asp Leu Tyr Leu
        115                 120                 125

Ala His Phe Phe Gly Pro Gly Ala Ala Arg Arg Phe Leu Thr Thr Gly
    130                 135                 140

Gln Asn Glu Leu Ala Ala Thr His Phe Pro Lys Glu Ala Gln Ala Asn
145                 150                 155                 160

Pro Ser Ile Phe Tyr Asn Lys Asp Gly Ser Pro Lys Thr Ile Gln Glu
                165                 170                 175

Val Tyr Asn Leu Met Asp Gly Lys Val Ala Ala His Arg Lys
            180                 185                 190
```

<210> SEQ ID NO 151
<211> LENGTH: 299
<212> TYPE: PRT
<213> ORGANISM: Artificial Sequence
<220> FEATURE:
<223> OTHER INFORMATION: KZ144 plus SMAP-29 and HisTag

<400> SEQUENCE: 151

```
Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Gly Gly Ser
                20                  25                  30

Lys Val Leu Arg Lys Gly Asp Arg Gly Asp Glu Val Cys Gln Leu Gln
            35                  40                  45

Thr Leu Leu Asn Leu Cys Gly Tyr Asp Val Gly Lys Pro Asp Gly Ile
        50                  55                  60

Phe Gly Asn Asn Thr Phe Asn Gln Val Val Lys Phe Gln Lys Asp Asn
65                  70                  75                  80

Cys Leu Asp Ser Asp Gly Ile Val Gly Lys Asn Thr Trp Ala Glu Leu
                85                  90                  95

Phe Ser Lys Tyr Ser Pro Pro Ile Pro Tyr Lys Thr Ile Pro Met Pro
            100                 105                 110

Thr Ala Asn Lys Ser Arg Ala Ala Ala Thr Pro Val Met Asn Ala Val
        115                 120                 125

Glu Asn Ala Thr Gly Val Arg Ser Gln Leu Leu Leu Thr Phe Ala Ser
    130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
```

```
                165                 170                 175
Asn Tyr Gly Met Lys Tyr Gly Val Leu Thr Asp Pro Thr Gly Ala Leu
        180                 185                 190

Arg Lys Asp Pro Arg Ile Ser Ala Leu Met Gly Ala Glu Leu Ile Lys
        195                 200                 205

Glu Asn Met Asn Ile Leu Arg Pro Val Leu Lys Arg Glu Pro Thr Asp
        210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                245                 250                 255

Glu Ala Gln Ala Asn Pro Ser Ile Phe Tyr Asn Lys Asp Gly Ser Pro
        260                 265                 270

Lys Thr Ile Gln Glu Val Tyr Asn Leu Met Asp Gly Lys Val Ala Ala
        275                 280                 285

His Arg Lys Leu Glu His His His His His His
        290                 295

<210> SEQ ID NO 152
<211> LENGTH: 256
<212> TYPE: PRT
<213> ORGANISM: Artificial sequence
<220> FEATURE:
<223> OTHER INFORMATION: KZ144 without N-terminal methionine, with
      selenomethionine instead of methionine residues
<220> FEATURE:
<221> NAME/KEY: misc_feature
<222> LOCATION: (79)..(79)
<223> OTHER INFORMATION: Xaa is selenomethionine
<220> FEATURE:
<221> NAME/KEY: misc_feature
<222> LOCATION: (93)..(93)
<223> OTHER INFORMATION: Xaa is selenomethionine
<220> FEATURE:
<221> NAME/KEY: misc_feature
<222> LOCATION: (142)..(142)
<223> OTHER INFORMATION: Xaa is selenomethionine
<220> FEATURE:
<221> NAME/KEY: misc_feature
<222> LOCATION: (148)..(148)
<223> OTHER INFORMATION: Xaa is selenomethionine
<220> FEATURE:
<221> NAME/KEY: misc_feature
<222> LOCATION: (170)..(170)
<223> OTHER INFORMATION: Xaa is selenomethionine
<220> FEATURE:
<221> NAME/KEY: misc_feature
<222> LOCATION: (179)..(179)
<223> OTHER INFORMATION: Xaa is selenomethionine
<220> FEATURE:
<221> NAME/KEY: misc_feature
<222> LOCATION: (250)..(250)
<223> OTHER INFORMATION: Xaa is selenomethionine

<400> SEQUENCE: 152

Lys Val Leu Arg Lys Gly Asp Arg Gly Asp Glu Val Cys Gln Leu Gln
1               5                   10                  15

Thr Leu Leu Asn Leu Cys Gly Tyr Asp Val Gly Lys Pro Asp Gly Ile
            20                  25                  30

Phe Gly Asn Asn Thr Phe Asn Gln Val Val Lys Phe Gln Lys Asp Asn
        35                  40                  45

Cys Leu Asp Ser Asp Gly Ile Val Gly Lys Asn Thr Trp Ala Glu Leu
    50                  55                  60

Phe Ser Lys Tyr Ser Pro Pro Ile Pro Tyr Lys Thr Ile Pro Xaa Pro
65                  70                  75                  80
```

-continued

```
Thr Ala Asn Lys Ser Arg Ala Ala Thr Pro Val Xaa Asn Ala Val
                85                  90              95
Glu Asn Ala Thr Gly Val Arg Ser Gln Leu Leu Leu Thr Phe Ala Ser
                100             105                 110
Ile Glu Ser Ala Phe Asp Tyr Glu Ile Lys Ala Lys Thr Ser Ser Ala
            115             120                 125
Thr Gly Trp Phe Gln Phe Leu Thr Gly Thr Trp Lys Thr Xaa Ile Glu
    130             135                 140
Asn Tyr Gly Xaa Lys Tyr Gly Val Leu Thr Asp Pro Thr Gly Ala Leu
145             150                 155                 160
Arg Lys Asp Pro Arg Ile Ser Ala Leu Xaa Gly Ala Glu Leu Ile Lys
                165                 170                 175
Glu Asn Xaa Asn Ile Leu Arg Pro Val Leu Lys Arg Glu Pro Thr Asp
            180             185                 190
Thr Asp Leu Tyr Leu Ala His Phe Phe Gly Pro Gly Ala Ala Arg Arg
    195             200                 205
Phe Leu Thr Thr Gly Gln Asn Glu Leu Ala Ala Thr His Phe Pro Lys
        210             215                 220
Glu Ala Gln Ala Asn Pro Ser Ile Phe Tyr Asn Lys Asp Gly Ser Pro
225             230                 235                 240
Lys Thr Ile Gln Glu Val Tyr Asn Leu Xaa Asn Ile Leu Arg Pro Val
                245                 250                 255
```